(12) United States Patent
Gammelsaeter et al.

(10) Patent No.: US 8,075,920 B2
(45) Date of Patent: Dec. 13, 2011

(54) ADMINISTRATION OF CELLS AND CELLULAR EXTRACTS FOR REJUVENATION

(75) Inventors: Runhild Gammelsaeter, Oslo (NO); Jan Remmereit, Volda (NO)

(73) Assignee: Regenics A/S, Oslo (NO)

( * ) Notice: Subject to any disclaimer, the term of this patent is extended or adjusted under 35 U.S.C. 154(b) by 656 days.

(21) Appl. No.: 11/801,778

(22) Filed: May 11, 2007

(65) Prior Publication Data
US 2009/0175927 A1    Jul. 9, 2009

Related U.S. Application Data

(60) Provisional application No. 60/799,560, filed on May 11, 2006.

(51) Int. Cl.
| | |
|---|---|
| A61K 35/60 | (2006.01) |
| A61K 35/12 | (2006.01) |
| A61K 35/52 | (2006.01) |
| A61K 35/54 | (2006.01) |
| C12N 5/00 | (2006.01) |
| C12N 5/02 | (2006.01) |

(52) U.S. Cl. ........ 424/523; 424/520; 424/561; 435/325; 435/375

(58) Field of Classification Search .................. 424/523
See application file for complete search history.

(56) References Cited

U.S. PATENT DOCUMENTS

| | | | |
|---|---|---|---|
| 3,852,489 A * | 12/1974 | Yip ............................ | 426/268 |
| 5,061,620 A | 10/1991 | Tsukamoto et al. | |
| 5,166,065 A | 11/1992 | Williams et al. | |
| 5,197,985 A | 3/1993 | Caplan et al. | |
| 5,226,914 A | 7/1993 | Caplans et al. | |
| 5,340,740 A | 8/1994 | Petitte et al. | |
| 5,453,357 A | 9/1995 | Hogan et al. | |
| 5,486,359 A | 1/1996 | Caplan et al. | |
| 5,523,226 A | 6/1996 | Wheeler et al. | |
| 5,589,376 A | 12/1996 | Anderson et al. | |
| 5,591,625 A | 1/1997 | Gerson et al. | |
| 5,651,992 A | 7/1997 | Wangh et al. | |
| 5,654,183 A | 8/1997 | Anderson et al. | |
| 5,672,499 A | 9/1997 | Anderson et al. | |
| 5,716,827 A | 2/1998 | Tsukamoto et al. | |
| 5,750,376 A | 5/1998 | Weiss et al. | |
| 5,750,397 A | 5/1998 | Tsukamoto et al. | |
| 5,843,780 A | 12/1998 | Thomson et al. | |
| 5,849,553 A | 12/1998 | Anderson et al. | |
| 5,968,829 A | 10/1999 | Carpenter et al. | |
| 5,985,333 A | 11/1999 | Vainberg et al. | |
| 6,177,550 B1 | 1/2001 | Meyer et al. | |
| 6,200,806 B1 | 3/2001 | Thomson et al. | |
| 6,673,603 B2 | 1/2004 | Baetge et al. | |
| 2002/0142397 A1 | 10/2002 | Collas et al. | |
| 2003/0046722 A1 | 3/2003 | Collas et al. | |
| 2004/0072288 A1 | 4/2004 | Collas et al. | |
| 2005/0014258 A1 | 1/2005 | Collas et al. | |
| 2005/0214257 A1 | 9/2005 | Zhao et al. | |
| 2005/0260181 A1* | 11/2005 | Girsh ........................ | 424/93.45 |
| 2005/0271751 A1 | 12/2005 | Perrier et al. | |
| 2006/0014282 A1 | 1/2006 | Fortunel et al. | |
| 2006/0212952 A1 | 9/2006 | Collas et al. | |
| 2007/0134792 A1 | 6/2007 | Dai et al. | |

FOREIGN PATENT DOCUMENTS

| | | | |
|---|---|---|---|
| CN | 1343496 A | | 4/2002 |
| DE | 2129212 A | * | 12/1971 |
| DE | 19917532 A1 | | 10/2000 |
| DE | 10001740 A1 | | 7/2001 |
| EP | 1600501 | | 4/2005 |
| EP | 1629830 A | | 3/2006 |
| FR | 2500305 A1 | | 8/1982 |
| FR | 2827171 A1 | | 1/2003 |
| FR | 2843123 A | | 2/2004 |
| FR | 2096704 | | 8/2007 |
| JP | 08169837 | | 7/1996 |
| KR | 20030075297 | | 4/2003 |
| RU | 2032398 | | 4/1995 |
| RU | 2110984 C1 | | 5/1998 |
| RU | 2232587 C1 | | 7/2004 |
| WO | WO89/07425 A | | 8/1989 |
| WO | WO 92/22584 | | 12/1992 |
| WO | WO01/89540 A | | 11/2001 |
| WO | WO02/18441 A | | 3/2002 |
| WO | WO2004/084828 A | | 10/2004 |
| WO | WO2005/099758 A | | 10/2005 |

OTHER PUBLICATIONS

Irie and Seki, Comparative Biochemistry and Physiology Part B: Biochemistry and Molecular Biology, 2002, 131:209-219.*
Li et al (2003, Cell Research, 13:159-169.*
Bledsoe, 2003, Critical Reviews in Food Science and Nutrition, 43: 317-356.*
English Translation of FR2096704.*
Taranger et al., "Induction of Dedifferentiation, Genome-wide Transcriptional Programming, and Epigenetic Reprogramming by Extracts of Carcinoma and Embryonic Stem Cells" Mol Biol Cell. (2005) pp. 5719-5735.
Menard et al., "Transplantation of cardiac-committed mouse embryonic stem cells to infarcted sheep myocardium: a preclinical study" Lancet, (2005) 366(9490)1005-12.
Goldman "Stem and progenitor cell-based therapy of the human central nervous system" Nat Biotechnol. (2005) 23(7):862-71.
Leri et al., "Repair of the damaged heart" Kidney Int. (2005) 68(5):1962.
Levy et al., "Embryonic and adult stem cells as a source for cell therapy in Parkinson's disease" J Mol Neurosci. (2004) 24(3):353-86.

(Continued)

Primary Examiner — Valarie Bertoglio
(74) Attorney, Agent, or Firm — Casimir Jones SC

(57) ABSTRACT

The invention describes methods and agents for improving cosmetic appearance, for promoting, improving or restoring health of cells and tissues, preferably skin, and more preferably, for restoring aged or damaged skin to a healthy appearance. In some embodiments, the invention relates to compositions of cells, eggs, cell extracts, egg extracts, and extract components such as purified nucleic acids, polypeptides, lipids, carbohydrates or other natural products.

16 Claims, 4 Drawing Sheets

OTHER PUBLICATIONS

Jack et al., "Processed lipoaspirate cells for tissue engineering of the lower urinary tract: implications for the treatment of stress urinary incontinence and bladder reconstruction" J Urol. (2005) 174(5):2041-5.

Kitmaura et al., Establishment of renal stem/progenitor-like cell line from S3 segment of proximal tubules in adult rat kidney Kidney Int. (2005) 68(5):1966.

Matzinger "The Danger Model: A Renewed Sense of Self" Science (2002) 296:301-305.

Amoh et al., "Multipotent nestin-positive, keratin-negative hair-follicle bulge stem cells can form neurons" Proc Natl Acad Sci U S A. (2005) 12;102(15):5530-4.

Kocher, et al., "Neovascularization of ischemic myocardium by human bone-marrow-derived angioblasts prevents cardiomyocyte apoptosis, reduces remodeling and improves cardiac function" Nat. Med. (2001) 7, 430-436.

Evans, et al., "Derivation and Preliminary Characterization of Pluripotent Cell Lines From Porcine and Bovine Blastocysts," Theriogenology (1990) 33(1):125-128.

Notarianni, et al., "Maintenance and differentiation in culture of pluripotential embryonic cell lines from pig blastocysts," J. Reprod. Fertil. (1990) 41(Suppl.):51-56.

Giles, et al., "Pluripotency of Cultured Rabbit Inner Cell Mass Cells Detected by Isozyme Analysis and Eye Pigmentation of Fetuses Following Injection Into Blastocysts or Morulae," Mol. Reprod. Dev. (1993) 36:130-138.

Graves, et al., "Derivation and Characterization of Putative Pluripotential Embryonic Stem Cells From Preimplantation Rabbit Embryos," Mol. Reprod. Dev. (1993) 36:424-433.

Sukoyan, et al., Isolation and Cultivation of Blastocyst-Derived Stem Cell Lines From American Mink (Mustela vison) Mol. Reprod. Dev. (1992) 33:418-431.

Sukoyan, et al., "Embryonic Stem Cells Derived From Morulae, Inner Cell Mass, and Blastocysts of Mink: Comparisons.of Their Pluripotencies," Mol. Reprod. Dev. (1993) 36:148-158.

Iannaccone, et al., "Pluripotent Embryonic Stem Cells from the Rat are Capable of Producing Chimeras," Dev. Biol. (1994) 163:288-292.

Evans et al, "Establishment in culture of pluripotential cells from mouse embryos," Nature (1981) 292:154-156.

Martin, "Isolation of a pluripotent cell line from early mouse embryos cultured in medium conditioned by teratocarcinoma stem cells," Proc Natl Acad Sci USA (1981) 78:7634-7638.

Doetschmanet al. "Establishment of Hamster Blastocyst-Derived Embryonic Stem (ES) Cells," Dev Biol (1988) 127:224-227.

Bradley, et al., "Formation of germ-line chimaeras from embryo-derived teratocarcinoma cell lines," Nature (1984) 309:255-256.

English Translation of Abstract; Publication No. FR2500305; Published: Aug. 27, 1982; Applicant: Alvaro Mancori; (1 pg.).

English Translation of Abstract; Publication No. CN1343496 Published: Apr. 10, 2002; Applicant: Shenyang Farmacology University; (1 pg.).

English Translation of Abstract; Publication No. FR2827171 (A1); Published: Jan. 17, 2003; Applicant: SOC Extraction Principes ACTIF; (1 pg.).

English Translation of Abstract; Publication No. FR2843123 (A1); Published: Feb. 6, 2004. Applicant: Saint Laurent Parfums, et al.; (2 pgs.).

English Translation of Abstract; Publication No. RU2232587 (C1); Published: Jul. 20, 2004; Applicant: MIRRA-M Stock Co.; (2 pgs.).

English Translation of Abstract; Publication No. JP08169837; Published: Jul. 2, 1996; Applicant: Shimizu Eiko; (1 pg.).

English Translation of Abstract; Publication No. RU2110984 (C1); Published: May 20, 1998; Applicant: Biocomestic WKS Stock Co.; (1 pg.).

English Translation of Abstract; Publication No. DE199117532 (A1); Published: Oct. 26, 2000; Applicant: Christian Toloczyki; (1 pg.).

English Translation of Abstract; Publication No. DE10001740 (A1); Published: Jul. 26, 2001; Applicant: Jeannette Backhaus; (1 pg.).

Gottschalck, T.E., et al.; "International Cosmetic Ingredient Dictionary and Handbook"; The Cosmetic, Toiletry and Fragrance Association, Washington, D.C., (2004); 10th Edition, vol. 3; pp. 2041-2042.

* cited by examiner

ADMINISTRATION OF CELLS AND CELLULAR EXTRACTS FOR REJUVENATION

The present application claims priority to Provisional Application Ser. No. 60/799,560, filed May 11, 2006.

FIELD OF THE INVENTION

The invention relates to improving visible parts of a person contributing to cosmetic appearance directly or indirectly, including but not limited to skin, hair, subcutaneous fat, cartilage, muscle, skeletal structures, and to improving health and damage of cells and tissues preferably skin, and more preferably restoring aged skin to a youthful appearance. In some embodiments, the invention relates to a composition comprising i) differentiable cells, ii) extracts from cells or eggs or iii) components thereof, which can induce differentiation and extract components purified or synthetic nucleic acid sequences, polypeptides, or natural products contained in the extracts. In some embodiments, the cells are differentiable cells, preferably stem cells. In some embodiments, the compositions are used in a method that comprises application of compositions to skin and/or wounds after removal the outer surface layers. In some embodiments, the invention relates to a method of de-differentiation of cells and/or de-differentiation followed by re-differentiation. In some embodiments, the invention relates to managing, preventing, and treating skin diseases.

This invention also relates to the use of compositions comprising differentiable cells, egg cellular extracts or differentiable cell cellular extracts to prevent deterioration, damage and malfunction of cells and tissues, and to promote, improve and exceed cellular function in order to promote, improve and exceed appearance, vitality and health of cells and tissues.

BACKGROUND OF THE INVENTION

Skin is the first barrier we have against outside aggressions, and carries out both physical and chemical defenses. Vitamin D is produced in the epidermis under the effects addition, skin cells may become damaged by physical means, i.e., wounded, or damaged due to age. Thus, there is a need to identify compositions and methods for managing and improving skin health and preventing and treating skin conditions, and diseases, and maintaining normal skin appearance and restoring aged skin to a youthful appearance.

When a wound heals, a scar takes its place. Simple tissues such as fat, connective tissue, and epithelium regenerate, but the skin, being a complex organ derived from 2 germ layers, heals by the formation of a predominantly fibrous tissue. If the injury sections or destroys the papillary layer of the stratum corneum, a scar will be formed. Sometimes, this scar is inconspicuous; other times, it may be disfiguring. The most common presenting concern of patients with abnormal scars is disfigurement. However, some patients experience other symptoms in association with their abnormal scar, such as pain, pruritus, and loss of motion. These other symptoms can be indications for surgical correction of the scar. Thus, there is a need to identify compositions and methods of managing, preventing, and treating scars.

After damage, surgery or radiation of tissues or organs, scarring and incomplete regeneration of the tissue or organ occurs. This causes pain and discomfort as well as compromised function of the damaged tissues or organs. Generally, adult humans are unable to completely heal and regrow organs and tissues, while e.g. amphibians can regrow tissues including lost limbs. Thus, there is a need to identify compositions and methods of managing and treating scarring in internal organs and tissues, increasing tissue plasticity and stimulate regrowth of damaged tissues and organs.

SUMMARY OF THE INVENTION

The invention relates to improving visible parts of a person contributing to cosmetic appearance directly or indirectly, including but not limited to skin, hair, subcutaneous fat, cartilage, muscle, skeletal structures, and to improve health and damage of cells and tissues preferably skin, and more preferably restoring aged skin to a youthful appearance. In some embodiments, the invention relates to compositions of cells, cell or egg extracts, and extract components which can induce de-differentiation, including but not limited to purified or synthetic nucleic acid sequences, polypeptides, or natural products contained in the extracts. In some embodiments, the cells are differentiable cells, preferably stem cells. In some embodiments, the compositions are used in a method that comprises application of the compositions to skin and/or wounds after removal the outer surface layers. In some embodiments, the invention relates to a method of de-differentiation of cells and/or de-differentiation followed by re-differentiation. In some embodiments, the invention relates to managing, preventing, and treating skin diseases. In some embodiments, the invention relates to repair or de novo formation of lost or damaged tissues, organs and limbs.

In some embodiments, the invention relates to a composition comprising i) a cellular component comprising differentiable cells, differentiable cell cellular extracts, egg cellular extracts or components of differentiable cell extracts or egg cellular extracts or combinations thereof and ii) lipids. In further embodiments, the composition further comprises purified or synthetic nucleic acid sequences, proteins, epigenetic inhibitors, or natural products contained in the extracts or combinations thereof. In further embodiments, the differentiable cells are embryonic stem cells, embryonic germ cells, or adult stem cells. The present invention is not limited to the use of any particular cellular extract or fraction. Indeed, the use of a variety of cellular extract and fractions is contemplated, including, but not limited to, cytoplasmic extracts and fractions, nuclear extracts and fractions, water soluble extracts and fractions, and extracts and fractions prepared from cellular extracts by affinity chromatography, gradient centrifugation, HPLC, size exclusion chromatography and the like.

In some embodiments, the invention provides methods and the compositions find use for prevention of deterioration, damage and malfunction of cells and tissues, and to promote, improve and exceed cellular function in order to promote, improve and exceed appearance, vitality and health of cells and tissues.

In some embodiments, the invention provides a skin healing composition comprising i) a cellular component selected from the group consisting of differentiable cells, differentiable cell cellular extracts and an egg cellular extract or combinations thereof and ii) a lipid component. In further embodiments, the synthetic protein is a fusion-trojan protein. In further embodiments, the composition further comprises natural vernix, vernix extracts, vernix made from synthetic components, and components of vernix extracts. In further embodiments, the lipid component comprises squalene, aliphatic waxes, sterol esters, diol esters, triglycerides, and free sterol. In further embodiments, the lipid component is derived from egg from fish, shrimp, sea urchin or frog and/or fish roe. In further embodiments, the lipid component contains cholesterol, fatty acids, and ceramides. In some embodiments, the lipid component is from a source different than the cellular component. In further embodiment, the composition contains keratin or flaggrin. In further embodiments, the composition further comprises glutamine, antiinfective agents, antioxidants and/or nicotinamide. In further embodiments, the antioxidant is vitamin E, A, or C or combinations thereof.

In some embodiments the invention provides a kit for improving the appearance of a scar comprising two compositions, wherein the first composition dissolves scar tissue and comprises collagen dissolving agents and the second composition improves wound healing and comprises a cellular component selected from the group consisting of differentiable cells, differentiable cell cellular extracts and an egg cellular extract or combinations thereof, lipids, proteins, and water. In further embodiments, the differentiable cells are embryonic stem cells, embryonic germ cells, or adult stem cells. In further embodiments, the first composition further comprises an antiseptic, an antibacterial, an anti-inflammatory, an immunomodulator, a protease, or an analgesics or combinations thereof. In further embodiments, the second composition further comprises natural vernix, vernix extracts, vernix made from synthetic substances, and components of vernix extracts. In further embodiments the lipid component comprises squalene, aliphatic waxes, sterol esters, diol esters, triglycerides, free sterols or combinations thereof. In further embodiments, the lipids and/or proteins are derived from eggs from fish, shrimp, sea urchin or frog and/or fish roe. In further embodiments, the lipid fraction contains cholesterol, fatty acids, or ceramides or a combination thereof. In some embodiments, the lipid component is from a different source than the cellular component. In further embodiments, the composition further comprises glutamine, antiinfective agents, antioxidants and/or nicotinamide.

In some embodiments, the invention provides methods for improving the appearance of a skin comprising: i) removing skin tissue by chemicals, a laser, or physical force and ii) applying a composition that improves wound healing comprising differentiable cells, differentiable cell or egg cellular extracts, components of differentiable cell extracts, lipids, proteins, and/or water. In further embodiments, improving the appearance of skin includes improving the appearance of a scar or improving the appearance of skin with wrinkles. In further embodiments, the differentiable cells are embryonic stem cells, embryonic germ cells, or adult stem cells. In further embodiments, the composition further comprises natural vernix, vernix extracts, vernix made from synthetic substances, and components of vernix extracts.

In additional embodiments, the invention provides methods for the topical administration of differentiable cells, egg or differentiable cell cellular extracts, components of cell extracts comprising: providing a composition comprising a cellular component comprising differentiable cells, egg or differentiable cell cellular extracts, components of cell extracts and a subject having skin and applying the extracts to the skin of the subject. In further embodiments, the egg or differentiable cellular extracts or components of cell extracts are effective as a nutrient to a cell of the skin. In further embodiments, the composition is a water-based gel. In further embodiments, the water-based gel comprises a compound selected from the group consisting of hyaluronic acid and chitosan. In further embodiments the composition is a component on a wound dressing. In further embodiments the composition is a component in a spray composition. In further embodiments the spray composition is an aerosol. In further embodiments, the spray composition dries on the skin. In further embodiments, the spray composition comprises gel-forming components. In some embodiments, the composition further comprises a lipid component as described above.

In some embodiments, the invention provides a wound healing dressing comprising a composition comprising differentiable cells, egg or differentiable cell cellular extracts, and components of cell extracts.

In additional embodiments, the invention provides methods for the topical administration of differentiable cells, cell extracts, components of cell extracts comprising: i) providing a) a composition containing differentiable cells, differentiable cell or egg cellular extracts, components of cell extracts, b) a subject having a wound in skin and c) wound dressing ii) applying the differentiable cells, cell extracts, components of cell extracts to the wound; and iii) covering the wound with the wound dressing. In further embodiments, the wound dressing is non-occlusive. In further embodiments, the wound dressing is plaster. In further embodiments, the wound dressing comprises: i) a waterproof layer; ii) a nutrient gel layer comprising differentiable cells, cell extracts, and components of cell extracts. In further embodiments, the waterproof layer is a plastic membrane that can be glued onto skin. In further embodiments, the nutrient gel layer comprises antibacterial agents and collagen modulating substances. In further embodiments, the nutrient gel layer improves the speed of wound healing.

In some embodiments, the invention provides methods for the topical administration of differentiable cells, egg or differentiable cell cellular extracts, or components of cell extracts comprising: i) providing a) a subject having 1) a wound in skin and 2) a tissue comprising specialized cells b) wound dressing; ii) harvesting the specialized cells from the tissue; iii) culturing the specialized cells under conditions such that a composition comprising the cultured specialized differentiable cells, cell extracts, or components of cell extracts is formed; iii) applying the composition to the wound; and iii) covering the wound with the wound dressing. In further embodiments, the specialized cells selected from the group consisting of a bulge hair-follicle stem cell, an embryonic stem, or germ stem cell. In further embodiments, the composition is a fluid suspension of specialized cells. In further embodiments, the composition is a plaster. In further embodiments, the composition is placed on a membrane with a nutrient gel layer prior to applying the composition to the wound. In further embodiments, the membrane is plastic functioning as an occlusive wound dressing when applied to the skin. In further embodiments, the wound dressing is a commercial band-aid. In further embodiments, prior to applying the composition a step of burning skin is performed, freezing skin is performed, and/or sanding skin is performed. In further embodiments, prior to applying the composition a transport vehicle which penetrate intact skin is applied to the composition or skin comprising a phospholipids, palmitylmyristrates, DMSO, polymer or chitosan suspensions or matrix, liposomes and/or trojan peptides, chariot peptides (nature biotech 2000), small elastic vesicles (Van den Bergh et al., 1999), microspheres, nanoparticles, preloaded spherical beads, uni- and/or multilamellar vesicles, retinol molecular film, poly acrylo nitrile, beta-glucan (Redmond, Int Journ Cosmetic Science 2005), propylene glycol, butylenes glycol, polyethylene glycol, olive oil, dimethyl isosorbate, dimethylformamide, methyl salicylate, long chain oleic acids.

In some embodiments, the invention provides compositions for stimulating cells such as fibroblasts and keratinocytes comprising an effective amount of a purified cytoplasmic fraction of an embryonic stem cell, progenitor cell, somatic cell or eggs from animals, including but not limited to primates, rodents, fish, shrimp, sea urchin and/or frog egg. In further embodiments, the composition further comprises fats, proteins and/or natural products. In further embodiments, the composition further comprises an herbal substance. In further embodiments, the herbal substance is aloe vera. In further embodiments, the composition further comprises seed extracts. In further embodiments, the seed extracts are obtained from wheat, corn, rice, or avocado. In further embodiments, the composition further comprises a plant oil. In further embodiments, the composition further comprises a fungal substance. In further embodiments, the fungal substance is nepal fungus. In further embodiments, the composition further comprises fish, shrimp, sea urchin, or frog egg extracts, or components of these egg extracts. In further embodiments the components of egg extracts are glycosylation breakers and inhibitors. In further embodiments, the components of egg extracts are glycosylation breakers and inhibitors are aminoguanidine, carnosine, and fex pyridoxamine.

In additional embodiments, the invention provides methods of wound healing comprising providing a subject having a wound and a composition comprising differentiable cells, differentiable cell or egg cellular extracts, egg extracts, components of cell extracts or egg extracts and applying the composition to the wound under conditions such that the wound is healed. In further embodiments, the composition further comprises a collagen dissolving agent. In further embodiments, the collagen dissolving agent is an acid. In further embodiments, the composition further comprises a fruit acid. In further embodiments the composition is a cream. In further embodiments, the wound is an open wound and applying the composition topically. In preferred embodiments, the method further comprises providing a support matrix wherein, the support matrix comprises the composition. In further embodiments, the support matrix is a fabric or plastic wound dressing.

In some embodiments, the invention provides methods of skin regeneration comprising providing a subject having a wound and a composition comprising differentiable cells, differentiable cell or egg cellular extracts, or components of cell extracts or egg extracts and applying the composition to the wound under conditions that such skin is regenerated. In further embodiments the composition is a cream. In further embodiments, the wound is an open wound and applying the composition is topically.

In additional embodiments, the invention relates to a method of skin rejuvenation comprising providing a subject having an uneven skin and a composition comprising differentiable cells, differentiable cell or egg cellular extracts, egg extracts, or a component of a cellular extract and applying the composition to the uneven skin under conditions that such skin is rejuvenated. In some embodiments, the component of a cell extract is a nucleic acid sequence or the component of a cell extract is a peptide or combinations thereof. In some embodiments, the uneven skin is a result of a scar or wrinkles. In further embodiments, the composition is in a cream. In further embodiments the cream further comprises permeabilizing agents. In further embodiments, the permeabilizing agent is a toxic agent, DMSO or chitosan, chitosan polymer, or trypsin. In further embodiments, the permeabilizing agent is liposomes or alginate beads. In further embodiments, the liposomes or alginate beads comprise a peptide or a nucleic acid sequence of a cell extract or growth factor or a combination thereof. In further embodiments, the liposome comprises nucleic acid sequence of cell extracts or egg extracts generated by electroporation. In further embodiments, the composition comprises a fusion trojan peptide comprising a peptide of the cell extract. In further embodiments, applying the composition is topical. In additional embodiments, the method further comprises the step of applying the composition is executed after applying a chemical, laser, or physical force to the uneven skin under conditions that a outer lay of cells of the uneven skin are removed. In further embodiments, the composition further comprises an antiseptic, an antibacterial, an anti-inflammatory, an immunomodulator, a protease, or an analgesics or combinations thereof.

In some embodiments, the invention relates to a composition comprising: a lipid; a composition of plant seed components; an antioxidant; a purified or synthetic protein, or a purified or synthetic natural product contained in a cellular extract; a stabilizing component; autologous fat derived from adipose tissue of a subject.

In additional embodiments, the invention provides methods of improving a skin graft comprising grafting skin or skin substitute and applying a composition comprising: differentiable cells, differentiable cell or egg cellular extracts, egg extracts; components of cell extracts or egg extracts; a purified or synthetic nucleic acid sequence, a purified or synthetic protein, or a purified or synthetic natural product contain in cell extracts, egg extracts; or combinations thereof.

In some embodiments, the invention provides methods for managing, treating, and/or preventing scarring, abnormal scars, abnormal wound healing, widened scar, hypertrophied scar, keloid, keloid scar, wound-healing complications, cicatrix, scar hypertrophy by administering in a prophylactic or non-prophylactic manner using compositions disclosed herein. In further embodiments, the invention provides methods for primary healing, wound closure, secondary healing, epithelialization, re-epithelialization, tertiary wound closure, delayed primary closure, debridement, suture, inflammatory phase, proliferative phase, maturational phase, hemostasis, inflammation, collagen, clotting, thromboxane A2, prostaglandin 2a, prostaglandin 2-alpha, vasoconstrictor, hemorrhage, vasodilatation, histamine, platelet, chemokine, epidermal growth factor, fibronectin, fibrinogen, histamine, platelet derived growth factor, serotonin, von Willebrand factor, clot formation, platelet degranulation, complement cascade, neutrophil, leukocyte, macrophage, monocyte, collagenase, interleukin, tumor necrosis factor, fibroblasts, transforming growth factor, keratinocyte, angiogenesis, granulation tissue formation, collagen deposition, and insulin-like growth factor.

In some embodiments, the invention provides compositions comprising differentiable cells, preferably embryonic stem cells or precursor cells. In further embodiments, the compositions comprises the extracts of differentiable cells, preferably embryonic stem cells or precursor cells. In additional embodiments, the compositions contain components of extracts from differentiable cells, preferably embryonic stem cells or precursor cells.

In some embodiments the invention provides compositions containing differentiable cells, preferably embryonic stem cells or precursor cells, the extracts of differentiable cells, preferably embryonic stem cells or precursor cells, components of extracts from differentiable cells, and/or natural vemix and/or vemix extracts and/or vemix components of vemix extracts that partially or totally synthetic.

In some embodiments, the invention provides methods for the topical administration of egg cellular extracts or differentiable cell cellular extracts comprising: providing a composition containing egg cellular extracts or differentiable cell cellular extracts and a subject having skin and applying the extracts to the skin. Preferably a nutritional signal in the extract reaches and is effective as a nutrient to the skin cells. Preferably the composition is in a water based gel comprising hyaluronic acid and/or chitosan. In another preferred embodiment, the extract is a spray acting as a liquid band-aid or fluid that dries on the skin. In further embodiments, the liquid contains gel-forming components such as collagen and chitosan. In further preferred embodiments, the composition is a component of a film on a support or cream.

The present invention also provides for use of the foregoing compositions for the treatment of skin, for removing wrinkles, for rejuvenation of skin, for wound healing, for improving the appearance of skin, the prevent damage to skin, to prevent deterioration of skin, or to provides nutrients to skin and any other use described herein.

The present invention further provides methods for preparing a composition for topical application to the skin comprising: providing differentiable cells or preparing an extract or fraction of differentiable cells or eggs; and formulating said differentiable cells or said extract with an agent for topical administration to the skin to provide a cream, gel, spray, emulsion, solid, plastic or matrix, ointment, powder or lotion suitable for topical administration. In further embodiments, the present invention provides compositions made by the foregoing methods.

DEFINITIONS

Figure 1:
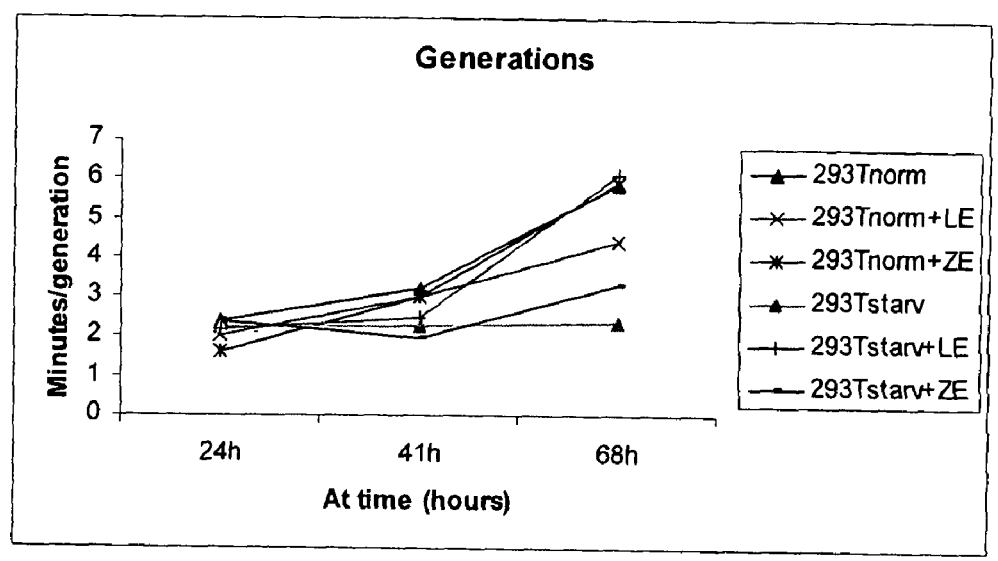
FIG. 1 is a graph of generations over time.

"Anti-infective agents" include, but are not limited to benzylpenicillin, penicillin, enicillin G, 6-phenyl acetyl penicillin, peniclin V, micronomicin, clavulanate, oxacillin, dequalinium, cloxacillin, sulbenicillin, ampicillin, cilleral, and principen and combinations thereof.

"Anti-inflammatory" means a substance that reduces inflammation. Many analgesics remedy pain by reducing inflammation. Many steroids—specifically glucocorticoids—reduce inflammation by binding to cortisol receptors. Non-steroidal anti-inflammatory drugs (NSAIDs) alleviate pain by counteracting the cyclooxygenase (COX) enzyme. On its own COX enzyme synthesizes prostaglandins, creating inflammation. Many herbs have anti-inflammatory qualities, including but not limited to hyssop and willow bark (the latter of which contains salicylic acid, the active ingredient in aspirin), as well as birch, licorice, wild yam and ginseng.

"Antioxidants" means any of a variety of substances that prevent or slow the breakdown of another substance by oxygen. Synthetic and natural antioxidants are used to slow the deterioration of gasoline and rubber, and such antioxidants as vitamin C (ascorbic acid), butylated hydroxytoluene (BHT), and butylated hydroxyanisole (BHA) are typically added to foods to prevent them from becoming rancid or from discoloring. Nutrients such as beta-carotene (a vitamin A precursor), vitamin C, vitamin E, and selenium have been found to act as antioxidants. They act by scavenging free radicals, molecules with one or more unpaired electrons, which rapidly react with other molecules, starting chain reactions in a process called oxidation. Free radicals are a normal product of metabolism; the body produces its own antioxidants (e.g., the enzyme superoxide dismutase) to keep them in balance. However, stress, aging, and environmental sources such as polluted air and cigarette smoke can add to the number of free radicals in the body, creating an imbalance. The highly reactive free radicals can damage healthy DNA and have been linked to changes that accompany aging (such as age-related macular degeneration, a leading cause of blindness in older people) and with disease processes that lead to cancer, heart disease, and stroke.

An "antiseptic" is a substance that kills or prevents the growth and reproduction of various microorganisms, including bacteria, fungi, protozoa, and viruses on the external surfaces of the body. The objective of antiseptics is to reduce the possibility of sepsis, infection or putrefaction by germs. Antibacterials have the same objective but only act against bacteria. Antibiotics perform a similar function, preventing the growth or reproduction of bacteria within the body. Antiseptics include, but are not limited to, alcohol, iodine, hydrogen peroxide, and boric acid. There is great variation in the ability of antiseptics to destroy microorganisms and in their effect on living tissue. For example, mercuric chloride is a powerful antiseptic, but it irritates delicate tissue. In contrast, silver nitrate kills fewer germs but can be used on the delicate tissues of the eyes and throat. There is also a great difference in the time required for different antiseptics to work. Iodine, one of the fastest-working antiseptics, kills bacteria within 30 sec. Other antiseptics have slower, more residual action. Since so much variability exists, systems have been devised for measuring the action of an antiseptic against certain standards. The bacteriostatic action of an antiseptic compared to that of phenol (under the same conditions and against the same microorganism) is known as its phenol coefficient.

"Chitosan" is a beta-1,4-linked glucosamine polymer which, unlike chitin, contains few, if any, N-acetyl residues. It may be obtained from chitin, a polysaccharide found in the exoskeletons of crustaceans such as shrimp, lobster, and crabs. The shells may be ground into a pulverous powder. This powder is then deacetylated which allows the chitosan to absorb lipids.

"Collagen" means any of a variety of substances that contains the alpha chains of the collagen polypeptide with a sequence that generally follows the pattern Gly-X-Y, where Gly for glycine, X for proline, and Y for proline or hydroxyproline. Collagen proteins also contain significant amounts of glycine and proline. Hydroxyproline and hydroxylysine are not inserted directly by ribosomes. They are derivatised from proline and lysine in enzymatic processes of post-translational modification, for which vitamin C is required. This is related to why vitamin C deficiencies can cause scurvy, a disease that leads to loss of teeth and easy bruising caused by a reduction in strength of connective tissue due to, a lack of collagen, or defective collagen. Cells called fibroblasts form the various fibers in connective tissue in the body including collagen. The white collagen that makes up the matrix of most connective tissue in mammals consists of inter-woven fibres of the protein collagen. The collagen fibers consist of globular units of the collagen sub-unit, tropocollagen. Tropocollagen sub-units spontaneously arrange themselves under physiological conditions into staggered array structures stabilized by numerous hydrogen and covalent bonds. Tropocollagen sub-units are left-handed triple helices where each strand is, further, a right-handed helix itself. Thus, tropocollagen may be considered to be a coiled coil.

Although collagen is responsible for skin elasticity, and its degradation leads to wrinkles that accompany aging, it occurs in many other places throughout the body, and in different forms known as types: Type I collagen—This is the most abundant collagen of the human body present in scar tissue, the end product when tissue heals by repair; Type II collagen—Auricular cartilage Type III collagen—This is the collagen of granulation tissue, and is produced quickly by young fibroblasts before the tougher type I collagen is synthesized; Type IV collagen-Basal lamina; Type V collagen—most interstitial tissue, assoc. with type I; Type VI collagen—most interstitial tissue, assoc. with type I; Type VII collagen—epithelia; Type VIII collagen—some endothelial cells; Type IX collagen—cartilage, assoc. with type II; Type X collagen—hypertrophic and mineralizing cartilage; Type XI collagen—cartilage; Type XII collagen—interacts with types I and III.

With in the context of certain embodiments, "collagen modulating substances" means a variety of substances capable of facilitating the formation or breaking down of units or of any type of collagen.

A "gel" is a semisolid material formed from a colloidal solution. By weight, gels are mostly liquid, yet they behave like solids. An example is gelatin.

"Keratin" is any of a variety of fibrous protein molecules that serve as structural units for various living tissues. The keratins are the major protein components of hair, wool, nails, horn, hoofs, and the quills of feathers. These proteins generally contain large quantities of the sulfur-containing amino acids, particularly cysteine. The helical keratin molecules twist around each other to form elongated strands called intermediate filaments. The formation of a disulfide bridge between the sulfur atoms on two cysteines on separate polypeptide chains of keratin allows for the cross-linkage of these chains and results in a fairly rigid aggregate.

"Filaggrin" is any of a variety of filament-associated proteins that interact with keratin intermediate filaments of terminally differentiating mammalian epidermis via disulphide bond formation.

"Immunomodulator" means any of a variety of substance that influences the immune system. Examples include, but are not limited to, cytokines, Interleukin-2, immunostimulants, and immunosuppressors.

The term "natural product" means any of a variety of organic chemical moieties whose molecular arrangement is derived from enzymatic transformations in a living organism excluding amino acids, proteins, polypeptides, nucleic acids and sequences, and saturated fatty acids. Examples include, but are not limited to lipids (i.e., that are not saturated fatty acids), carbohydrates/saccharides and polysaccharides, the steroids and their derivatives, the terpenes and their derivatives, vitamins, carotenoids, and natural medicines such as taxol, etc. The term "synthetic natural product" is a natural product not obtained from its natural source.

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

"Nucleoside," as used herein, refers to a compound consisting of a purine [guanine (G) or adenine (A)] or pyrimidine [thymine (T), uridine (U), or cytidine (C)] base covalently linked to a pentose, whereas "nucleotide" refers to a nucleoside phosphorylated at one of its pentose hydroxyl groups.

"Nucleic acid sequence" as used herein refers to an oligonucleotide, nucleotide or polynucleotide, and fragments or portions thereof, and to DNA or RNA of genomic or synthetic origin that may be single- or double-stranded, and represent the sense or antisense strand.

An "amino acid sequence" as used herein refers to a peptide or protein sequence.

A "peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al. (1993) Anticancer Drug Des., 8:53-63).

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

As used herein the term "portion" in reference to an amino acid sequence or a protein (as in "a portion of an amino acid sequence") refers to fragments of that protein. The fragments may range in size from four amino acid residues to the entire amino acid sequence minus one amino acid.

As used herein, the term "purified" refers to molecules, including but not limited to nucleic, ribonucleic, lipid or amino acid sequences, which are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

"Cancer" means any of various cellular diseases with malignant neoplasms characterized by the proliferation of anaplastic cells. It is not intended that the diseased cells must actually invade surrounding tissue and metastasize to new body sites. Cancer can involve any tissue of the body and have many different forms in each body area. Most cancers are named for the type of cell or organ in which they start.

"Cell" means the smallest structural unit of living matter capable of functioning autonomously, consisting of one or more nuclei, cytoplasm, and various organelles, all surrounded by a semipermeable membrane. Cells include all somatic cells obtained or derived from a living or deceased animal body at any stage of development as well as germ cells, including sperm and eggs (animal reproductive body consisting of an ovum or embryo together with nutritive and protective envelopes). Included are both general categories of cells: prokaryotes and eukaryotes. The cells contemplated for use in this invention include all types of cells from all organisms in all kingdoms: plans, animals, protists, fungi, archaebacteria and eubacteria. Stem cells are cells capable, by successive divisions, of producing specialized cells on many different levels. For example, hematopoietic stem cells produce both red blood cells and white blood cells. From conception until death, humans contain stem cells, but in adults their power to differentiate is reduced.

As used herein, the term "differentiation" related to cells means the process by which cells becomes structurally and functionally specialized, which is a progressive restriction of the developmental potential and increasing specialization of function which takes place during the development of the embryo and leads to the formation of specialized cells, tissues, and organs.

The term "dedifferentiation" related to cells means the reverse process of differentiation, where cells become less structurally and functionally specialized, which increases the developmental potential of the cell.

"Differentiable" means the ability of a cell to differentiate into a desired cell type. As used herein, the term "differentiates" means specialization (differentiation) or return to a more primitive cell type; dedifferentiation).

An "extract" as used in the context of "cell extract" and "egg extract" in this invention means a preparation of any type of cell as defined above obtained by chemical or mechanical action, as by pressure, distillation, evaporation etc. Extracts can include all or any single component or combination of components of the cells, including concentrated preparations of the active components. Such components of the extracts include but are not limited to RNA, DNA, lipids, all amino acid base structures including peptides and proteins, carbohydrates or combinations thereof. Extracts contemplated by this invention include but are not limited to extracts of fish eggs, urchin eggs, frog eggs, adult stem cells, plant seeds and plant stem cells.

"Growth media" are compositions used to grow microorganisms or cells in culture. There are different sorts of media for growing different sorts of cells. The biggest difference in growth media are between those used for growing cells in culture (cell culture uses specific cell types derived from plants or animals) and those used for growing microorganisms (usually bacteria or yeast). These differences arise due to the fact that cells derived from whole organisms and grown in culture are often incapable of growth without the provision of certain requirements, such as hormones or growth factors which usually occur in vivo. In the case of animal cells these requirements are often provided by the addition of blood serum to the medium. These media are often red or pink due to the inclusion of pH indicators. Growth media for embryonic stem cells preferably contains minimal essential medium, i.e., Eagle's: amino acids, salts (Ferric nitrate nonahydrate, Potassium chloride, Magnesium sulfate, Sodium chloride, Sodium dihydrogen phosphate), vitamins, (Ascorbic acid, Folic acid, Nicotinamide, Riboflavin, B-12) or Dulbecco's: additionally iron, glucose; non-essential amino acids, sodium pyruvate, β-mercaptoethanol, L-glutamine, fetal bovine serum and Leukemia Inhibitory Factor (LIF). In the case of microorganisms, there are no such limitations as they are often single cell organisms. One other major difference is that animal cells in culture are often grown on a flat surface to which they attach, and the medium is provided in a liquid form, which covers the cells. Bacteria such as *Escherichia coli* (*E. coli*, the most commonly used microbe in laboratories) may be grown on solid media or in liquid media, liquid nutrient medium is commonly called nutrient broth. The preferred growth media for microorganisms are nutrient broth or Luria-Bertani medium (L-B medium). Bacteria grown in liquid cultures often form colloidal suspensions. When agar (a substance which sets into a gel) is added to a liquid medium it can be poured into Petri dishes where it will solidify (these are called agar plates) and provide a solid medium on which microbes may be cultured.

Within the context of certain embodiments, "to glue to skin" means to stick or fasten to with or as if with any of various adhesives, such as, glue, paste or mucilage.

A "lipid" means any of a group of organic compounds, including the fats, oils, waxes, sterols, and triglycerides that are insoluble in water but soluble in nonpolar organic solvents, and are oily to the touch. Major classes of lipids include the fatty acids, the glycerol-derived lipids (including the fats and oils and the phospholipids), the sphingosine-derived lipids (including the ceramides, cerebrosides, gangliosides, and sphingomyelins), the steroids and their derivatives, the terpenes and their derivatives, certain aromatic compounds, and long-chain alcohols and waxes. In living organisms lipids serve as the basis of cell membranes and as a form of fuel storage. Often lipids are found conjugated with proteins or carbohydrates, and the resulting substances are known as lipoproteins and lipopolysaccharides. The fat-soluble vitamins can be classified as lipids. Liposomes are spherical vesicles formed by mixing lipids with water or water solutions. They have found applications in the oral administration of some drugs (e.g., insulin and some cancer drugs), since they retain their integrity until they are broken down by the lipases in the stomach and small intestine.

Within the context of certain embodiment, a "nutrient gel layer" a gel comprising substances typically contained in a growth medium.

Within the context of certain embodiments, "specialized cell" of a subject means that the cell has characteristic immunoidenificative markers, such that differentiation of these cells and exposure to tissues of the subjects can be done under conditions such that immune system does not create antibodies to the differentiated cells. For example, when red blood cells carrying one or both A or B antigens are exposed to the corresponding antibodies, they agglutinate; that is, clump together. People usually have antibodies against those red cell antigens that they lack. Thus, specialized red blood cells of the subject would be those of the proper blood type. The cause of transplant rejection is recognition of foreign MHC antigens by T cells and activation of those T cells to become effector cytotoxic or helper T cells. T cell activation occurs in the case of vascularized grafts of nucleated cells expressing MHC Matching MHC Class I (especially HLA-B) and Class II HLA-DR alleles is more important for successful transplantation than matching other MHC antigens; and matching MHC is more important than matching minor histocompatibility antigens. Thus, specialized MHC presenting cells of the subject would be those presenting matching MHC alleles.

The term "manage" when used in connection with a disease or condition means to provide beneficial effects to a subject being administered with a prophylactic or therapeutic agent, which does not result in a cure of the disease. In certain embodiments, a subject is administered with one or more prophylactic or therapeutic agents to manage a disease so as to prevent the progression or worsening of the disease.

As used herein, the terms "prevent" and "preventing" include the prevention of the recurrence, spread or onset. It is not intended that the present invention be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, the present invention also contemplates treatment that merely reduces symptoms, and/or delays disease progression.

Within the context of certain embodiments, a "waterproof layer" means a material or fabric that is substantially impervious to water or a layer of a sealing agent to intended to prevent substantial penetration by water.

As used herein, the term "transport vehicle" includes substances capable of aiding penetration of intact skin or skin cells or other somatic cells. The term "transport vehicle" is used synonymously with the term "permeabilizing agents". Such transport vehicles include, but are not limited to: phospholipids, palmitylmyristyrates, DMSO, polymer or chitosan suspensions or matrix, liposomes, Trojan peptides, chariot peptides, small elastic vesicles, microspheres (functionalized vectors made from naturally derived materials such as collagen, glycosaminoglycans, chondroitin sulfate, chitosan or polysaccharides), nanoparticles (carries lipophilic substances and enhance bioavailability of the encapsulated material into skin), preloaded spherical beads and sponges, uni- and/or multilamellar vesicles (stabilize contents of extracts in cream base and help transport into skin), retinol molecular film fluid (thin uniform monolayer film that facilitates the transfer of actives through the stratum corneum), poly acrylo nitrile (polymers comprising a controlled release system that synchronizes the release of an active ingredient along with a fragrance as a sensory marker which conveys the efficacy of the product), beta-glucan (oat fiber which aids in penetration of the skin, (Redmond, Int. Journ. Cosmetic science 2005), propylene glycol (as drug carrier, work best with a mineral oil based cream/lotion etc), butylene glycol, polyethylene glycol, olive oil, dimethyl isosorbide, dimethylformamide, methyl salicylate (these all enhance absorption through skin), long chain oleic acids (disrupts the bilayer within the stratum corneum, vital for permeation of compositions in propylene glycol-based formulations), substances capable of adjusting pH, hydration and local metabolism in skin. Agents modifying these factors include a vehicle containing an active hydrophobic agent, de-ionization of active ingredients, increased hydration of the skin (water content of carrier solution/cream/medium), lactic acid (alters the pH).

As used herein, the term "NANOG" refers to a homeobox gene. NANOG is thought to be required for stem cells to multiply without limit while remaining able to make many different types of cells. The gene is a potential master gene that helps make embryonic stem cells grow in the laboratory, making stem cells immortal.

As used herein, the term "OCT4" refers to a gene that is not active in somatic cells, including adult stem cells, but is expressed in embryonic stem and germ cells. OCT4 is essential to maintain pluripotency of embryonic stem cells.

As used herein, the term "SOX2" refers to the sex determining region Y (SRY) box 2 protein coding gene. This intronless gene encodes a member of the SRY-related HMG-box (SOX) family of transcription factors involved in the regulation of embryonic development and in the determination of cell fate.

As used herein, the term "GAPDH" refers to the housekeeping gene glyceraldehydes-3-phosphate dehydrogenase. This gene is involved in basic functions needed for cell maintenance. Housekeeping genes are constitutively expressed.

DETAILED DESCRIPTION OF THE INVENTION

The invention relates to improving health and damage of cells and tissues preferably skin, and more preferably restoring aged or damaged skin to a youthful and healthy appearance. In some embodiments, the invention relates to compositions of cells, cell or egg extracts, and extract components which can induce differentiation, including but not limited to purified or synthetic nucleic acid sequences, polypeptides, or natural products contained in said extracts. In some embodiments, the cells are differentiable cells, preferably stem cells or eggs. In some preferred embodiments, the extracts are aqueous extracts. In some embodiments, the extracts are from a non-avian source. In some embodiments, compositions are used in a method that comprises application of compositions to skin and/or wounds after removal the outer surface layers. In some embodiments, the invention related to a method of dedifferentiation of cells and/or dedifferentiation followed by redifferentiation. In some embodiments, the invention relates to managing, preventing, and treating skin diseases.

Application of the composition to the desired surface may be prophylactic, so that the composition is applied to the skin or other surface before exposure to an agent occurs. Application of the composition may be curative, for example, to further protect a compromised skin surface or to provide a protectant surface during natural or mediated healing of an exposed skin surface. Application of the composition may be protective, for example, to protect a skin surface should exposure to the agent occur.

The present invention relates to the use of extracts or components of differentiable cells for topical application to surfaces of the body. Accordingly, the present invention provides methods and compositions for cosmetic and therapeutic uses. The present invention is not limited to the use of extracts or components of any particular type of differentiatable cell. Indeed, the use of variety of types of cells and differentiable cells from any organism is contemplated, including, but not limited to, mammalian embryonic stem cells, mammalian adult stem cells, cord blood cells, fish, shrimp or sea urchin eggs and embryos, and amphibian eggs and embryos.

In some embodiments, the invention relates to dedifferentiating existing epithelial/epidermal cells to a primordial state, wherein the cells have stem-cell capacities and can reform the correct and needed cells for the regeneration of the whole layer of skin (epidermis, dermis and subdermis). Although many differentiated cells are typically committed to their fate, dedifferentiation events can take place. Urodele amphibians and teleost fish can replace lost anatomical parts by a process of migration, dedifferentiation, proliferation and redifferentiation of epithelial cells in the wounded area. Functional reprogramming of differentiated cell nuclei has also been illustrated by the derivation of pluripotent embryonic stem cells (ESCs), and by the live birth of cloned animals after nuclear transplantation into unfertilized eggs.

The term plasticity, as used in this herein, means that a cell from one tissue can generate the differentiated cell types of another tissue. *Xenopus* eggs can reprogram mammalian somatic nuclei to express the POU family member homeodomain transcription factor gene Oct4 by a process requiring DNA demethylation. DNA demethylation also occurs after fusion of mouse thymocytes with embryonic germ cells (EGCs) but interestingly, only EG cells are capable of demethylating imprinted genes. Fusion of neuronal progenitor cells or bone marrow derived cells with ESCs results in hybrids which express markers of pluripotency. Similar results are obtained from fusing human fibroblasts with ESCs. Fusion of embryonal carcinoma cells (ESCs) with T-lymphoma cells also promotes the formation of colonies expressing pluripotent cell transcripts from the lymphoma genome. Components of pluripotent EG, ES or EC cells can elicit reprogramming events in a somatic genome.

Somatic nuclear function can be altered using nuclear and cytoplasmic extracts because extracts provide the necessary regulatory components. Extracts of regenerating newt limbs promote cell cycle reentry and downregulation of myogenic markers in differentiated myotubes. Teratocarcinomas are a particular type of germ cell tumors which contain undifferentiated stem cells and differentiated derivatives that can include endoderm, mesoderm and ectoderm germ layers. Undifferentiated carcinoma cells can be cultured to give rise to lines of ECCs. ECCs form malignant teratocarcinomas when transplanted into ectopic sites; however, some ECC lines can also contribute to tissues of the developing fetus when introduced into a blastocyst.

Undifferentiated human teratocarcinoma NCCIT cells can be established from a mediastinal mixed germ cell tumor. NCCIT is at a stage intermediate between a seminoma (a precursor of germ cell tumors) and an embryonal carcinoma. NCCIT is a developmentally pluripotent cell line that can differentiate into derivatives of all three embryonic germ layers and extraembryonic cell lineages an extract of undifferentiated somatic cells can elicit dedifferentiation in a somatic cell line. See Taranger et al., "Induction of Dedifferentiation, Genome-wide Transcriptional Programming, and Epigenetic Reprogramming by Extracts of Carcinoma and Embryonic Stem Cells" Mol Biol Cell. (2005).

Stem cells can establish in damaged tissue. See Menard et al., "Transplantation of cardiac-committed mouse embryonic stem cells to infarcted sheep myocardium: a preclinical study" Lancet, 366(9490):1005-12 (2005); Goldman "Stem and progenitor cell-based therapy of the human central nervous system" Nat. Biotechnol. 23(7):862-71 (2005); Leri et al., "Repair of the damaged heart" Kidney Int. 68(5):1962 (2005); Levy et al., "Embryonic and adult stem cells as a source for cell therapy in Parkinson's disease" J Mol. Neurosci. 24(3):353-86 (2004); Jack et al., "Processed lipoaspirate cells for tissue engineering of the lower urinary tract: implications for the treatment of stress urinary incontinence and bladder reconstruction" J. Urol. 174(5):2041-5 (2005); Kitmaura et al., Establishment of renal stem/progenitor-like cell line from S3 segment of proximal tubules in adult rat kidney Kidney Int. 68(5):1966 (2005).

In some embodiments, the invention relates to extracts that are capable of stimulating the immune system to aid in healing. For example, the extracts may contain fibrogen and heat shock proteins. These endogenous cellular components are alarm signals typically expressed in distressed or injured cells. They bind Toll-like receptors (TLRs) in antigen presenting cells (APCs) and put the immune system on alert of a damaged area. See Matzinger "The Danger Model: A Renewed Sense of Self" Science 296:301-305 (2002).

In some embodiments, the invention relates to stimulating existing stem cells in skin, such as stem cells found in and around hair follicles to duplicate and/or differentiate into epithelial cells or neurons. Nestin, a marker for neural progenitor cells, is expressed in cells of the hair-follicle bulge and behave as stem cells, differentiating to form much of the hair follicle during each hair growth cycle. The hair follicle is dynamic, cycling between growth (anagen), regression (catagen), and resting (telogen) phases throughout life. Stem cells located in the hair-follicle bulge area give rise to the follicle structures during each anagen phase. Bulge hair-follicle stem cells can generate all epithelial cell types within the intact follicle and hair during normal hair-follicle cycling. The bulge hair-follicle stem cells differentiate into hair-follicle matrix cells, sebaceous-gland basal cells, and epidermis. In response to wounding, some stem cells exit the bulge, migrate, and proliferate to repopulate the infundibulum and epidermis. Multipotent adult stem cells from the skin dermis, termed skin-derived precursors (SKPs), can proliferate and differentiate to produce neurons, glia, smooth muscle cells, and adipocytes. Pluripotent neural crest stem cells are present in the dermal papillae of adult mammalian hair follicles. See Amoh et al., "Multipotent nestin-positive, keratin-negative hair-follicle bulge stem cells can form neurons" Proc Natl Acad Sci USA. 12; 102(15):5530-4 (2005).

The bone marrow contains three stem cell populations—hematopoietic stem cells, stromal cells, and endothelial progenitor cells. Bone marrow stem cells, the hematopoietic stem cells (HSCs), are responsible for forming all of the types of blood cells in the body. The bone marrow-derived cells are sometimes sorted—using a panel of surface markers—into populations of hematopoietic stem cells or bone marrow stromal cells. The HSCs may be highly purified or partially purified, depending on the conditions used. Another way to separate population of bone marrow cells is by fractionation to yield cells that adhere to a growth substrate (stromal cells) or do not adhere (hematopoietic cells). The mesenchymal stem cells of the bone marrow also give rise to these tissues, and constitute the same population of cells as the bone marrow stromal cells. Progenitor cells that differentiates into endothelial cells, a type of cell that lines the blood vessels, can be isolated from circulating blood. Pericytes are related to bone marrow stromal cells.

Combinations of surface markers are used to identify, isolate, and purify HSCs derived from bone marrow and blood. Undifferentiated HSCs and hematopoietic progenitor cells express c-kit, CD34, and H-2K. These cells usually lack the lineage marker Lin, or express it at very low levels (Lin-/low). BM stromal cells have several features that distinguish them from HSCs. The two cell types are separable in vitro. When bone marrow is dissociated, the mixture of cells it contains is plated at low density, the stromal cells adhere to the surface of the culture dish, and the HSCs do not. Given specific in vitro conditions, BM stromal cells form colonies from a single cell called the colony forming unit-F (CFU-F). These colonies may then differentiate as adipocytes or myelo supportive stroma, a clonal assay that indicates the stem cell-like nature of stromal cells. Unlike HSCs, which do not divide in vitro (or proliferate only to a limited extent), BM stromal cells can proliferate for up to 35 population doublings in vitro. Endothelial stem cells are CD34+(a marker for HSCs), and they express the transcription factor GATA-2 see Kocher, et al., "Neovascularization of ischemic myocardium by human bone-marrow-derived angioblasts prevents cardiomyocyte apoptosis, reduces remodeling and improves cardiac function" Nat. Med. 7, 430-436 (2001).

The present invention contemplates the use of any type of cell including stem cells from any multicellular organism in any kingdom of species, both eukaryotes including animals, plants, protists, fungi, and prokaryotes including the kingdoms archaebacteria and eubacteria. Multicellular organisms contain totipotent, mulitpotent, pluripotent and unipotent stem cells capable of dividing and replenishing tissues and cells which compose the organism. Stem cells are well documented in mammalian animals, but are present in all animals, e.g. insects. Adult fruit flies have the same stem cells controlling cell regulation in their gut as humans do. Vertebrate and invertebrate digestive systems show extensive similarities in their development, cellular makeup and genetic control. The *Drosophila* midgut is typical: enterocytes make up the majority of the intestinal epithelial monolayer, but are interspersed with hormone-producing enteroendocrine cells. Human (and mouse) intestinal cells are continuously replenished by stem cells, the misregulation of which may underlie some common digestive diseases and cancer. In contrast, stem cells have not been described in the intestines of flies, and *Drosophila* intestinal cells have been thought to be relatively stable. By lineage labelling it has been shown that adult *Drosophila* posterior midgut cells are continuously replenished by a distinctive population of intestinal stem cells (ISCs). (Benjamin Ohlstein and Allan Spradling, The adult *Drosophila* posterior midgut is maintained by pluripotent stem cells, Nature, online Dec. 7 2005).

In addition to animal stem cells, plants also contain stem cells. Stem cells in plant shoot and root meristems are maintained throughout the life of the plant and produce somatic daughter cells that make up the body of the plant. Plant stem cells can also be derived from somatic cells in vivo and in vitro. (Plants stem cells: divergent pathways and common themes in shoots and roots. Byrne M E, Kidner C A, Martienssen R A. Curr Opin Genet Dev. 2003 October; 13(5):551-7.) Animal cells and organisms move, conduct cell divisions which serve to regenerate and maintain tissues and circulating cell populations, grow in a concurrently repetitive manner, contain a reserved germline set aside in embryogeny, have a low tolerance to genetic abnormalities, produce embryos complex and incomplete, and display essentially no asexual propagation and have no cell wall. Plants respond by physiological adjustment, their cell divisions contribute to de novo formation of organs all the way through to senescence, plant growth is serial, repetitive, and plastic, plants have no reserved germline, are more tolerant of genetic abnormalities, their embryos simple and complete, and plant cells are totipotent. Plant stem cells and seeds (plant gametes) are contemplated for use in this invention. Contrary to the rarity of totipotent cells in animals, almost every cell formed by a fungus can function as a "stem cell". The multicellular fruiting bodies of basidiomycete fungi consist of the same kind of filamentous hyphae that form the feeding phase, or mycelium, of the organism, and visible cellular differentiation is almost nonexistent (Money NP. Mushroom stem cells. Bioessays. 2002 October; 24(10):949-52).

The description is organized into the following sections: A. Mammalian embryonic stem cell extracts; B. Adult stem cell extracts; C. Cord blood cell extracts; D. Non-mammalian cell, egg and embryo extracts; E. Methods for preparing extracts; F. Epigenetic inhibitors; G. Topical delivery methods; H. Other delivery methods; I. Additional components for extracts; J. Composition profiles; K. Topical application; L. Therapeutic uses; M. Whole cell applications; N. Ex vivo and in vivo therapy.

A. Mammalian Embryonic Stem Cell Extracts

In some embodiments, the present invention provides compositions comprising embryonic stem cells or extracts prepared from embryonic stem cells. In some preferred embodiments, the cells or extracts are formulated for topical application as described in more detail below. The present invention is not limited to the use of any particular type of embryonic stem cells. Indeed, the use of embryonic stem cells from a number of animal species is contemplated, including all species in the animal kingdom, but not limited to invertebrates and vertebrates, including species in the phylum chordata, including all classes, and importantly all orders of the class mammalia, including but not limited to all primates, rodents, carnivores, lagomorphs and artiodactyles. Methods for obtaining pluripotent cells from species in these animal orders, including monkeys, mice, rats, pigs, cattle and sheep have been previously described. See, e.g., U.S. Pat. Nos. 5,453,357; 5,523,226; 5,589,376; 5,340,740; and 5,166,065 (all of which are specifically incorporated herein by reference); as well as, Evans, et al., Theriogenology 33(1):125-128, 1990; Evans, et al., Theriogenology 33(1):125-128, 1990; Notarianni, et al., J. Reprod. Fertil. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994; Evans & Kaufman, Nature 292:154-156, 1981; Martin, Proc Natl Acad Sci USA 78:7634-7638, 1981; Doetschman et al. Dev Biol 127:224-227, 1988); Giles et al. Mol Reprod Dev 36:130-138, 1993; Graves & Moreadith, Mol Reprod Dev 36:424-433, 1993 and Bradley, et al., Nature 309:255-256, 1984.

Primate embryonic stem cells may be preferably obtained by the methods disclosed in U.S. Pat. Nos. 5,843,780 and 6,200,806, each of which is incorporated herein by reference. Primate (including human) stem cells may also be obtained from commercial sources such as WiCell, Madison, Wis. A preferable medium for isolation of embryonic stem cells is "ES medium." ES medium consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL). Preferably, fetal bovine serum batches are compared by testing clonal plating efficiency of a low passage mouse ES cell line ($ES_{jt3}$), a cell line developed just for the purpose of this test. FBS batches must be compared because it has been found that batches vary dramatically in their ability to support embryonic cell growth, but any other method of assaying the competence of FBS batches for support of embryonic cells will work as an alternative.

Primate ES cells are isolated on a confluent layer of murine embryonic fibroblast in the presence of ES cell medium. Embryonic fibroblasts are preferably obtained from 12 day old fetuses from outbred CF1 mice (SASCO), but other strains may be used as an alternative. Tissue culture dishes are preferably treated with 0.1% gelatin (type I; Sigma). Recovery of rhesus monkey embryos has been demonstrated, with recovery of an average 0.4 to 0.6 viable embryos per rhesus monkey per month, Seshagiri et al. Am J Primatol 29:81-91, 1993. Embryo collection from marmoset monkey is also well documented (Thomson et al. "Non-surgical uterine stage pre-implantation embryo collection from the common marmoset," J Med Primatol, 23:333-336 (1994)). Here, the zona pellucida is removed from blastocysts by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes.

After two further washes in DMEM, lysed trophectoderm cells are removed from the intact inner cell mass (ICM) by gentle pipetting, and the ICM plated on mouse inactivated (3000 rads gamma irradiation) embryonic fibroblasts. After 7-21 days, ICM-derived masses are removed from endoderm outgrowths with a micropipette with direct observation under a stereo microscope, exposed to 0.05% Trypsin-EDTA (Gibco) supplemented with 1% chicken serum for 3-5 minutes and gently dissociated by gentle pipetting through a flame polished micropipette.

Dissociated cells are replated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (without calcium or magnesium and with 2 mM EDTA) every 1-2 weeks as the cultures become dense. Early passage cells are also frozen and stored in liquid nitrogen.

In some embodiments, extracts are prepared from the mammalian embryonic stem cells. In some embodiments, cells are washed in phosphate buffered saline (PBS) and in cell lysis buffer (100 mM HEPES, pH 8.2, 50 mM NaCl, 5 mM $MgCl_2$, 1 mM dithiothreitol and protease inhibitors), sedimented at 400 g, resuspended in 1 volume of cold cell lysis buffer and incubated for 30-45 min on ice to allow swelling. Cells are sonicated on ice in 200-µl aliquots using a Labsonic-M pulse sonicator fitted with a 3 mm diameter probe (B. Braun Biotech, Melsungen, Germany) until all cells and nuclei are lysed. The lysate is sedimented at 15,000 g for 15 min at 4° C. to pellet the coarse material. The supernatant is aliquoted, frozen in liquid nitrogen and can be stored for up to 9 months at −80° C. If necessary, extracts can be diluted with $H_2O$ prior to use to adjust the osmolarity to ~300 mOsm (i.e., isotonicity).

In some embodiments, the animal stem cell extracts, including but not limited to mammalian stem cell extracts, are used as is, while in other embodiments, the extracts are formulated either alone or with other components as described in more detail below.

B. Adult Stem Cell Extracts

In some embodiments, the present invention provides compositions comprising adult stem cells or extracts prepared from adult stem cells. In some preferred embodiments, the cells or extracts are formulated for topical application as described in more detail below. The adult stem cell is an undifferentiated (unspecialized) cell that is found in a differentiated (specialized) tissue; it can renew itself and become specialized to yield specialized cell types of the tissue from which it originated. These precursor cells exist within the differentiated tissues of the adult of all multicellular organisms in the animal, plant, protist and fungi kingdoms as a community of cells dispersed throughout the tissue. Precursor cells derived from adults can be divided into three categories based on their potential for differentiation. These three categories of precursor cells are epiblast-like stem cells, germ layer lineage stem cells, and progenitor cells. Precursor cells have been isolated from a wide variety of tissues, including, but not limited to, skeletal muscle, dermis, fat, cardiac muscle, granulation tissue, periosteum, perichondrium, brain, meninges, nerve sheaths, ligaments, tendons, blood vessels, bone marrow, trachea, lungs, esophagus, stomach, liver, intestines, spleen, pancreas, kidney, urinary bladder, and testis. Precursor cells can be released from the connective tissue compartments throughout the body by mechanical disruption and/or enzymatic digestion and have been isolated from, but not limited to, newborns, adolescent, and geriatric mice, rats and humans, and adult rabbits, dogs, goats, sheep, and pigs.

The first category of precursor cells, epiblast-like stem cells (ELSCs), consists of a stem cell that will form cells from all three embryonic germ layer lineages. Stem cells from adult rats and stem cells from adult humans can be released from the connective tissue compartments throughout the body by mechanical disruption and/or enzymatic digestion. The stem cells from either adult rats or adult humans can be preferentially slow frozen and stored at −80° C.±5° C. using 7.5% ultra-pure dimethyl sulfoxide. Fast thawing of stem cells from both species from the frozen state to ambient temperature yields recovery rates exceeding 98%. These cells in the undifferentiated state express the Oct-3/4 gene that is characteristic of embryonic stem cells. ELSCs do not spontaneously differentiate in a serum free environment lacking progression agents, proliferation agents, lineage-induction agents, and/or inhibitory factors, such as recombinant human leukemia inhibitory factor (LIF), recombinant murine leukemia inhibitory factor (ESGRO), or recombinant human anti-differentiation factor (ADF). Embryonic stem cells spontaneously differentiate under these conditions. In contrast, ELSCs derived from both species remain quiescent unless acted upon by specific proliferative and/or inductive agents and/or environment.

ELSCs proliferate to form multiple confluent layers of cells in vitro in the presence of proliferation agents such as platelet-derived growth factors and respond to lineage-induction agents. ELSCs respond to hepatocyte growth factor by forming cells belonging to the endodermal lineage. Cell lines have expressed phenotypic markers for many discrete cell types of ectodermal, mesodermal, and endodermal origin when exposed to general and specific induction agents.

The second category of precursor cells consists of three separate stem cells. Each of the cells forms cells of a specific embryonic germ layer lineage (ectodermal stem cells, mesodermal stem cells and endodermal stem cells). When exposed to general and specific inductive agents, germ layer lineage ectodermal stem cells can differentiated into, for example, neuronal progenitor cells, neurons, ganglia, oligodendrocytes, astrocytes, synaptic vesicles, radial glial cells, and keratinocytes.

The third category of precursor cells present in adult tissues is composed of a multitude of multipotent, tripotent, bipotent, and unipotent progenitor cells. In solid tissues these cells are located near their respective differentiated cell types. Progenitor cells do not typically display phenotypic expression markers for pluripotent ELSCs, such as stage specific embryonic antigen-4, stage-specific embryonic antigen-1 or stage-specific embryonic antigen-3, or carcinoembryonic antigen cell adhesion molecule-1. Similarly, progenitor cells do not typically display phenotypic expression markers for germ layer lineage stem cells, such as nestin for cells of the ectodermal lineage or fetoprotein for cells of the endodermal lineage.

A progenitor cell may be multipotent, having the ability to form multiple cell types. A precursor cell of ectodermal origin residing in the adenohypophysisand designated the adenohypophyseal progenitor cell is an example of a multipotent progenitor cell. This cell will form gonadotrophs, somatotrophs, thyrotrophs, corticotrophs, and mammotrophs. Progenitor cells for particular cell lineages have unique profiles of cell surface cluster of differentiation (CD) markers and unique profiles of phenotypic differentiation expression markers. Progenitor cells do not typically spontaneously differentiate in serum-free defined medium in the absence of a differentiation agent, such as LIF or ADF. Thus, unlike embryonic stem cells which spontaneously differentiate under these conditions, progenitor cells remain quiescent unless acted upon by proliferative agents (such as platelet-derived growth factor) and/or progressive agents (such as insulin, insulin-like growth factor-I or insulin-like growth factor-II).

Progenitor cells can regulate their behavior according to changing demands such that after transplantation they activate from quiescence to proliferate and generate both new satellite cells and substantial amounts of new differentiated cells. For example, the contractile units of muscle are myofibers, elongated syncytial cells each containing many hundreds of postmitotic myonuclei. Satellite cells are resident beneath the basal lamina of myofibers and function as myogenic precursors during muscle regeneration. In response to muscle injury, satellite cells are activated, proliferate, and differentiate, during which they fuse together to repair or replace damaged myofibers. When satellite cells are removed from their myofibers by a non-enzymatic physical titration method, they retain their ability to generate substantial quantities of new muscle after grafting that they are not able to attain by enzymatic digestion. Conventional enzymatic disaggregation techniques impair myogenic potential. Collins and Partridge "Self-Renewal of the Adult Skeletal Muscle Satellite Cell" Cell Cycle 4:10, 1338-1341 (2005).

Accordingly, the present invention also contemplates the use of non-embryonic stem cells, such as those described above. In some embodiments, mesenchymal stem cells (MSCs) can be derived from marrow, periosteum, dermis and other tissues of mesodermal origin (See, e.g., U.S. Pat. Nos. 5,591,625 and 5,486,359, each of which is incorporated herein by reference). MSCs are the formative pluripotential blast cells that differentiate into the specific types of connective tissues (i.e. the tissues of the body that support the specialized elements; particularly adipose, areolar, osseous, cartilaginous, elastic, marrow stroma, muscle, and fibrous connective tissues) depending upon various in vivo or in vitro environmental influences. Although these cells are normally present at very low frequencies in bone marrow, various methods have been described for isolating, purifying, and greatly replicating the marrow-derived mesenchymal stems cells in culture, i.e. in vitro (See also U.S. Pat. Nos. 5,197,985 and 5,226,914 and PCT Publication No. WO 92/22584, each of which are incorporated herein by reference).

Various methods have also been described for the isolation of hematopoietic stem cells (See, e.g., U.S. Pat. Nos. 5,061,620; 5,750,397; 5,716,827 all of which are incorporated herein by reference). It is contemplated that the methods of the present invention can be used to produce lymphoid, myeloid and erythroid cells from hematopoietic stem cells. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Accordingly, the present invention also contemplates the use of neural stem cells, which are generally isolated from developing fetuses. The isolation, culture, and use of neural stem cells are described in U.S. Pat. Nos. 5,654,183; 5,672,499; 5,750,376; 5,849,553; and 5,968,829, all of which are incorporated herein by reference. It is contemplated that the methods of the present invention can use neural stem cells to produce neurons, glia, melanocytes, cartilage and connective tissue of the head and neck, stroma of various secretory glands and cells in the outflow tract of the heart.

In some embodiments, extracts are prepared from the mammalian embryonic stem cells. In some embodiments, cells are washed in phosphate buffered saline (PBS) and in cell lysis buffer (100 mM HEPES, pH 8.2, 50 mM NaCl, 5 mM $MgCl_2$, 1 mM dithiothreitol and protease inhibitors), sedimented at 400 g, resuspended in 1 volume of cold cell lysis buffer and incubated for 30-45 min on ice to allow swelling. Cells are sonicated on ice in 200-µl aliquots using a Labsonic-M pulse sonicator fitted with a 3-mm. diameter probe (B. Braun Biotech, Melsungen, Germany) until all cells and nuclei are lysed. The lysate is sedimented at 15,000 g for 15 min at 4° C. to pellet the coarse material. The supernatant is aliquoted, frozen in liquid nitrogen and can be stored for up to 9 months at −80° C. If necessary, extracts can be diluted with $H_2O$ prior to use to adjust the osmolarity to ~300 mOsm (i.e., isotonicity).

In some embodiments, the adult stem cell extracts are used as is, while in other embodiments, the extracts are formulated either alone or with other components as described in more detail below.

C. Cord Blood Cell Extracts

In some embodiments, the present invention provides compositions comprising cord blood cells or extracts prepared from cord blood cells. In some preferred embodiments, the cells or extracts are formulated for topical application as described in more detail below. Transplantation of umbilical-cord blood has been successfully performed to treat individuals with blood-diseases; donors, used have been newborn siblings being perfect HLA matches for the affects sibling. The advantages of cord blood as a source of hematopoietic stem cells for transplantation are clear. First, the proliferative capacity of hematopoietic stem cells in cord blood is superior to that of cells in marrow or blood from adults. Because they proliferate rapidly, the stem cells in a single unit of cord blood can reconstitute the entire hematopoietic system. Second, the use of cord blood reduces the risk of graft-versus-host disease, the main obstacle to the success of allogeneic transplantation of hematopoietic stem cells. Graft-versus-host disease is caused by a reaction of T cells in the graft to HLA antigens in the recipient; the immaturity of lymphocytes in cord blood dampens that reaction. A joint European study showed that recipients of cord blood from HLA-identical siblings had a lower risk of acute or chronic graft-versus-host disease than recipients of marrow from HLA-identical siblings. Children with acute leukemia who received HLA-mismatched cord blood from an unrelated donor also had a lower risk of graft-versus-host disease than recipients of HLA-mismatched marrow from an unrelated donor (Hematopoietic stem-cell transplants using umbilical-cord blood, *New England Journal of Medicine*, 2001, 344(24):1860-1861, editorial)

Cord blood cells from siblings or children with matching HLA could be used to make extracts or be applied for the use as contemplated by this invention.

D. Non-mammalian Cell, Egg and Embryo Extracts

In some embodiments, the compositions of the present invention utilize cell, egg and embryo extracts from vertebrates, including but not limited to Superclass Gnathostomata (awed vertebrates), Euteleostomi (bony vertebrates), Class Actinopterygii (ray-finned fishes), Class Sarcopterygii (lobe-finned fishes and terrestrial vertebrates), Tetrapoda (tetrapods), Amniota (amniotes), Synapsida (synapsids), Class Mammalia (mammals), Early Therapsida (early therapsids), Class Reptilia (reptiles), Anapsida (tortoises and turtles), Order Testudines (tortoises and turtles), Diapsida (birds, crocodiles, lizards, snakes, and relatives), Archosauria (birds and crocodiles), Order Crocodilia (caimans, crocodiles, and relatives), Lepidosauria (amphisbaenians, lizards, snakes, and tuataras), Order Rhynchocephalia (tuataras), Order Squamata (amphisbaenians, lizards, and snakes), Class Amphibia (amphibians), Subclass Dipnoi (lungfishes), Actinistia, Order Coelacanthiformes (coelacanths), Class Chondrichthyes (rays, sharks, and relatives), Placodermi (armored fishes and placoderms), Class Cephalaspidomorphi, more preferably fish, shrimp, sea urchin or amphibian eggs or embryos. In some embodiments, unfertilized but activated fish, shrimp, sea urchin or amphibian eggs are used. The present invention is not limited to the use of any particular types of eggs. Indeed, the use of a variety of eggs is contemplated, including, but not limited to eggs from *Xenopus*, shrimp, sea urchin, salmon, trout or zebrafish. In some embodiments, eggs are collected from mature females and spontaneously activate upon contact with water. In further embodiments, the eggs are washed in Ringer's saline. In some embodiments, the eggs are not from an avian species.

E. Preparation of Extracts and Fractions

Extracts of the present invention are prepared from any of the sources described in section A-D. In some embodiments, the extracts are cellular extracts. Cellular extracts of the present invention are compositions of disrupted cells such as stem cells or eggs. The cells may be disrupted by a variety of methods, including, but not limited to, mechanical shearing or blending, sonication, or osmotic lysis. In some embodiments, the cellular extracts are preferably further processed to yield a composition that is substantially free of lipids naturally associated with the cells, such as cell membrane components. By substantially free of lipids, it is meant that the cellular extract comprises less than about 1%, preferably less than about 0.5%, and more preferably less than about 0.1% of lipids that are naturally associated with the cells used to make the cellular extract. In some embodiments, the extracts comprise less than about 1% and preferably less than 0.1% cholesterol or ovalbumin. Accordingly, in some embodiments, the cellular extract comprises carbohydrates, proteins, glycosylated or otherwise modified proteins, peptides, amino acids, RNA (mRNA, sRNA, miRNA, rRNA), DNA, water etc, and combinations thereof. In some embodiment, the cellular extracts can comprise small amounts of lipids naturally associated with the cells, as well as nuclear components such as chromosomes, nucleic acids, and nuclear proteins. In some embodiments, the cellular extract is preferably a cytoplasmic extract prepared by removing nuclear, cell membrane and other water insoluble materials naturally associated with the cells. In some embodiments, these components are removed by centrifugation or fractionation of the disrupted cells. In some embodiments, the cellular extract is preferably an aqueous extract comprising water soluble cellular components such as proteins, mRNA, and carbohydrates.

A variety of methods may be used to prepare extracts. For example, in some embodiments, eggs are placed "dry" in a glass 15 ml centrifuge tube, and crushed by sedimentation at 15,000 g for 15 min. This produces three layers: a lipid top fraction, which is collected, aliquoted and frozen; a middle cellular fraction, which is also collected, aliquoted and frozen; and a pellet fraction, which is discarded. In some embodiments, the cellular fraction or extract primarily comprises contents of the cytoplasm. The cellular fraction is used as extract. In some embodiments, the cellular fraction may be used in combination with a lipid fraction. The cytoplasmic fraction may be cleared further by sedimentation at 50,000, 100,000 or 200,000 g to yield a further cellular extract which is primarily a water soluble extract fraction. Regardless of the fraction used, the extract can be diluted to about 300 mOsm with cell lysis buffer (see above), if necessary. Accordingly, in some preferred embodiment's, a water soluble extract prepared from eggs or embryos is utilized.

In other embodiments, the eggs are suspended in 0.5 volume of cell lysis buffer and sonicated on ice until all eggs are lysed. The particulate material is sedimented at 15,000 g for 15 min at 4° C. The supernatant constitutes the extract. As above, osmolarity can be adjusted to 300 mOsm if needed. The extract can also be cleared as above.

In still other embodiments, the eggs are suspended in cell lysis buffer as in method 2. Eggs are lysed by Dounce homogenization using a glass mortar and pestle (Kontes, type A or B). The lysate is sedimented and treated as described above.

In some embodiments, extracts from stem cells, such as embryonic stem cells, are prepared in a like manner. In these embodiments, the stem cells are first disrupted and then centrifuged as above to remove insoluble cellular debris. The stem cells generally comprise much less lipid material, so the initial centrifugation yields two main fractions, a pellet and cellular fractions which primarily contains cytoplasmic components. In some embodiments, cells, either a plate of cells or cells collected from flasks or fermentors, are washed in ice cold PBS. When a plate of cells is utilized, the cells are scraped and transferred to an ice cold centrifuge tube, such as an Eppendorf tube. In some embodiments, the cells are then pelleted and the supernatant is removed. The cells are then disrupted. In some embodiments, a hypotonic solution is added to the cells in a volume of from about 1.5:1 to 3.0:1 as compared to the cell pellet. A suitable hypotonic solution comprises 10 mM HEPES pH 7.9, 1.5 mM MgCl2, 10 mM KCl 3.33, 0.5 mM DTT, and 0.2 mM PMSF. In some embodiments, a 10% solution of Triton X is then added (about 1/20 volume) to the pellet and the pellet resuspended by vortexing. In some embodiments, the cells are then homogenized, for example with a Dounce homogenizer or sonicated to further disrupt the cells. In some embodiment, the cellular debris is then pelleted by centrifugation, for example 6,000 RPM at 4° C. for 30 seconds. The supernatant is then collected as the cellular extract.

In some embodiments, the cellular extracts described above, and most preferably the middle fractions, are further fractionated. A variety of method may be used, including, but not limited to, FICOL gradients, gradient centrifugation, protein precipitation, freeze drying, column chromatography, such as size exclusion chromatography and affinity chromatography, gel separation, high pressure liquid chromatography, ChIP, and immunoprecipitation. It will be recognized that these fraction steps yield corresponding fractions such as freeze dried fractions, affinity chromatography fractions, precipitated fractions, etc.

In some embodiments, the fractions are then combined with or resolubilized with components suitable for preparing compositions for topical administration as described in more detail below.

F. Epigenetic Inhibitors

In some embodiments, the compositions of the present invention further comprise epigenetic inhibitors. In preferred embodiments, one or more epigenetic inhibitors are combined with one or more of the cellular extracts described in Sections A-E. The present invention is not limited to the use of any particular epigenetic inhibitors. Indeed, the use of variety of epigenetic inhibitors is contemplated, including, but not limited to synthetic epigenetic inhibitors and epigenetic inhibitors isolated or derived from natural sources. Examples of epigenetic inhibitors include, but are not limited to histone deacetylase inhibitors, DNA methyltransferase inhibitors and some vitamins.

In some embodiments, the epigenetic inhibitors comprises a natural extract containing butyrate or butyric acid made from natural foods such as butter from animal fats or milk (e.g. cows milk or cheese), plant oils (e.g. *Heracleum giganteum* (cow parsnip) and *Pastinaca sativa* (parsnip)), or Kombucha tea (includes Butyric Acid as a result of fermentation containing butyrate). Extract preparation may include fermentation by obligate anaerobic bacteria (e.g. *Clostridium butyricum, Clostridium kluyveri, Clostridium pasteurianum, Fusobacterium nucleatum, Butyrivibrio fibrisolvens, Eubacterium limosum*). Animal fat or plant oil product extracts may be prepared by chemical or physical processes inducing the liberation of butyric acid from the glyceride by hydrolysis. The extract could also be prepared by the fermentation of sugar or starch in the natural foods by the addition of *Bacillus subtilis*, with calcium carbonate added to neutralize the acids formed.

In other embodiments, the epigenetic inhibitors comprise a natural extract of red grapes containing the phytoalexin resveratrol, including an extract from juice or fermented juice (wine) of red grapes. Extracts could be prepared by mechanical disruption of grapes, separation of the skin from the flesh and seeds, and either extracting phytoalexin by chemical or mechanical methods, or be prepared from fresh or fermented grape juice by chemical or physical methods including boiling, fractionation, affinity chromatography, freeze-drying or gel separation.

In other embodiments, the epigenetic inhibitors comprise a natural extract containing Cyanocobalamin (vitamin B-12) made from organisms containing enzymes required for the synthesis of B12 such as bacteria and archaea, or natural products which harbor such B12 producing bacteria including meat (especially liver and shellfish), eggs, and milk products. Extracts can be prepared by chemical or physical methods such as homogenization followed by fractionation, affinity chromatography, freeze-drying or gel separation.

In other embodiments, the epigenetic inhibitors comprise a natural extract containing one or several variants of vitamin B, made from either potatoes, bananas, lentils, chilli peppers, tempeh, liver, turkey, tuna, nutritional yeast (or brewer's yeast), beer or marmite. Extracts can be prepared by chemical or physical methods such as homogenization followed by e.g. fractionation, affinity chromatography, freeze-drying or gel separation.

In other embodiments, the epigenetic inhibitors comprise a natural extract containing retinoids or retinoid precursors, made from either animal sources (e.g. milk and eggs) which contain retinyl esters, or from plants (e.g. carrots, spinach) which contain pro-vitamin A carotenoids. The extract may be modified by hydrolysis (animal sources) of retinyl esters to result in retinol, while plant extracts containing pro-vitamin A carotenoids can be cleaved to produce retinal (retinaldehyde), which can be further be reversibly reduced to produce retinol or it can be irreversibly oxidized to produce retinoic acid. The best described active retinoid metabolites are 11-cis-retinal and the all-trans and 9-cis-isomers of retinoic acid, which may be added to this extract.

Examples of other DNA methyltransferase inhibitors include, but are not limited to, 5-Azacytidine, 5-Aza-20-deoxycytidine, Arabinosyl-5-azacytidine, 5-6-Dihydro-5-azacytidine, 5-Fluoro-20-deoxycytidine, EGX30P, Epigallocatechin-3-gallate, Green tea polyphenol, Hydralazine, MG98, Procainamide, Procaine, and Zebularine. Examples of other histone deacetylase inhibitors include, but are not limited to Apicidin, Butyrates, Phenylbutyrate, m-Carboxycinnamic acid bishydroxamide (CBHA), Cyclic hydroxamic-acid-containing peptide 1 (CHAP1), TSA-Trapoxin Hybrid, Depudecin Epoxide, Depsipeptide FR901228, Benzamidine, LAQ824, Oxamflatin, MGCD0103, PXD101, Pyroxamide, Suberic Bishydroxamic Acid (SBHA), Suberoylanilide Hydroxamic Acid (SAHA), Trichostatin A (TSA), Trapoxin A, Valproic acid G. Topical Delivery Methods In some embodiments, the extracts described above (or components of the extracts) are formulated for topical delivery. General formulations for topical delivery are described in Remington's Pharmaceutical Sciences, 18th Edition, Mack Publishing, p. 1288-1300 [1990]. Accordingly, in some embodiments, the extracts are formulated as a water based gel or paste, ointment, cream (anhydrous or hydrous), lotion (anhydrous or hydrous), emulsion, spray, solution, aerosol, stick (solid cream), liquid band aid, powder, inhalation spray, nasal spray, basal drops, cheek drops, sublingual drops, eye drops or sprays, ear drops or sprays, and transdermal patches.

H. Other Delivery Methods

In some embodiments, the extracts described above (or components of the extracts) are formulated for delivery by a variety of methods. In some embodiments, the extracts described above are formulated for delivery to skin, gastrointestinal tractus, fat deposits, cartilage, bone, connective tissue, muscle or internal organs. In some embodiments, the extracts or components thereof are formulated for oral administration with or without suitable carriers such as starch, sucrose or lactose in tablets, pills, dragees, capsules, solutions, liquids, slurries, suspensions and emulsions. In some embodiments, the oral delivery vehicle comprises an enteric coating. In other embodiments, the extracts or components thereof are formulated for rectal administration as a capsule, cream, suppository or liquid. In some embodiments, the extracts of components thereof are injected by syringe to the peritoneal cavity or into internal organs or tissues. In some embodiments, the extracts or components thereof are formulated for delivery an osmotic pump.

In still other embodiments, the extracts or components thereof are delivered by microinjection, preferably via particle bombardment (i.e., with a gene gun). Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue. Other particle bombardment methods are also available. Generally, these methods involve depositing the extract or components thereof upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles that maximizes the number of cells receiving particles under uniform conditions, resulting in the introduction of the nucleic acid sample into the target tissue. This invention contemplates the described use of genegun to deliver extracts or components of extracts as defined above.

In still other embodiments, the embryonic stem cell, adult stem cell or egg extracts or components are microencapsulated (e.g., with collagen or glycosaminoglycans), formed into nanoparticles (e.g., lecithin encapsulated in an oil core), liposomes, microemulsions, or nanoemulsions, oil bodies, retinol molecular fluid films, unilamellar vesicles, multilamellar vesicles, preloaded spherical beads or sponges, elastic vesicles, etc.

I. Composition Profiles

In some embodiments the composition for topical and/or internal application is a combination of extracts with lipids and/or water and/or carbohydrates and/or nucleic acids and/or proteins and/or signaling substances. In some embodiments the extract herein is composed of whole cells or a combination of lipids and/or carbohydrates and/or nucleic acids and/or proteins and/or signaling substances of the cells from which the extract is made, or from synthetic and/or natural versions of lipids and/or carbohydrates and/or nucleic acids and/or proteins and/or signaling substances. Signaling profiles include combinations of active substances released from cells which are contained in extracts of cells, and include synthetic and/or natural versions of these signaling substances added to extracts. Signaling substances contemplated include but are not limited to growth factors, endorphins, hormones, amino acid transmitters, immunoregulatory cytokines and other immunity-associated factors.

Growth factor-β1 orchestrates the biology of irradiated tissue as a tissue level sensor of oxidative stress, and is integral to the cellular DNA damage response. Transforming growth factor-β5 (TGF-β5), a member of this signaling factor family found in amphibians, is expressed in regenerating blastemas formed under limb regeneration (King et al., 2003), and all mammalian isoforms of TGF-13 are released locally from various cells at sites of injury and are important in the control of fibrosis and scarring during mammalian tissue repair. Manipulation of specific TGF-13 isoforms is capable of producing scar-free healing of wounds in mice (Ferguson and O'Kane, 2004). TGF-β1 is a potent immunoregulatory cytokine involved in suppression of inflammation and regulatory T cell activity, resulting in immune tolerance (Chen and Wahl, 2003). Studies on wound healing and immunosuppression in mammals indicates that differential activity of TGF-13 in regenerating amphibian limb stumps may be involved suppression of fibrosis and establishing conditions permissive for blastema formation.

Transforming growth factor-alpha (TGF-alpha) and brain-derived neurotrophic factor (BDNF) secreted in vitro from human pluripotent stem cells derived from embryonic germ cells, termed embryoid body-derived (EBD) cells, have the capacity to restore neurologic function in animals by protecting host neurons from death and facilitate reafferentation of motor neuron cell bodies (Kerr D A, et al., Human embryonic germ cell derivatives facilitate motor recovery of rats with diffuse motor neuron injury. J. Neurosci. 2003 Jun. 15; 23(12):5131-40).

Fibroblast growth factors (FGFs) such as FGF-10 have been demonstrated to be of importance in regrowth of limbs in frogs (Christen and Slack, 1997; Yokoyama et al., 2000).

The Pro-opiomelanocortin (POMC) precursor for a-melanocyte stimulating hormone (α-MSH), endorphins, and several other peptide hormones, is expressed in regeneration blastemas (King et al., 2003), in skin as well as brain, pituitary, and other organs. POMC is a central importance in modulating immune activity within skin, primarily due to the activity of α-MSH (Luger et al., 1999). Paracrine release of α-MSH peptides exerts a potent immunomodulatory effect on immune cells. α-MSH inhibits all forms of inflammation against which it has been tested (Lipton et al., 1997) and localized production of α-MSH helps maintain optimal immune response at specific sites in the skin (Paus et al., 2003). Expression of α-MSH cells of a blastema would be expected to confer an anti-inflammatory effect potentially important for inhibiting fibrosis and regeneration necessary for limb or tissue regrowth.

Thymosin-β4 is a thymic maturation factor that has also been shown to promote angiogenesis, keratinocyte migration and wound healing (Malinda et al., 1999). thymosin-β4 exerts potent anti-inflammatory activity and is secreted by macrophages and T lymphocytes of skin, gut and other organs in addition to the thymus (Young et al., 1999; Girardi et al., 2003). Thymosin-β4 is up-regulated in frog pseudoblastemas (King et al., 2003) and regenerating blastemas and activities of thymosin-β4 in tissues of amputated limbs may include immunomodulation of the inflammatory response in addition to stimulation of epithelial migration and other aspects of regeneration.

J. Additional Components

In some embodiments, the extracts or components thereof described above are combined with additional components. In some embodiments, these additional components enhance uptake, bioavailability or penetration of the extract components. In preferred embodiments, extract components may contain natural or a mixture of synthetic components. The components may be partially or totally synthetic. In some embodiments, the cell or extract or synthetic components made from substances identified in the extracts are mixed with a composition comprising water, sebaceous and epidermal lipids and cell extracts, proteins, and components thereof, preferably comprises about a 10% lipid fraction by weight, about a 10% protein fraction by weight, and about an 80% volatile fraction by weight.

Vernix caseosa (vernix) is a naturally occurring skin protectant. Vernix is a lipid rich substance composed of seburn, epidermal lipids, and desquamated epithelial cells that progressively covers the skin of the developing fetus, completely surrounded by amniotic fluid, during the last trimester of pregnancy. In some embodiment, the invention relates to compositions where the lipid fraction preferably comprises components in vemix, i.e., lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated). In preferred embodiments, the vernix lipid components are as follow, with the relative percentages indicated, squalene (9%), aliphatic waxes (12%), sterol esters (33%), diesters (7%), triglycerides (26%), free sterols (9%), other lipids (4%). In additional embodiments, the lipid composition is composed of lipids from egg and/or fish roe with wound healing properties 30% of which are barrier lipids (proteolipid matrix); cholesterol (1.1%, 52.8% of barrier), free fatty acids (0.6%, 27.7% of barrier), phospholipids (0.4%), ceramides (0.7%, 20.1% barrier). In another preferred embodiment, the protein fraction contains the protein components of vernix, i.e., keratin, filaggrin, regulator proteins (e.g. EGF), and glutamine.

The fatty acids within the aliphatic waxes may be branched and the branched fatty acids may be methylated. The protein fraction consists of epidermally derived proteins, primarily keratin and filaggrin. The protein fraction also contains trace amounts in the range of about micromolar to millimolar concentrations of regulatory proteins such as epidermal growth factor (EGF), and trace amounts of about nanomolar to micromolar concentrations of surfactant protein such as Surfactant A and Surfactant B. The volatile fraction is primarily water. The rate of evaporation of volatile components is relatively slow, presumably due to increased energy requirements for the dissociation of hydrogen bonds and for diffusion from the cellular component through the lipid component to change water from the liquid to the gaseous state. In additional preferred embodiments, the composition contains mRNA contained in cell extracts, preferably stem cell extracts.

In some embodiments, the embryonic stem cell, adult stem cell or egg extracts or components are combined with phospholipids or other lipophilic substances, palmitylmyristrates, dimethylsulfoxide (DMSO), chitosan, long chain organic polymers such as polysaccharides, non-aqueous solvents, beta-glucan, pH adjusting components, skin metabolism inhibition agents, propylene glycol, butylenes glycol, polyethylene glycol, olive oil or other naturally occurring oils, dimethyl isosorbide, dimethylformamide, methyl salicylate, long chain oleic acid, mucopolysaccharides, and other agents.

In some embodiments, the additional agents include, but are not limited to, ubiquitin, antimicrobial agents (alpha-defensins, LL37, beta-defensins, etc.), surfactant proteins from the collectin family (collecting associated protein A and D), nicotinamide and psoriacin.

In some embodiments, the additional agents include, but are not limited to, vitamins, antioxidants, minerals, extracts, and chemical compounds such as alpha-tocopherol (vitamin E), melanin, vitamin C, provitamin A, retinyl proprionate, retinoic acid, Vitamin D3, Nicotinamide (vitamin B), Niacinaminde (Vit B3, exfoliates surface skin), d-panthenol (aids in skin repair of damage), vitamin A, hyaluronic acid, ceramides, Seaweed (algae) Mineral oil (paraffinum liquidium) Petrolatum Glycerin Isohexadecane *Cirtus aurantifolia* (lime) extract Microcrystalline wax (cera microcristallina) Lanolin alcohol *Seamum indicium* (sesame) seed oil, *Eucalyptus globules* (*eucalyptus*) leaf oil, Magnesium sulfate, *Sesamum indicum* (sesame) seeds, *Medicago satvia* (alfalfa) seeds, *Helianthus annuus* (sunflower) seeds, *Prunus dulcis* (powdered almonds), Sodium, Potassium, Copper, Calcium, Magnesium, zinc gluconate, Paraffin, Vitamin E succinate, Niacin, Beta-carotene, Decyl oleate, Aluminum distearate, Octyuldodecanol, Citric acid, Cyanocobalamin, Magnesium stearate, Panthenol, Limonene, Geraniol, Linalool, Hydroxycitronellal, Citronellol, Benzyl salicylate, Citral, Methylchloroisothiazoline, Methylisothiazolinone, Alcohol denat., Fragrance (parfum), Butylene glycol, Byrospermum parkii (shea butter), Fish (pisces) cartilage extract, Polyethylene, Hydrogenated polyisobutene, Cyclopentasiloxane, Cetyl esters, Cetearyl alcohol, Malachite, Isostearyl neopentanoate, Polybutene, Sucrose, Silica, Tocotrienol, *Cucumis satvius* (cucumber) fruit extract, *Centella asiatica* (hydrocotyl) extract, *Seamum indicium* (sesame) seeds, *Eucalyptus globules* (*eucalyptus*) leaf oil, *Medicago satvia* (alfalfa) seeds, *Helianthus annuus* (sunflower) seeds, *Prunus dulcis* (powdered almonds), Potassium, Copper, Calcium, Magnesium, Caffeine, Sodiumhyaluronate, Linoleic acid Cholesteryl/behenyl/octyldodecyl lauroyl glutamate, Methyl glucose sesquisterate, Cholesterol, Dimethicone, *Ocimum basilicum* (basil), *Mentha arvensis* (wild mint), Acrylates/C10-30 alkyl acrylate crosspolymer, Glyceryl distearate, Cetearyl glucoside, Steareth-10, Carbomer, Aminomethyl propanol, Limonene, Linalool, Benzyl salicylate, Disodium EDTA, BHT, Sodium dehydroacetate, Phenoxyethanol, Methylparaben, Titanium dioxide (CI 77891), C12-20 acid PEG-8 Ester, Hydrogenated vegetable oil, Petrolatum, Butylene Glycol, Glycerin, Acetylated Lanolin, Glycoproteins, *Panax, Ginseng* Root extract, *Equisetum Arvense* (Horsetail) Extract, Sodium carbomer, Beeswax (cera alba), Cetyl phosphate, Polyperfluoromethylisoporpyl ether, Benzyl alcohol, Linalool, Hydroxycitronellal, Alpha-isomethyl ionone, Amyl cinnamal, Hexyl cinnamal, Verenia furfuracea (treemoss) extract, Geraniol, Benzyl benzoate, Bytulphenol methylpropional, Eugenol, Benzyl salicylate, Chlorphenesin, Phenoxyethanol, and Methylparaben.

K. Topical Application

It is contemplated that the compositions for topical application described above find use for both cosmetic and therapeutic purposes. Therapeutic uses are described in more detail in Section J. In some embodiments, it is contemplated that the compositions described above are applied directly to the skin or other epithelial or epidermal surfaces of the body. The compositions may be applied one, two, three or more times each day as is appropriate for the indication. The amount applied is not generally important, but generally a composition comprising from about 0.001 µg to 10 grams of the extract (or components thereof) may be applied to a given surface of the body. As described above, the composition may comprise other components such as adjuvants, carriers, other active ingredients, etc.

In some embodiments, the invention relates to compositions that include preservatives and antioxidants (including vitamins) to prevent product deterioration preferably trisodium and tetrasodium edetate (EDTA) and tocopherol (vitamin E). In further embodiments the composition contains antimicrobials to fight bacteria preferably butyl, propyl, ethyl, and methyl parabens, DMDM hydantoin, methylisothiazolinone phenoxyethanol (also rose ether fragrance component), quaternium-15. In further embodiments, the composition contains thickeners and waxes used in stick products such as lipsticks and blushers preferably candelilla, carnauba, and microcrystalline waxes carbomer and polyethylene-thickeners. In further embodiments, the composition contains solvents to dilute preferably butylene glycol and propylene glycol, cyclomethicone (volatile silicone), ethanol (alcohol) and glycerin. In further embodiments, the composition contains emulsifiers to break up and refine preferably glyceryl monostearate (also pearlescent agent), lauramide DEA (also foam booster) and polysorbates. In some embodiments, the compositions contain color additives—synthetic organic colors derived from coal and petroleum sources preferably D&C Red No. 7 Calcium Lake (and other dyes that do not dissolve in water), iron oxides, mica (iridescent), and aminophenols. In further embodiments, the compositions contain pH adjusters to stabilize or adjust acids and bases preferably ammonium hydroxide—in skin peels and hair waving and straightening, citric acid—adjusts pH, and triethanolamine—pH adjuster used mostly in transparent soap. In further embodiments, the compositions contains agents preferably magnesium aluminum silicate—absorbent, anti-caking agent, silica (silicon dioxide)—absorbent, anti-caking, abrasive, sodium lauryl sulfate-detergent, stearic acid—cleansing, emulsifier, talc (powdered magnesium silicate)—absorbent, anti-caking, and zinc stearate—used in powder to improve texture, lubricates.

The composition includes the recited components and combinations thereof in a total amount of about 0.5 to 50 grams per liter, preferably about 3 to 10 grams per liter, although higher or lower concentrations are permissible. Such compositions being in the form of an emulsion, cream, salve or the like, the active materials being admixed with water, alkylene glycols, various oils natural and synthetic, petrolatum, preservatives, coloring agents, perfumes, and like ingredients conventional in the cosmetic arts.

The composition can be applied to the face, eyelids or other body parts in an amount varying with the individual. About 0.01 to 1, advantageously about 0.02 to 0.75 and preferably about 0.3 to 0.5, grams per $cm^2$ has been found useful but more or less can be used. The application can be once weekly or more often, even several times a day.

In accordance with the compositions and method of the present invention, the egg, embryo or stem cell extracts of the present invention may be administered in the form of a pharmaceutical composition additionally comprising a pharmaceutically acceptable carrier. One skilled in the art will appreciate that suitable methods of administering the extract compositions to an animal, such as a mammal, are available and, although more than one method can be used to administer a particular composition, a particular method and dosage can provide a more immediate and more effective reaction than others. Pharmaceutically acceptable carriers are also well known to those skilled in the art. The choice of carrier will be determined, in part, both by the particular composition and by the particular method used to administer the composition. Accordingly, there is a wide variety of suitable formulations of the pharmaceutical compositions of the present invention.

In some preferred embodiments, the formulations of this invention are designed for topical administration. Typical of such formulations are ointments, creams, and gels.

Ointments generally are prepared using either (1) an oleaginous base, i.e., one consisting of fixed oils or hydrocarbons, such as white petrolatum or mineral oil, or (2) an absorbant base, i.e., one consisting of an anhydrous substance or substances which can absorb water, for example, anhydrous lanolin. Customarily, following formation of the base, whether oleaginous or absorbent, the active ingredient (e.g., salmon egg extract or stem cell extract) is added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (e.g., salmon egg extract or stem cell extract) customarily is added in an amount to achieve the desired concentration.

Gels comprise a base selected from an oleaginous base, water, or an emulsion-suspension base, such as aforedescribed. To the base is added a gelling agent which forms a matrix in the base, increasing its viscosity. Examples of gelling agents are hydroxypropyl cellulose, acrylic acid polymers, and the like. Customarily, the active ingredient (IGF-II) is added to the formulation at the desired concentration at a point preceding addition of the gelling agent.

The amount of extract incorporated into the formulation of this invention is not critical; the concentration should only be in a range sufficient to permit ready application of the formulation to the wound area in an amount which will deliver the desired amount of extract.

The customary amount of formulation to be applied will depend upon concentration of the active ingredient in the formulation. In some embodiments, the amount of protein in the extract is determined. Then, a specific amount of the extract is included in the pharmaceutically acceptable carrier based on the amount of protein. Generally, the formulation will be applied to the wound in an amount affording from about 0.1 to about 500 µg of protein per cm$^2$ of skin. Preferably, the applied amount of protein will range from about 1 to about 300 µg/cm$^2$, more preferably, from about 5 to about 200 µg/cm$^2$. In other embodiments, a specific volume of extract is added to the pharmaceutically acceptable carrier. Accordingly, in some embodiments, the compositions of the present invention comprise on a volume/volume basis (volume of extract and volume of pharmaceutically acceptable carrier), for example, from about 0.001 to 50% extract, about 0.01 to 50% extract, about 0.1 to 50% extract, about 0.001 to 10% extract, about 0.01 to 10% extract, about 0.1 to 10% extract, about 0.001 to 5% extract, about 0.01 to 5% extract, about 0.1 to 5% extract, about 0.001 to 4% extract, about 0.01 to 4% extract, about 0.1 to 4% extract, about 0.001 to 2% extract, about 0.01 to 2% extract, about 0.1 to 2% extract, about 0.001 to 1% extract, about 0.01 to 1% extract, or about 0.1 to 1% extract.

The present invention may be formulated as necessary with additives used commonly in the pharmaceutical sciences, such as surfactants, oils and fats, polyhydric alcohols, lower alcohols, thickening agents, UV absorbents, light scattering agents, preservatives, antioxidants, antibiotics, chelating agents, pH regulators, flavoring agents, pigments and water.

Examples of surfactants include polyoxyethylene (hereinafter abbreviated as POE-branched alkyl ethers such as POE-octyldodecyl alcohol and POE-2-decyltetradecyl alcohol, POE-alkyl ethers such as POE-oleyl alcohol ether and POE-cetyl alcohol ether, sorbitan esters such as sorbitan monooleate, sorbitan monoisostearate and sorbitan monolaurate, POE-sorbitan esters such as POE-sorbitan monooleate, POE-sorbitan monoisostearate and POE-sorbitan monolaurate, fatty acid esters of glycerol such as glyceryl monooleate, glyceryl monostearate and glyceryl monomyristate, POE-fatty acid esters of glycerol such as POE-glyceryl monooleate, POE-glyceryl monostearate and POE-glyceryl monomyristate, POE-dihydrocholesterol ester, POE-hardened castor oil, POE-hardened castor oil fatty acid esters such as POE-hardened castor oil isostearate, POE-alkylaryl ethers such as POE-octylphenol ether, glycerol esters such as glycerol monoisostearate and glycerol monomyristate, POE-glycerol ethers such as POE-glycerol monoisostearate and POE-glycerol monomyristate, polyglycerol fatty acid esters such as diglyceryl monostearate, decaglyceryl decastearate, decaglyceryl decaisostearate and diglyceryl diisostearate and other nonionic surfactants; potassium salts, sodium salts, diethanolamine salts, triethanolamine salts, amino acid salts and other salts of higher fatty acids such as myristic acid, stearic acid, palmitic acid, behenic acid, isostearic acid and oleic acid, the above alkali salts of ether carboxylic acids, salts of N-acylamino acids, N-acylsalconates, higher alkylsulfonates and other anionic surfactants; alkylamine salts, polyamine, aminoalcohol fatty acids, organic silicone resin, alkyl quaternary ammonium salts and other cationic surfactants; and lecithin, betaine derivatives and other amphoteric surfactants.

Examples of oils and fats include vegetable oils and fats such as castor-oil, olive oil, cacao oil, camellia oil, coconut oil, wood wax, jojoba oil, grape seed oil and avocado oil; animal oils and fats such as mink oil and egg yolk oil; waxes such as beeswax, whale wax, lanolin, carnauba wax and candelilla wax; hydrocarbons such as liquid paraffin, squalene, microcrystalline wax, ceresine wax, paraffin wax and vaseline; natural or synthetic fatty acids such as lauric acid, myristic acid, stearic acid, oleic acid, isostearic acid and behenic acid; natural or higher alcohols such as cetanol, stearyl alcohol, hexyldecanol, octyldecanol and lauryl alcohol; and esters such as isopropyl myristate, isopropyl palmitate, octyldodecyl myristate, octyldodecyl oleate and cholesterol oleate.

Examples of polyhydric alcohols include ethylene glycol, polyethylene glycol, propylene glycol, 1,3-butyrene glycol, 1,4-butyrene glycol, dipropylene glycol, glycerol, diglycerol, triglycerol, tetraglycerol and other polyglycerols, glucose, maltose, maltitose, sucrose, fructose, xylitose, sorbitol, maltotriose, threitol and erythritol.

Examples of thickening agents include naturally-occurring high molecular substances such as sodium alginate, xanthene gum, aluminum silicate, quince seed extract, gum tragacanth, starch, collagen and sodium hyaluronate; semi-synthetic high molecular substances such as methyl cellulose, hydroxyethyl cellulose, carboxymethyl cellulose, soluble starch and cationized cellulose; and synthetic high molecular substances such as carboxyvinyl polymer and polyvinyl alcohol.

Examples of UV absorbents include p-aminobenzoic acid, 2-ethoxyethyl p-methoxycinnamate, isopropyl p-methoxycinnamate, butylmethoxybenzoylmethane, glyceryl-mono-2-ethylhexanoyl-di-p-methoxybenzophenone, digalloyl trioleate, 2,2'-dihydroxy-4-methoxybenzophenone, ethyl-4- bishydroxypropylaminobenzoate, 2-ethylhexyl-2-cyano-3, 3'-diphenyl acrylate, ethylhexyl p-methoxycinnamate, 2-ethylhexyl salicylate, glyceryl p-aminobenzoate, homomethyl salicylate, methyl o-aminobenzoate, 2-hydroxy-4-methoxybenzophenone, amyl p-dimethylaminobenzoate, 2-phenylbenzoimidazole-5-sulfonic acid and 2-hydroxy-4-methoxybenzophenone-5-sulfonic acid.

Examples of preservatives include benzoates, salicylates, sorbates, dehydroacetates, p-oxybenzoates, 2,4,4'-trichloro-2'-hydroxydiphenyl ether, 3,4,4'-trichlorocarbanilide, benzalkonium chloride, hinokitiol, resorcinol and ethanol.

Examples of antioxidants include tocopherol, ascorbic acid, butylhydroxyanisole, dibutylhydroxytoluene, nordihydroguaiaretic acid and propyl gallate.

Examples of chelating agents include sodium edetate and sodium citrate.

Examples of antibiotics include penicillin, neomycin, cephalothin, potassium permanganate, selenium sulfide, erythromycin, bacitracin, tethacyclin, chloramphenicol, vancomycin, nitrofurantoin, acrisorcin, chlorodontoin, and flucytosine.

Some of these additives function to enhance the efficacy of the composition by increasing the stability or percutaneous absorbability of the essential components of the present invention.

Also, any dosage form is acceptable, whether in solution, emulsion, powder dispersion, or others. Applicability is wide, including fundamental dosage forms such as lotions, emulsions, creams and gels.

In addition to those stated above, suitable vehicles, carriers and adjuvants include water, vaseline, petrolatum, mineral oil, vegetable oil, animal oil, organic and inorganic waxes, polymers such as xanthanes, gelatin, cellulose, collagen, starch, kaolin, carrageenan, gum arabic, synthetic polymers, alcohols, polyols, and the like. The carrier can also include sustained release carrier such as lypizomes, microsponges, microspheres, or microcapsules, aqueous base ointments, water in oil or oil in water emulsions, gels or the like.

The dose administered to an animal, particularly a human, in the context of the present invention should be sufficient to effect a therapeutic response over a reasonable time frame. The dose will be determined by the strength of the particular compositions employed and the condition of the person. The size of the dose and the frequency of application also will be determined by the existence, nature, and extent of any adverse side effects that may accompany the administration of a particular composition.

L. Therapeutic Uses

In some embodiments, the cell or extract compositions are useful for hydration (i.e., treating intravascular dehydration and edema in a wounds), waterproofing (i.e., compensate for hypovolemia in wounds), guarding against infection (i.e., protecting wound against infections), protection against oxidation (i.e., prevention of oxygen-free radical production during inflammatory reactions of ischemic tissue), wound healing (i.e., increased metabolism to aid in hypoxic conditions especially of burned skin or cells in anaerobic metabolism). In some preferred embodiments, the compositions are odorless (i.e., characterized by an absence of volatile carbon or nitrogen containing compounds).

In some embodiments, the invention relates to methods of using a plurality of compositions. In preferred embodiments, a first cream is used to loosen and/or dissolve cars by collagen dissolving agents or acids. A second cream with extracts or components thereof as well as other wound healing substances as described herein. In another preferred embodiment a laser, chemical peel, razor, acid, freezing, exfoliant and/or abrasive is used to remove scars or wrinkles followed by application of a cream with extracts or components thereof as well as other wound healing substances as described herein.

In some embodiments, the invention relates to a first composition preferably a cream that slows wound healing, reduces inflammation, and/or reduces scab formation. This composition is applied for several days. In preferred embodiments, the composition comprises a combination of one or more of anti-inflammatory agents, antihistamines, an extract component or components capable of dampening neutrophil migration and/or proliferation, an extract component or components the stimulate macrophages, phospholipases, arachidonic acid. In further embodiments, there is a water, lipid, protein content that provides vemix properties in the composition. In further embodiments, the components in the composition reduce activity of fibrogen cytokines. Preferably, the first composition is applied for about 1 to 3 days.

In another embodiment, the invention relates to a second composition preferably a cream that heals wounds by stimulating needed cells. Preferably this composition is applied to a subject after the first composition is applied. Preferably, the second composition is applied for about 3 to 14 days. This second composition contains components of cell and cell extracts that regulate collagenases, activate plasminogenases for clot dissolution, stimulate epithelializaiton, (i.e., migration, proliferation, dedifferentiation, redifferentiation), activate fibronectin and fibroblast growth factors, stimulate angiogenesis, reduce activity of fibrogenic cytokines and regulate genes such as TP53.

In another embodiment, the invention relates to a third composition preferably a cream. Preferably this composition is applied to a subject after the application of the second composition. This third composition functions to control collagen remodeling by collagen synthesis and destruction preferably by collegenases and metalloproteins and preferably collagan I and inactivate fibronectin, hyaluroinic acid and glycosaminoglycans, and dehydrate swelling. The third composition is preferably applied for about one to six weeks, following the application of the firs and second compositions. In some embodiments, a matrix is provided, such as a chitosan matrix, biodegradable polymer matrix, collagen matrix, or liquid band aid.

In some embodiments, the cell and/or extract composition is dispersed in a biocompatible liquid was applied to a physiologically acceptable support structure in a liquid state to form a film. A film is defined herein as a surface and/or interfacial covering, in either a liquid or a solid state, with temperature-dependant properties. Film-forming techniques include but are not limited to spraying, extruding, blowing, pouring, evaporating, coating and painting. The dispersion is presented as droplets that coalesce to form a film upon encountering the support.

In an alternate embodiment, a preformed film is applied to a support. The physiologically acceptable support structure is one that can withstand sterilization, preferably by standard sterilization techniques known to one skilled in the art such as exposure to gamma radiation, autoclaving, and so on. The support structure is not limited to a particular composition or configuration and, depending upon its use, may or may not be sterilized and may take various forms.

In another embodiment, the film is used to enhance skin cell maturation and may be applied to structures such as filters, membranes, beads, particles, and so on. Similarly, the support structure is not limited to a particular state of matter and may be a solid, a semi-solid, a gel and so on. In one embodiment, the support consists of a nylon monofilament interpositional surfacing material such as Interfaces pads (Winfield Laboratories, Inc., Dallas Tex.), Biobrane II™. (Sterling Drug Inc., New York, N.Y.) or circular nylon filters of suitable porosity (Micron Separations Inc., Westboro, Mass.). Other support materials, however, could also be used to practice the invention.

In another embodiment, the film is used to treat or prevent injury due to substance exposure or trauma, and may be applied to various materials for placement either in direct contact or indirect contact with an exposed skin site. The skin site may be intact (e.g., normal skin) or may be compromised, defined as skin that is damaged or that lacks at least some of the stratum corneum (e.g., skin damaged by exposure to the agent in question, another agent, the presence of a pathological condition such as a rash or contact dermatitis, a physical trauma such as a cut, wound, or abrasion, a underdeveloped skin such as occurs in a preterm infant, conditions in which either all or part of the epidermis is exposed, conditions in which part of the dermis has been removed such as partial thickness wounds encountered in resurfacing procedures such as chemical peels, dermabrasions, and laser resurfacing, etc.).

The support structure may be permeable to physical and/or chemical agents, and may take a variety of forms, depending upon its purpose and the extent of the area requiring dressing or treatment. The film may be applied to various synthetics such as thermoplastic films, blown films and breathable films, and various natural and synthetic fabric compositions such as woven, non-woven, spun, and stitched fabrics. The invention may be used in a variety of products, examples of which include wound dressings and coverings such as bandages, tapes, gauze, adhesive products applied for a short or long term to the skin, ostomy care products, hospital pads such as incontinent pads, absorbent pads, and examination pads, disposable and cloth diapers, and feminine hygiene products such as intralabial devices.

In some embodiments, the invention relates to regeneration of the function of skin with a desired cosmetic appearance and the prevention of skin damage. In further embodiments, early scar formation is prevented by application of a scar prevention composition when the wound is formed. In further embodiments, stimulating the rejuvenation and regeneration of stressed and aging skin prevents wrinkle formation. In further embodiments, the product is applied intermittently to slow the continual damage process that occurs as skin ages.

The skin has two main layers, the epidermis and dermis. Below these is a layer of subcutaneous ('under the skin') fat. The outer surface of the skin is the epidermis, which itself contains several layers—the basal cell layer, the spinous layer, the granular cell layer, and the stratum corneum. The deepest layer of the epidermis is the basal cell layer. Here cells are continually dividing to produce plump new skin cells. These cells move towards the skin surface, pushed upward by the dividing cells below them. Blood vessels in the dermis—which is below the basal cell layer—supply nutrients to support this active growth of new skin cells. As the basal cells move upwards and away from their blood supply, their cell content and shape change. Cells above the basal cell layer become more irregular in shape and form the spinous layer. Above this, cells move into the granular layer. Being distant from the blood supply in the dermis, the cells begin to die and accumulate a substance called keratin.

The stratum corneum ('horny layer') is the top layer of the epidermis—it is the layer of the skin that we see from the outside. Cells here are flat and scale-like ('squamous') in shape. These cells are dead, contain a lot of keratin and are arranged in overlapping layers that impart a tough and waterproof character to the skin's surface. Dead skin cells are continually shed from the skin's surface. This is balanced by the dividing cells in the basal cell layer, thereby producing a state of constant renewal. Also in the basal cell layer are cells that produce melanin. Melanin is a pigment that is absorbed into the dividing skin cells to help protect them against damage from sunlight (ultraviolet light). The amount of melanin in your skin is determined by genetic makeup and one's exposure to sunlight. The more melanin pigment present, the darker the color of your skin.

Below the epidermis is the layer called the dermis. The top layer of the dermis—the one directly below the epidermis—has many ridges called papillae. On the fingertips, the skin's surface follows this pattern of ridges to create our individual fingerprints. The dermis contains a variable amount of fat, and also collagen and elastin fibres that provide strength and flexibility to the skin. In an older person the elastin fibres fragment and much of the skin's elastic quality is lost. This, along with the loss of subcutaneous fat, results in wrinkles. Blood vessels supply nutrients to the dividing cells in the basal layer and remove any waste products. They also help maintain body temperature by dilating and carrying more blood when the body needs to lose heat from its surface; they narrow and carry less blood when the body needs to limit the amount of heat lost at its surface. The skin also contains a number of nerves and glands.

Overall skin quality and appearance can be affected by a variety of disorders, including aging, photoaging, acne, enlarged pores, and scarring. The intrinsic process of chronological aging results from thinning of the epidermis and dermis and loss of elasticity. This process affects all layers of the face, including subcutaneous tissue, the musculofascial system, the superficial musculoaponeurotic system, and the facial skeleton. The result is bony resorption, atrophy of subcutaneous fat, attenuation of the musculofibrous system, and alterations of skin surface. The dermal-epidermal junction flattens, which results in loss of rete ridges and a thinner appearance to the epidermis. The dermis also becomes thin, with a decrease in elastic fibers, collagen production, vascularity, and ground substance. The biochemical alterations in collagen and elastin result in a dermis that is more lax yet less elastic and resilient. Collectively, these changes result in fine wrinkling of the skin and sagging of the tissues that overlay the facial skeleton.

In some embodiments, the invention relates to composition comprising extracts that can stimulate skin cells to regenerate spontaneously. In additional embodiments, cells with elongated telomeres made in situ from the subject's own cells are reintroduced to the subject.

Many modalities can resurface the skin to improve skin quality, reduce age spots, soften fine lines, and treat acne or other scars. Modalities include traditional dermabrasion, chemical peeling, laser resurfacing, and microdermabrasion. The techniques attempt to remove the outer layers of skin with the idea that stimulating new growth will improve appearance. The initial evaluation of skin condition is typically accomplished using Fitzpatrick's scale of sun-reactive skin types, which denotes patients' reactions to ultraviolet radiation and existing degree of pigmentation. Type I patients always burn and never tan. Type II patients tan only with difficulty and usually burn. Type III patients tan but sometimes burn. Type IV patients rarely burn and tan with ease. Type V patients tan very easily and very rarely burn. Type VI patients tan very easily and never burn.

Chemical peeling is the chemical removal of layers of skin to improve dermatologic defects. The mechanism of action of peeling agents is relatively straightforward. Stronger agents such as phenol (with various additives such as croton oil and glycerin) and trichloroacetic acid (TCA) produce a chemical necrosis of the skin to variable depths, depending on a number of controlled and uncontrolled variables. The weaker agents change the pH sufficiently to cause a superficial shock to the cells and, depending on many variables, cell injury or death. When used with a moisturizer, the acid acts simply to cause cellular and intercellular swelling and plumping, leading to transient increase in cell and matrix size and lessening of fine lines and rhytides. Sequential treatments lead to exfoliation and a smoother complexion. Continued irritation can lead to many of the same effects of tretinoin or retinoid treatment (i.e., increased thickness of dermis, increased blood flow to skin). The phenol peel "The Baker formula" is phenol USP 88% 3 cm$^3$ 49%; distilled water 2 cm$^3$ 44%; croton oil 3 drops 2.1%; and Septisol 8 drops 4.5%.

The microdermabrasion technique abrades the skin with a high-pressure flow of crystals. Microdermabrasion is most effective with superficial skin conditions because it produces a superficial depth of injury. Superficial skin conditions include early photoaging, fine lines, and superficial scarring. Microdermabrasion is accomplished by placing the skin under tension so that an effective vacuum is achieved. Typically, stretching the treatment area with the nondominant hand and using the dominant hand to guide the handpiece is the method used to achieve this effect. When treating the neck, the neck is placed in extension to assist in skin tension. The handpiece is moved over the treatment area in a single, smooth stroke, which can then be repeated. The pressure of the crystal stream is controlled with a foot pedal. Thicker skin, such as that on the forehead, chin, and nose, can be treated more aggressively (ie, adjust the speed of handpiece movement or number of passes). Decrease the pressure when treating the thinner skin of the lower eyelids and upper cheek. Vertically orient all strokes when treating the neck.

Laser skin resurfacing (LSR) can be performed as an isolated procedure or as an adjunct to procedures such as transconjunctival blepharoplasty (TCB), facelift, and endoscopic browlift. The laser allows for precise control of ablation depth, and it permits the surgeon to vary these depths as needed. In addition to such precision, LSR causes favorable heating of the dermis, which tightens collagen fibers and stimulates neocollagen secretion by fibroblasts. Two laser wavelengths are preferred for facial skin resurfacing: pulsed carbon dioxide and erbium:yttrium-aluminum-gamet (Er: YAG). Each Er:YAG pulse removes only 25-30 micrometers of tissue compared to the pulsed carbon dioxide, which removes 50-100 micrometers. The Er:YAG produces less collateral dermal energy because the thermal conduction is approximately 5 micrometers; pulsed carbon dioxide is 30-50 micrometers. The laser output of Er:YAG is directly absorbed by collagen and dermal proteins, whereas the carbon dioxide laser vaporizes extracellular water in the dermis. Each Er:YAG pass generates the same amount of ablation, whereas the pulsed carbon dioxide generates a decreased vaporization depth with each pass.

The composition of the present invention also finds use in wound healing. A wound is a break in the skin (the outer layer of skin is called the epidermis). Wounds are usually caused by cuts or scrapes. Healing is a response to the injury that sets into motion a sequence of events. With the exception of bone, all tissues heal with some scarring. The object of proper care is to minimize the possibility of infection and scarring.

Pressure ulcers are chronic wounds caused by unrelieved pressure that results in tissue damage. The ulcers are staged from I to IV, according to the level of tissue damage observed. Pressure ulcers are most common in hospitalized patients, nursing home patients and those with spinal cord injuries. The standard of care for pressure ulcers includes interval dressing changes, pressure relief, repositioning, physical strengthening, nutritional support and infection management. If the wound becomes severe, surgical interventions include wound debridement and skin-flap, muscle-flap or free-flap reconstruction.

The present invention also finds use for the treatment of various skin disorders. Uneven skin, discoloration, and growths can be caused by a variety of factors including genetics, exposure to sun, and/or use of medications. Callus formation (Clavus) is a thickening of the skin due to intermittent pressure and frictional forces. The shape of the hands and feet are important in clavus formation. Specifically, the bony prominences of the metacarpophalangeal and metatarsophalangeal joints often are shaped in such a way as to induce overlying skin friction. As clavus formation ensues, friction against the footwear is likely to perpetuate hyperkeratosis. Toe deformity, including contractures and claw, hammer, and mallet-shaped toes, may contribute to pathogenesis. Bunionettes, ie, callosities over the lateral fifth metatarsal head, may be associated neuritic symptoms due to compression of the underlying lateral digital nerves. Furthermore, Morton toe, in which the second toe is longer than the first toe, occurs in 25% of the population; this may be one of the most important pathogenic factors in a callus of the common second metatarsal head, ie, an intractable plantar keratosis.

Moles (Nevi) are nests of melanocytes that are in contact with each other. They typically start formation during early childhood. It has been suggested that they form in response to sun exposure. However, a genetic factor is clearly involved in nevi. Some kinships express an autosomal dominant condition in which members have a large number of large nevi, sometimes more than 150 nevi scattered over the integument. Nevi have been observed to develop rapidly after blistering events, such as second-degree thermal burns or sunburns; toxic epidermal necrolysis; and in persons with genetic blistering diseases, such as epidermolysis bullosa. Growth factors, such as basic fibroblast growth factor, have been suggested to be released by proliferation keratinocytes and to stimulate melanocyte proliferation. Melanocytic nevi are benign neoplasms or hamartomas composed of mostly melanocytes, the pigment-producing cells that colonize the epidermis. Melanocytes are derived from the neural crest and migrate during embryologic development to selected ectodermal sites (primarily the skin and the CNS) but also to the eyes and the ears. Ectopic melanocytes have been identified at autopsy in the gastrointestinal and genitourinary tracts. Congenital melanocytic nevi are thought to represent an anomaly in embryogenesis and as such could be considered a malformation or a hamartoma. In contrast, most acquired melanocytic nevi are considered to be benign neoplastic proliferations.

Atypical moles/dysplastic nevi are acquired melanocytic lesions of the skin whose clinical and histologic definitions are still evolving. Atypical moles differ from common acquired melanocytic nevi in several respects, including diameter and lack of pigment uniformity Birth marks (Capillary hemangiomas) are one of the most common benign orbital tumors of infancy. They are benign endothelial cell neoplasms that are typically absent at birth and characteristically have rapid growth in infancy with spontaneous involution later in life. This is in contrast to another known group of childhood vascular anomalies, vascular malformations. Vascular malformations, such as lymphangiomas and arteriovenous malformations, are present at birth and are characterized by very slow growth with persistence into adult life.

Striae distensae (Stretch marks) affect skin that is subjected to continuous and progressive stretching; increased stress is placed on the connective tissue due to increased size of the various parts of the body. It occurs on the abdomen and the breasts of pregnant women, on the shoulders of body builders, in adolescents undergoing their growth spurt, and in individuals who are overweight. Skin distension apparently leads to excessive mast cell degranulation with subsequent damage of collagen and elastin. Prolonged use of oral or topical corticosteroids or Cushing syndrome (increased adrenal cortical activity) leads to the development of striae.

Acne manifestation is defined by the distribution of the pilosebaceous glands. Adolescence causes endocrine maturation of the adnexal elements, resulting in an accumulation of cellular products within the ductile systems. In addition to the cellular products are coexistent microorganisms, most commonly *Propionibacterium acnes* and *Staphylococcus epidermidis*.

Rosacea is a common condition characterized by symptoms of facial flushing and a spectrum of clinical signs, including erythema, telangiectasia, coarseness of skin, and an inflammatory papulopustular eruption resembling acne. Rosacea is defined by persistent erythema of the central portion of the face lasting for at least 3 months. Supporting criteria include flushing, papules, pustules, and telangiectasias on the convex surfaces. Secondary characteristics are burning and stinging, edema, plaques, a dry appearance, ocular manifestations, and phymatous changes. Perioral dermatitis (POD) is a chronic papulopustular facial dermatitis. It mostly occurs in young women. The clinical and histologic features of the lesions resemble those of rosacea.

Warts are benign proliferations of skin and mucosa caused by the human papilloma virus (HPV). Currently, more than 100 types of HPV have been identified. Certain HPV types tend to occur at particular anatomic sites; however, warts of any HPV type may occur at any site. The primary clinical manifestations of HPV infection include common warts, genital warts, flat warts, and deep palmoplantar warts (myrmecia). Less common manifestations of HPV infection include focal epithelial hyperplasia (Heck disease), epidermodysplasia verruciformis, and plantar cysts. Warts are transmitted by direct or indirect contact, and predisposing factors include disruption to the normal epithelial barrier. Treatment can be difficult, with frequent failures and recurrences.

Genital warts are a result of human papillomavirus (HPV) infection acquired by inoculation of the virus into the epidermis via defects in the epithelium (eg, maceration of the skin). Autoinoculation of virus into opposed lesions is common. Spread of HPV infection is usually through skin-associated virus and not from blood-borne infection.

Bowenoid papulosis (BP) occur on the genitalia of both sexes in sexually active people. BP is manifested as papules that are induced virally by human papillomavirus (HPV) and demonstrate a distinctive histopathology (bowenoid dysplasia).

Psoriasis is characterized by exceedingly rapid turnover of skin and appears as a chronic, bilaterally symmetric, erythematous plaquelike lesion with a silvery scale covering. The lesions classically are located over the extensor surfaces, including the elbows, knees, back, and scalp. Confluent generalized lesions also may occur.

In Von Recklinghausen disease multiple neural tumors appear on the body. Numerous pigmented skin lesions occur. The classic café au lait spots predominate. Additionally, pigmented iris hamartomas (i.e., Lisch nodules) are common. Bone lesions and intracranial and GI lesions and symptoms may be identified.

Necrobiosis lipoidica diabeticorum is a plaquelike, depressed, atrophic yellow lesion typically found in patients with diabetes. It has a strong association with diabetes and actually may be a clinical prodrome of the onset of the disease systemically. It rarely is found in locations other than the lower extremities and seldom is found in the absence of diabetes. The lesion tends to progress from a red plaquelike area to one with atrophy that occasionally may ulcerate.

Seborrheic dermatitis is a papulosquamous disorder patterned on the seburn-rich areas of the scalp, face, and trunk. In addition to seburn, this dermatitis is linked to *Malassezia*, immunologic abnormalities, and activation of complement.

Seborrheic keratosis (also known as seborrheic wart, senile wart, and basal cell papilloma) is a common benign tumor in advanced and middle-aged persons. It is typically a raised papular lesion of variable color from light to dark brown. Seborrheic keratosis may be smooth or wartlike with visible pitting. Common sites include the face, trunk, and extremities. The lesion also may be pedunculated or sessile. A variant known as dermatosis papulosa nigra occurs over the forehead and malar regions of individuals with black skin.

Acrochordons (also known as skin tag, fibroepithelial polyp, fibroma molle, and fibroepithelial papilloma) occasionally are associated with pregnancy, diabetes mellitus, and intestinal polyposis syndromes. They tend to be located in the intertriginous areas of the axilla, groin, and inframammary regions as well as in the low cervical area along the collar line. They are soft fleshy papules and usually, although not necessarily, pedunculated.

Actinic keratosis is the most common sun-related growth. Actinic keratoses are chiefly found on the sun-exposed areas of the face, the ears, the forearms, and the dorsum of the hands. However, they may occur on any area that is chronically or repeatedly exposed to the sun, such as the back, the chest, and the legs. They usually appear as multiple discrete, flat or elevated, verrucous, keratotic lesions. Lesions typically have an erythematous base covered by scale (hyperkeratosis). They are usually 3-10 mm in diameter and gradually enlarge into broader, more elevated lesions. With time, actinic keratoses may develop into invasive cutaneous horns or skin cancers. Histologically, the epidermal changes are characterized by acanthosis, parakeratosis, and dyskeratoses. Cellular atypia is present, and the keratinocytes vary in size and shape. Mitotic figures are common.

Bowen disease also is known as carcinoma in situ and squamous intraepidermoid neoplasia. Lesions involve predominantly skin unexposed to the sun (ie, protected). Classically, Bowen disease involves the genitalia. Itching is a common complaint. With vulvar involvement, the labia majora tend to be involved more than the labia minora. The lesions are scaly, crusted, erythematous plaques.

Pseudocarcinomatous hyperplasia are lesions caused by a reparative process characterized by tongues of squamous epithelium growing downward into the dermis.

Nevus sebaceus of Jadassohn is a hamartomatous lesion expressing elements of sebaceous and apocrine glands, defective hair follicles, acanthosis, and papillomatosis. It is a congenital lesion, usually present on the scalp and face. The lesion tends to enlarge with time.

Lupus erythematosus (LE) is a heterogeneous connective-tissue disease associated with polyclonal B-cell activation.

Sebaceous adenoma is a nodular and lobulated lesion with peripheral generative cells and variable sebaceous differentiations as the center of the lesion is approached. It is not as organized as the patterns of sebaceous hyperplasia. This lesion is distinct from the hamartomatous variety encountered on the face of patients with tuberous sclerosis syndrome.

Inverted follicular keratosis is believed to be an inflammatory variant of Seborrheic keratosis. It commonly is found on the faces and sun-exposed areas of elderly patients. Typically, this lesion is located on the upper eyelid. Anatomically, it represents an upside-down or endophytic process within the epithelium of a pilosebaceous follicle. The lesions tend to be single and present as a papule or nodule.

Trichoepithelioma is an uncommon benign lesion. It is generally pink to flesh colored. It is frequently multiple and is not ulcerative. These lesions tend to be recapitulations of hair follicles. Initially, they appear during adolescence. Typical areas for this lesion are the face and scalp and, less commonly, the trunk and neck.

Trichilemmoma is a benign tumor with a pattern of globular glycogen-rich clear cells. Occasionally, keratinization in the center is identified grossly.

Molluscum sebaceum is a self-healing skin tumor. The lesion is classically a dome-shaped mound with a central crater of keratin.

Basal cell carcinoma is an epithelial malignancy that appears as insidious, painless, nonhealing ulcers or nodules on the sun-exposed parts of the body. The most common location on the head is the nose, specifically the nasal tip and alae. Risk is related to skin type and the degree of exposure to sunlight, particularly UV-B radiation. The tumors are more frequent in individuals with fair complexions.

Most Squamous cell carcinomas appear on sun-exposed regions of the body. Squamous cell carcinoma (SCC) arises from the malignant transformation and proliferation of keratinocytes in the epidermis. SCC can arise from actinic keratosis, leukoplakia, radiation keratosis or dermatitis, scars, chronic ulcers, or chronic sinusitis. People with actinic keratosis have atypical squamous cells in a third to a half of the epidermis. Those with Bowen disease, or SCC in situ, have atypical keratinocytes in the entire epidermis. Invasive SCC involves the epidermis and invades the dermis. The tumors initially appear as skin patches, plaques, and nodules that enlarge and develop central areas of inflammation, induration, and, subsequently, necrosis and oozing. SCCs metastasize by direct, lymphatic, and hematogenous extension.

Melanoma is a tumor that develops as a result of the malignant transformation of melanocytes. These cells are derived from the neural crest. Melanomas usually occur on the skin but can arise in other locations where neural-crest cells migrate, such as in the gastrointestinal tract or brain.

It is contemplated that the compositions of the present invention find use in the treatment of all of the foregoing skin conditions and disorders.

The compositions of the present invention also find use in the treatment of burns. Sunburn is an acute cutaneous inflammatory reaction that follows excessive exposure of the skin to ultraviolet radiation (UVR). Exposure to solar radiation has the beneficial effects of stimulating the cutaneous synthesis of vitamin D and providing radiant warmth. Unfortunately, when the skin is subjected to excessive radiation in the ultraviolet range (wavelength <400 nm), deleterious effects may occur. The most common is acute sunburn or solar erythema. Eyes, particularly the cornea (the clear window of tissue on the front of the eyeball), can be damaged easily by exposure to ultraviolet radiation from the sun and from other sources of ultraviolet light, such as a welder's arc, a photographer's flood lamps, a sun lamp, or even a halogen desk lamp.

Severe burns result in skin barrier destruction that can lead to fluid and electrolyte losses and in skin infection that result in systemic infection. Burns are rated on the degree of injury to the tissue. First-degree burns involve damage to the top layer of skin (epidermis), and second-degree burns involve the epidermis and the underlying layer of skin (dermis). First- and second-degree burns can also be called partial-thickness burns. Third-degree burns affect the epidermis, dermis and hypodermis, causing charring of skin or a translucent white color, with coagulated vessels visible just below the skin surface. These are also called full-thickness burns.

Treating severely burned patients includes early cleaning and debriding of the wound, intravenous (IV) fluids containing electrolytes, systemic antibiotics, topical antibiotics, nutritional support and medication to control pain. Skin grafting, generally with skin taken from donor sites from the patient, may be required to achieve closure of the wounded area. In large burns, autograft skin may not be available in sufficient quantities to completely close the wound. In this case, expanded autografts are applied to the wound, and cadaver allograft is then used to close the wound completely. Skin graft donor sites are surgically created wounds that require the same level of care as other open wounds.

The compositions of the present invention also find use in the treatment of various types if internal wounds. Wounds on internal tissues may be the result disease of surgery such as those created by of removal of cancerous tissues or correction of a cleft lip and/or palate. Wounds can form on the membranes of the mouth, nose and digestive system.

A cleft lip or palate affects the obvious facial form as an anatomic deformity and has functional consequences, affecting the child's ability to eat, speak, hear, and breathe. Specifically, in the child born with a bilateral cleft, the surgeon initially is faced with a protrusive premaxilla and the difficulty of achieving adequate columellar length and vertical height to the lip during reconstruction. Although surgery for the bilateral cleft lip has undergone many recent advances, correction of the nasal deformities associated with this congenital malformation remains one of the greatest challenges in plastic surgery. Surgical correction of nasal deformities associated with bilateral cleft lip is challenging because deformities may become apparent as the nose undergoes further growth and development.

Removal of cancer from the jawbone often creates a gap in the bone that wounds surrounding tissues. Distraction osteogenesis is a technique in which bone can be lengthened by de novo bone formation as part of the normal healing process that occurs between surgically osteotomized bone segments that undergo gradual, controlled distraction.

Velopharyngeal (VP) dysfunction includes any structural and/or neuromuscular disorder of the velum and/or pharyngeal walls at the level of the nasopharynx in which interference with normal sphincteric closure occurs. VP dysfunction may result from anatomic, myoneural, behavioral, or a combination of disorders.

Erythema multiforme (EM) is an acute mucocutaneous hypersensitivity reaction of variable severity characterized by a symmetrically distributed skin eruption, with or without mucous membrane lesions. The more common mild form, EM minor, consists of skin lesions with involvement of no more than one mucosal surface. Symmetrically distributed, erythematous, expanding macules or papules evolve into classic iris or target lesions, with bright red borders and central petechiae, vesicles, or purpura. EM major, or Stevens-Johnson syndrome, is more severe, involving 2 or more mucous membranes with more variable skin involvement. It may involve internal organs and typically is associated with systemic symptoms. Skin findings may be similar to EM minor but often are more variable and severe. Inflammatory vesiculobullous lesions, often with hemorrhage and necrosis, are typical.

Rhinitis is defined as inflammation of the nasal membranes and is characterized by a symptom complex that consists of any combination of the following: sneezing, nasal congestion, nasal itching, and rhinorrhea. The eyes, ears, sinuses, and throat can also be involved. Allergic rhinitis is the most common cause of rhinitis.

Crohn disease is an idiopathic, chronic, transmural inflammatory process of the bowel that can affect any part of the GI tract from the mouth to the anus. The condition is believed to be the result of an imbalance between proinflammatory and anti-inflammatory mediators. Most cases involve the small bowel, particularly the terminal ileum. The characteristic presentation of Crohn disease is with abdominal pain and diarrhea, which may be complicated by intestinal fistulization, obstruction, or both. The initial lesion starts as a focal inflammatory infiltrate around the crypts, followed by ulceration of superficial mucosa. Later, inflammatory cells invade deep layers and, in that process, begin to organize into noncaseating granulomas. The granulomas extend through all layers of the intestinal wall and into the mesentery and the regional lymph nodes. Although granuloma formation is pathognomonic of Crohn disease, absence does not exclude the diagnosis. The initial abnormality is hyperemia and edema of the involved mucosa. Later, discrete superficial ulcers form, which become deep serpiginous ulcers located transversely and longitudinally over an inflamed mucosa, giving the mucosa a cobblestone appearance. The lesions are often segmental, being separated by healthy areas. Malabsorption occurs as result of loss of functional mucosal absorptive surface. This phenomenon can lead to protein-calorie malnutrition, dehydration, and multiple nutrient deficiencies. Involvement of the terminal ileum may result in malabsorption of bile acids, which leads to steatorrhea, fat-soluble vitamin deficiency, and gallstone formation. Fat malabsorption, by trapping calcium, may result in increased oxalate excretion (normally complexed by calcium), causing kidney stone formation.

Gastritis includes a myriad of disorders that involve inflammatory changes in the gastric mucosa, including erosive gastritis caused by a noxious irritant, reflux gastritis from exposure to bile and pancreatic fluids, hemorrhagic gastritis, infectious gastritis, and gastric mucosal atrophy. Peptic ulcer disease (PUD) refers to a discrete mucosal defect in the portions of the gastrointestinal tract (gastric or duodenal) exposed to acid and pepsin secretion. Erosive gastritis usually is associated with serious illness or with various drugs. Stress, ethanol, bile, and nonsteroidal anti-inflammatory drugs (NSAIDs) disrupt the gastric mucosal barrier, making it vulnerable to normal gastric secretions. Infection with *Helicobacter pylori*, a short, spiral-shaped, microaerophilic gram-negative *bacillus*, is the leading cause of PUD and is associated with virtually all ulcers not induced by NSAIDs.

Oral herpes is an infection caused by the herpes simplex virus. The virus causes painful sores on your lips, gums, tongue, roof of your mouth, and inside your cheeks. It also can cause symptoms such as fever and muscle aches.

The compositions of the present invention further find use in enhancing the various phases of the healing process. There are different phases to the healing process. The inflammatory phase begins with the injury itself. The inflammatory phase is characterized by hemostasis and inflammation. Here you have bleeding, immediate narrowing of the blood vessels, clot formation, and release of various chemical substances into the wound that will begin the healing process. Specialized cells clear the wound of debris over the course of several days. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, potent vasoconstrictors. This initial response helps to limit hemorrhage. After a short period, capillary vasodilatation occurs secondary to local histamine release, and the cells of inflammation are able to migrate to the wound bed.

Platelets, the first response cell, release multiple chemokines, including epidermal growth factor (EGF), fibronectin, fibrinogen, histamine, platelet-derived growth factor (PDGF), serotonin, and von Willebrand's factor. These factors help stabilize the wound through clot formation. These mediators act to control bleeding and limit the extent of injury. Platelet degranulation also activates the complement cascade, specifically C5a, which is a potent chemoattractant for neutrophils. The inflammatory phase continues, and more immune response cells migrate to the wound. The second response cell to migrate to the wound, the neutrophil, is responsible for debris scavenging, complement-mediated opsonization of bacteria, and bacteria destruction via oxidative burst mechanisms (ie, superoxide and hydrogen peroxide formation). The neutrophils kill bacteria and decontaminate the wound from foreign debris. The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, ie, the proliferative phase.

In the proliferative phase a matrix or latticework of cells forms. On this matrix, new skin cells and blood vessels will form. It is the new small blood vessels (known as capillaries) that give a healing wound its pink or purple-red appearance. These new blood vessels will supply the rebuilding cells with oxygen and nutrients to sustain the growth of the new cells and support the production of proteins (primarily collagen). The collagen acts as the framework upon which the new tissues build. Collagen is the dominant substance in the final scar.

Epithelialization, angiogenesis, granulation tissue formation, and collagen deposition are involved in the proliferation phase anabolic portion of wound healing. Epithelialization occurs early in wound repair. If the basement membrane remains intact, the epithelial cells migrate upwards in the normal pattern. This is equivalent to a first-degree skin burn. The epithelial progenitor cells remain intact below the wound, and the normal layers of epidermis are restored in 2-3 days. If the basement membrane has been destroyed, similar to a second- or third-degree burn, then the wound is reepithelialized from the normal cells in the periphery and from the skin appendages, if intact (eg, hair follicles, sweat glands)

Angiogenesis, stimulated by TNF-alpha, is marked by endothelial cell migration and capillary formation. The new capillaries deliver nutrients to the wound and help maintain the granulation tissue bed. The migration of capillaries into the wound bed is critical for proper wound healing. The granulation phase and tissue deposition require nutrients supplied by the capillaries, and failure for this to occur results in a chronically unhealed wound. Mechanisms for modifying angiogenesis are under study and have significant potential to improve the healing process.

During granulation tissue formation, fibroblasts differentiate and produce ground substance and then collagen. The ground substance is deposited into the wound bed; collagen is then deposited as the wound undergoes the final phase of repair. Many different cytokines are involved in the proliferative phase of wound repair. The steps and the exact mechanism of control are not well understood. Some of the cytokines include PDGF, insulinlike growth factor (IGF), and EGF.

During a remodeling stage, the framework (collagen) becomes more organized making the tissue stronger. The blood vessel density becomes less, and the wound begins to lose its pinkish color. Over the course of 6 months, the area increases in strength, eventually reaching 70% of the strength of uninjured skin. In the maturational phase, the wound undergoes contraction, ultimately resulting in a smaller amount of apparent scar tissue. The entire process is a dynamic continuum with an overlap of each phase and continued remodeling. The wound reaches maximal strength at one year, with a tensile strength that is 30% of normal skin. Collagen deposition continues for a prolonged period, but the net increase in collagen deposition plateaus after 21 days.

Epithelialization is the process of laying down new skin, or epithelial, cells. The skin forms a protective barrier between the outer environment and the body. Its primary purpose is to protect against excessive water loss and bacteria. Reconstruction of this layer begins within a few hours of the injury and is complete within 24-48 hours in a clean, sutured (stitched) wound. Open wounds may take 7-10 days because the inflammatory process is prolonged, which contributes to scarring. Scarring occurs when the injury extends beyond the deep layer of the skin (into the dermis).

The 3 categories of wound closure are primary, secondary, and tertiary. Primary healing involves closure of a wound within hours of its creation. Secondary healing involves no formal wound closure; the wound closes spontaneously by contraction and reepithelialization. Tertiary wound closure, also known as delayed primary closure, and involves initial debridement of the wound for an extended period and then formal closure with suturing or by another mechanism.

The compositions of the present invention further find use for the treatment of scars, alone or in combination with known scar treatments. Open wounds can result in a number of complications including wound infection and disfiguring scars including keloids, widened scars, and hypertrophied scars. Both keloid and hypertrophic scars are wounds that heal overzealously above the skin surface. The difference between a keloid and a hypertrophied scar is that a keloid continues to enlarge beyond the original size and shape of the wound, while a hypertrophied scar enlarges within the confines of the original wound. Although both can be red and raised, keloids continue to grow and hypertrophied scars tend to regress over time. Both can recur after surgical excision; however, the recurrence of keloid scars is more common. Widened scars are wounds that separate during the healing process, usually in response to tension perpendicular to the wound edges. Hypertrophic scars are more common than keloids. Hypertrophic scars may occur in persons of any age or at any site, and they tend to spontaneously regress. In general, hypertrophic scars are more responsive to treatment. While keloids occur frequently in black persons, they may occur in persons of any race with a proven tendency to keloid formation. Keloids are more prevalent in persons aged 10-30 years, while hypertrophic scars occur in persons of any age.

Which factors initiate keloid or hypertrophic scar formation is not well understood. Several genetic and environmental causes have been implicated in the etiology of keloid and hypertrophic scars. In both keloid and hypertrophic scar formation, an excessive accumulation of collagen from increased collagen synthesis or decreased collagen degradation occurs. Proposed causes for abnormal scar formation include foreign body reaction and bacterial infections. Many abnormal scars are associated with tattoos, burns, injections, bites, vaccinations, trauma, surgery, or infection. Skin tension is frequently implicated in hypertrophic scar formation. Abnormal scar healing commonly involves areas of high skin tension, such as the anterior chest, shoulders, and upper back. Other factors implicated in the etiology of abnormal scar formation include wound infection or anoxia, a prolonged inflammatory response, and wound orientation different from the relaxed skin tension lines. Keloid formation has a genetic basis, as demonstrated by its predilection for persons of certain races and in certain families. Because keloids tend to demonstrate accelerated growth during puberty or pregnancy and tend to resolve with menopause, hormones (both androgen and estrogen) have been implicated in keloid formation. Other hormones linked to keloid formation include thyroid hormone alterations and melanocyte-stimulating hormones. Immunologic alterations are implicated in abnormal scars. Specifically, irregular immunoglobulin and complement levels, increased transforming growth factor-beta, and mast cells are found in abnormal scars. Additionally, decreased tumor necrosis factor and interleukin 1 levels are found in these abnormal scars. Widened scars result from excess tension perpendicular to the wound edges during the healing process. Scar widening usually occurs within the first 6 months of injury.

Although multiple factors are involved in abnormal scar formation, studies indicate that keloid and hypertrophied scars result from increased collagen production and decreased collagen degradation. Levels of the collagen-related enzyme prolyl hydroxylase are elevated in keloid-affected skin compared with normal skin. Prolyl hydroxylase is required for the hydroxylation of proline during collagen synthesis, suggesting that collagen overproduction occurs with keloids.

Collagen production is elevated in keloid biopsy samples and in cultured fibroblasts derived from keloids. Increased collagen production by cultured fibroblasts derived from keloids persists throughout their in vitro life span; they do not revert to normal after transfer of the lesion to culture. No significant differences in DNA content or cellularity are found when keloid dermis is compared with normal dermis. This suggests that each fibroblast is producing more collagen rather than an increase occurring in the number of fibroblasts producing a normal amount of collagen. In keloid formation, excessive collagen production by fibroblasts is likely due to the wound environment.

Widened scar formation is thought to result from wound edge separation with tension perpendicular to the healing skin wound. A state of tension exists naturally in skin; wounded skin gapes and becomes elliptical rather than round. When a wound is closed opposite to the lines of tension, the chance of widened scar formation is increased.

Upon clinical examination, keloids and hypertrophic scars are raised above the skin level. Hypertrophic scars are self-limited; they hypertrophy within the confines of the wound. Initially, hypertrophied scars can be raised, red, pruritic, and even painful; however, over time, they become pale and flat. Hypertrophied scars appear worst at 2 weeks to 2 months. Keloid scars can be differentiated from hypertrophic scars by their spread beyond the original wound. Keloid scars tend to remain red, pruritic, and painful for many months to years until menopause. Patients usually have a personal or familial history of keloid formation. Different from hypertrophic and keloid scars, widened scars are flat and sometimes depressed. With adequate wound maturation, these wounds fade to the pigment of the surrounding uninjured skin. Widened scars are not usually red or pruritic.

The relaxed skin tension lines follow furrows formed when the skin is relaxed. Unlike wrinkles, they are not visible features of the skin. They are merely derived from the furrows produced by pinching on the skin. These furrows are produced preferably with pinching perpendicular to the lines. When the skin is pinched oblique to the relaxed skin tension lines, an S-shaped pattern is created. Fewer and higher furrows are created if skin is pinched parallel to the lines. Closing incisions opposite to the relaxed skin tension lines can increase the risk of widened or hypertrophic scar formation.

A potential relative contraindication to scar revision surgery exists when the scar is a keloid because of the risk of worsening the scar. Sometimes, when keloids recur, they become larger than the original. Widened scars can be easily differentiated from hypertrophic and keloid scars based on findings from a physical examination. Widened scars are flat and sometimes even depressed. Hypertrophic scars and keloids are indistinguishable under light microscopy. However, there are a number of differences when viewed under an electron microscope and when evaluated immunochemically. Keloids contain thick collagen fibers with increased epidermal hyaluronic content, whereas hypertrophic scars exhibit nodular structures with fine collagen fibers and increased levels of alpha smooth muscle actin. The collagen in both keloids and hypertrophic scars is organized in discrete nodules, frequently obliterating the rete pegs in the papillary dermis of the lesions. While collagen in normal dermis is arranged in discrete fascicles separated by considerable interstitial space, collagen nodules in keloids and in hypertrophic scars appear avascular and unidirectional and are aligned in a highly stressed configuration.

Different nonsurgical options treat abnormal scars. Pressure is thought to decrease tissue metabolism and increase collagen breakdown within the wound. The different methods of applying pressure include the use of elastic bandages (ACE wraps), thromboembolic disease stockings, or Isotoner-type gloves on extremities. Alternatively, custom-fitted compression garments can be used to apply pressure to the more difficult areas, including the neck and torso. Because these devices are uncomfortable, patient compliance varies. Unfortunately, for optimal results, these devices must be used for 6-12 months during the maturation of the wound.

Silicone gel can be used to treat abnormal scars. Silicone gel is shown to significantly decrease scar volume when used over time particularly for hypertrophic scar formation. The effect of the silicone gel on the scar is believed to be due to wound hydration. The silicone gel is applied to the wound for at least 12 h/d. Patients find it more appealing to apply the silicone to their wounds at night. Silicone gel is gaining popularity because it can be applied to a smaller area for 12 h/d, usually at night. However, skin breakdown, rashes, and difficulty with wound adherence can lead to disuse.

Steroid injections have become a common nonsurgical option in the treatment of problem scars. The steroid used for intralesional injection is triamcinolone (Kenalog). Triamcinolone injections have been the standard treatment to induce flattening, fading, and decreased symptomatology of hypertrophied scars. These injections can be administered as soon as a problem scar is identified. The dose of the injection can vary from 10-120 mg, depending on the size of the scar.

One may make use of a triamcinolone injection for thin-to-wide hypertrophied scars and silicone for very wide hypertrophied scars. Some patients prefer triamcinolone injections to avoid applying and wearing the silicone every day for 6-9 months, especially on body areas where adherence is poor. Adverse effects of triamcinolone injections include hypopigmentation and subcutaneous atrophy. Other nonsurgical options include corticosteroid intralesional injections, vitamin E therapy, zinc oxide therapy, antineoplastic agents, and immunotherapy.

If nonoperative measures are unsuccessful in the treatment of abnormal scars, operative intervention can be considered. Closing wounds to orient the wound along the relaxed skin tension lines is important. A standard practice often used rather subconsciously after excision of a lesion involves assessing the direction of least tension based on the configuration of the edges of the wound or by pinching the wound.

The first-line procedure used for scar revision is fusiform excision. In general, fusiform excision does not require lengthening the scar. In order to avoid canine auricles, ensure the wound has a length-to-width ratio of 4:1. Fusiform excision is preferred for short wounds oriented along relaxed skin tension lines. The Millard flap procedure is similar to fusiform excision, but it involves preserving the scar and its connection to the underlying fat. The skin is incised in a fusiform fashion around the scar to the subcutaneous level. The scar is then deepithelialized, and the skin edges are approximated over the deepithelialized scar. The Millard flap technique is preferred for widened, depressed scars.

Scars not oriented along the relaxed skin tension lines can be modified with a Z-plasty procedure. Limbs of equal length are created for the Z plasty. The angle of the Z dictates the length of scar tension distribution and elongation (eg, 300 for 25%, 45° for 50%, 60° for 75%, 75° for 100%, 900 for 120%). The W-plasty technique for scar revision is similar to Z plasty because of the result of breaking up a straight-line scar into a pattern that is less conspicuous. Similar to a fusiform excision, W plasty involves the removal of skin; therefore, avoid this method if significant tension is present across the wound edges. W-plasty scar revision is preferred for scars along relaxed skin tension lines; scars with a bowstring contracture; short, depressed scars; and facial scars.

Tissue expansion and serial excision can be considered for larger scar revisions when excess wound tension is predicted. If more than 2 serial excisions are expected, tissue expansion is preferred. Finally, other procedures that have been described to treat scars include dermabrasion, cryosurgery, and laser therapy. Widened scars may be treated differently than hypertrophied scars. Widened scars can be flat or even depressed. Therefore, the administration of intralesional steroids is not preferred; these agents might worsen the depression. Widened scars are preferably treated with the Millard 2-flap technique over a deepithelialized scar. This technique provides soft tissue fill under the approximated wound edges. Furthermore, if the widened scar recurs, the risk for another recurrence may be minimized by reorienting the wound tension along the lines of relaxed skin tension. Other adjuncts described in the treatment of widened scars include the injection of fat grafts or other tissue substitutes. When oriented close to the relaxed skin tension lines, hypertrophic scars can be excised in a fusiform fashion. If the hypertrophic scar developed because of excessive tension across the wound as a result of unfavorable wound orientation, Z plasty can sometimes help reorient the wound to distribute tension in a different direction to minimize the risk of recurrence.

Postoperatively, compression garments and silicone gel are preferred for 4-6 months to decrease the risk of recurrence. Patients are encouraged to refrain from strenuous activities for at least 6 weeks, until which time the wound achieves approximately 80% original wound tensile strength. Patients are monitored for 6 months postoperatively to detect and potentially circumvent recurrences early. Postoperatively, patients are at risk for hypertrophic scar and widened scar recurrence. Other risks include infection, hematoma, seroma, and painful or unattractive scarring. The risk of recurrence is significant for both hypertrophic and widened scars, and it is increased with repeat operations. Wound healing requires approximately 1 year, during which time the surgeon and patient should observe for and expect improvement. Once the scar has had an opportunity to mature, scar revision can be considered.

In some embodiments of the present invention, compositions comprising cell extracts are utilized to improve any area of the person visible and contributing to cosmetic appearance of a person, including but not limited to skin, hair, nails, teeth, subcutaneous fat, cartilage, muscle and skeletal structures. The described gene-gun and microinjection delivery methods are contemplated to introduce extracts or extract components to structures below the surface skin of a person.

This invention relates to prevention of deterioration, damage and malfunction of cells and tissues, and to promote, improve and exceed cellular function in order to promote, improve and exceed appearance, vitality and health by treating cells and tissues with differentiable cells, cell or egg extracts, or components of said extracts including signaling molecules, peptides, carbohydrates, lipids or nucleic acids.

The current invention contemplates the assessment of a persons needs for healing, regeneration or repair of damage by several means, including but not limited to analysis and measurements of visible surfaces, skin pH, thickness, structure and elasticity of skin layers, analysis of blood or tissue samples by microchip, RT-PCR, Mass spectrometry, high pressure liquid chromatography, ELISA-assays, RNA analysis, analysis of accumulation of DNA damage or defective genes by DNA sequencing, assessment of internal organ and tissue health by X-ray imaging, ultrasound imaging, computed tomogpraphy (CT), magnetic resonance imaging (MRI), positron emission tomography (PET).

Subcutaneous fat contributes to the cosmetic appearance of a person, and is redistributed during ageing, by smoking and in a number of diseases, including HIV and diabetes as well as in burn-victims. The human immunodeficiency virus (HIV)-lipodystrophy syndrome is associated with fat redistribution and metabolic abnormalities, including insulin resistance. Increased intramyocellular lipid (IMCL) concentrations are thought to contribute to insulin resistance, being linked to metabolic and body composition variables. Among HIV-infected subjects, calf subcutaneous fat area and extremity fat are reduced. Extremity fat is significantly associated with IMCL among HIV-infected patients, controlling for visceral abdominal fat, abdominal subcutaneous fat, and antiretroviral medications in a regression model. Increased IMCL in HIV-infected women with a mixed lipodystrophy pattern are most significantly associated with reduced extremity fat. (Torriani M et al., J Appl Physiol. 2006 February; 100(2):609-14. Epub 2005 Oct 13). Saturation of the subcutaneous fat depot is the primary event in the pathophysiology of insulin resistance in the majority of patients and postulate that this seminal event may lead to the development of hypertension, hypertriglyceridemia and depressed HDL levels (i.e., the metabolic syndrome). There are no current effective means to redistribute subcutaneous fat in such persons, current treatment include (1) weight loss with differing responses seen with regards to insulin resistance depending on the size of the fat depot; (2) peroxisome proliferator activated receptor gamma agonists, such as thiazoledinediones which expand the subcutaneous fat depot, (3) expanding alternate storage sites for triglycerides by a variety of techniques, such as resistance training-induced muscle hypertrophy, may also improve insulin resistance; (4) drugs, such as beta 3 adrenergic receptor agonists which promote lipolysis may increase insulin resistance by releasing free fatty acids into the circulation. Inhibitors of the beta oxidation of free fatty acids (e.g., carnitine palmitoyl transferase inhibitors) may cause insulin resistance by sparing fat and (5) liposuction, by reducing the size of the subcutaneous fat depot may worsen insulin resistance, thus increasing the risk of type 2 diabetes mellitus (Cheman M A, Santoro T J, Med. Hypotheses. 2005 Dec. 14; [Epub ahead of print]).

Alterations in subcutaneous fat and skin condition due to hormone changes that occur during ageing and disease are also contemplated areas of use for this invention. Effects of ovarian and other steroids are important to the metabolism of skin and hair, the changes in body composition and the alterations of the subcutaneous fat distribution throughout life. So called aesthetic endocrinology accesses deficiency or excess of ovarian steroids that lead to different problems skin and hair and other non-genital, i.e., obesity and cellulite. Sex steroids are small molecules that are transported into the skin by topical application when properly formulated, and are contemplated to be added to the extracts presented in this invention in order to achieve local effects but to avoid systemic reactions. Estrogens, delivered orally or topically, may counteract the aging of the skin especially post-menopause. Estrogen alone is not sufficient for reconstitution of juvenile skin but may slow the skin aging process. The hitherto only successful treatment of hair loss in women is by application of the non-hormonal compound minoxidil, and compositions contemplated by this invention may serve to be a different way of treating hair loss. Indeed, the compositions contemplated may stimulate hair sack follicles to regrow or increase the rate and quality of hair, as well as nails. Estrogens also contribute to hirsutism (the excessive growth of thick dark hair in locations where hair growth in women usually is minimal or absent), acne and changes in body composition. (Gruber C J, et al., Current concepts in aesthetic endocrinology. Gynecol Endocrinol. 2002 December; 16(6):431-41). The compositions in the present invention are additionally contemplated for use in hair loss and baldness in males which may be caused by hormones, diet, cancer, chronic illness or stress.

It is contemplated that the present invention can be used to regulate hair growth by stimulating or modulating hair follicle cells to either reduce or enhance or regenerate hair growth in desired areas by topical or sub-dermal applications.

This invention is also useful in the treatment of cellulite. Cellulite is a common term used to describe superficial pockets of trapped fat, which cause uneven dimpling or "orange peel" skin. It appears in 90% of post-adolescent women and is rarely seen in men. Common but not exclusive areas where cellulite is found, are the thighs, buttocks, and the abdomen. Contrary to popular belief, cellulite is not related to obesity, since it occurs in overweight, normal, and thin women. Cellulite can be aided by mechanized devices with motorized rollers and regulated suction. This non-surgical and non-invasive device creates a symmetrical skin fold, which allows for deep tissue mobilization to occur and results in reduction of cellulite and loss of inches. The present invention contemplates application of extracts topically or subcutaneously to regulate the distribution of subcutaneous fat deposits and improve the cosmetic appearance of areas affected by cellulite.

It is contemplated that the present invention may be useful for the repair or rejuvenation or de novo formation of damaged tissues, organs and cells beneath the skin, including all internal organs and tissues, including but not limited to muscle, fat, cartilage, bone, connective tissue, spleen, liver, pancreas, lungs and nervous tissue. Damages to the internal tissues or organs may be induced by i.e. accidents, diseases, medication, cancer, radiation and surgery.

When the body is exposed to high doses of radiation, a complex biological response is initiated that may lead to multi-organ failure (MOF). MOF begins with energy deposits in cellular targets and is propagated and amplified by the tissue response to cell damage. The biology of wound healing is at the root of MOF following surgical trauma, inflammation is the basis for MOF in sepsis, and the biology of the irradiated tissue initiates radiogenic MOF. Tissue response to radiation damage has been suggested to be initiated and co-ordinated by extracellular signaling. It has been demonstrated that transforming growth factor-β1 orchestrates the biology of irradiated tissue as a tissue level sensor of oxidative stress, and is integral to the cellular DNA damage response. (Barcellos-Hoff M H. How tissues respond to damage at the cellular level: orchestration by transforming growth factor-β (TGF-β British Journal of Radiology (2005) Supplement_ 27, 123-127).

M. Whole Cell Applications

In some embodiments of the present invention, compositions comprising intact stem cells (embryonic or adult) or cord-blood stem cells are utilized for cosmetic or therapeutic purposes. In some embodiments, suspensions of cells in fluid form are introduced to the skin. In some embodiments, suspensions of cells in fluid form are introduced into an open wound, and then covered by a wound dressing which can breathe (non occlusive). In some embodiments, an occlusive wound dressing is utilized. In some embodiments, one or more layers are utilized, for example a waterproof plastic membrane which can be glued onto skin, a layer of a nutrient gel which can nourish cells and speed wound healing (containing antibacterial agents, collagen modulating substances and other substances); and a layer of skin stem cells embedded in/placed on the nutrient layer, which are put in direct contact with the wound. In some embodiments, the cells are cultured in the lab from the person's own skin, adipose, or stem cells. In some preferred embodiments, the cells are then harvested and put in suspension, either to be applied as a fluid or placed on a plastic membrane with nutrient gel-layer to be applied to skin as an occlusive wound dressing/plaster/band-aid.

N. Ex vivo and in vivo Therapy

In some embodiments, the extracts are utilized for ex vivo treatment of cells derived from a patient. Briefly, cells are recovered from a patient, expanded, permeabilized, incubated with the extract, sealed, and then used for treatment of a patient. In this process, a number of the cells properties could be altered or enhanced, including but not limited to lengthening of telomeres—the terminal chromosomes protecting the central DNA contained in the chromosome which are shortened with each cell division -thus renewing and lengthening the life-span of the cell treated. Preferred methods are described in Example 3.

In some embodiments, the extracts are utilized in vivo on the patient's internal organs and/or tissues or cells. Briefly, the extract or components thereof could be injected to the intraperitoneal cavity, thus bathing the surface of abdominal organs including but not limited to the intestines, liver, spleen, pancreas, stomach and bladder thus inducing healing of wounds in these organs and tissues or aiding in regeneration of the cells which the organs and/or tissues are composed of.

It is also contemplated to introduce cells or extracts or components thereof into internal organs and/or tissues including but not limited to muscle, brain, fat, connective tissue, cartilage, pancreas, liver, spleen, heart and lungs as to induce de novo cell formation in tissues and organs and/or rejuvenate the cells from which the tissues/organs are composed. De novo cell formation occurs spontaneously in organisms including humans. De novo formation of local lymphoid tissue by dendritic dells which are the most potent professional antigen-presenting cells (Ludewig B et al., 1998 J Exp Med).

Life is manifested in growth. In plants, growth can be of two types, heterotrophic and autotrophic. Autotrophic growth uses inorganic material for nourishment. Heterotrophic growth is dependent on organic material for nourishment. During germination, seedlings usually grow heterotropically but once a plant becomes photosynthetic it can grow autotrophically—using minerals from the soil and atmosphere and sunlight for energy. Thus, for most of their life plants are autotrophic. However, there are some parasitic plants that grow heterotropically, obtaining inorganic material from their host. In plants, growth is serial, repetitive and plastic, and cell divisions contribute to de novo formation of organs all the way through to senescence. In animals, cell division serves to regenerate and maintain tissues and circulating cell populations, and growth is concurrently repetitive and dependent on the length of the telomeres which are shortened at each cell division.

This invention contemplates using both organic materials and inorganic materials contained in or added to extracts to nourish, stimulate and regulate cell growth, function and de novo formation in all organs and tissues. Plant seeds contain materials for heterotropic growth and are contemplated for use in extracts to aid cell growth in humans.

Certain animals have the ability to regenerate parts of their bodies after loss or injury. To actually regrow a lost organ or other structure rather than simply fill the void with scar tissue involves processes ranging from an injury response and wound healing to growth, patterning and differentiation of new tissues similar to that which occurred during embryonic development. With new evidence for the presence of stem cells in most if not all adult organs and their ability to participate in tissue repair, the field of regenerative biology has assumed much more widespread medical relevance (Stocum, 1995, 2004). If one looks at the phylogenetic distribution of regenerative ability in various organ systems, it appears that this capacity has been lost gradually in the course of animal evolution (Thouveny and Tassaya, 1998; Sanchez Alvarado, 2000). Regeneration of amputated limbs in amphibians is one of the best-studied model systems and a useful paradigm for understanding many features of vertebrate organ regeneration. As an example of "epimorphic" regeneration, this system includes cellular dedifferentiation in the injured tissues of the limb stump and proliferation of these cells to form a distal blastema that undergoes patterning and growth to restore the missing limb structures. The question of why limbs of phylogenetically advanced vertebrates fail to regenerate has been addressed by studies with limbs of anuran amphibians. Regeneration is excellent in the earliest stages of limb development in anurans (frogs and toads) but gradually diminishes as larvae approach metamorphosis (Dent, 1962). Limbs of adult anurans are incapable of complete regeneration.

However, urodele amphibians (newts and salamanders) commonly regenerate limbs and often other organs such as tails, jaws, and parts of the eye throughout their lifetimes. Such regenerative phenomena are very rare among reptiles, birds, and mammals as adults, suggesting that the loss of regenerative capacity may have been an adaptive part of the evolutionary transition toward the more advanced tetrapods, several investigators suggested that cells of differentiating muscle and other tissues in the anuran limb lose their ability to revert to the proliferative state and contribute to limb regrowth. Consistent with this view, regeneration and morphogenesis were found to be enhanced in limbs of adult frogs when tissue dissociation and cellular dedifferentiation were increased in stump tissues by additional trauma (Polezhaev, 1972). The plasticity of the differentiated state in regeneration-competent limbs and the potential of multinucleate muscle fibers to dedifferentiate and re-enter the cell cycle are currently active areas of investigation within the field of limb regeneration (Brockes et al., 2001; Brockes and Kumar, 2002).

Regeneration requires epithelial-mesenchymal interactions at the distal limb stump like those that drive embryonic limb development, and the changing nature of wound closure after amputation of anuran limbs during the transition from larvae to adults has also been studied. Closure of limb stumps in mammals involves contraction of full-thickness skin and in adult frogs involves rapid formation of connective tissue beneath the apical wound epidermis that initially covers the cut surface (Carlson, 1974). Tassaya and Olsen (1982) suggested that the inability of higher vertebrates to form a functional wound epithelium explains the lost potential for regeneration. Interfering with distal scar formation in amputated limbs of mammals or adult frogs in order to elicit regeneration have at best been only marginally successful (see review by Stocum, 1996), but the importance of establishing proper conditions for the reciprocal interactions between the apical epithelium and the underlying mesodermal cells is clear if a limb is to regenerate. In embryonic limbs, signaling occurs between the apical ectoderm and the adjacent mesodermal cells fibroblast growth factors (FGFs) and their receptors. Galis et al. (2003) have suggested that reason for the failure of limbs of higher vertebrates to re-establish functional tissue interactions is because limb regeneration is only possible when the limb develops as a semiautonomous module not dependent on interactions with transient structures such as somites.

Reptiles, birds, and mammals limb development begins in the early embryo and involves signaling interactions with various temporary neighboring structures, while in amphibians limb development occurs much later in development and is not coupled to interactions with transient structures. Factors and cells from the immune system may also affect regenerative ability (Harty et al., 2003). Development of adaptive immunity, which supplements more general and primitive innate immune mechanisms and allows an organism to acquire highly specific defense mechanisms against invading microorganisms, may have yielded immune cells and cytokines whose activity in traumatized tissue is inimical to cell dedifferentiation or the signaling required to initiate limb regeneration, so that the response to injury in the presence of such immunity is dominated by tissue repair and fibrosis rather than regeneration (Mescher and Neff, 2005).

The origin of adaptive immunity during evolution led to the restriction of regenerative ability is consistent with our knowledge of immune phylogeny (Flajnik et al., 2003). Invertebrates, which usually have well-developed capacities for regeneration, completely lack adaptive immunity. They rely instead on an array of defenses that constitute an extremely effective innate immune system. Mechanisms underlying acquired or adaptive immunity first appear in jawed vertebrates, becoming more efficient in various orders of fish and amphibians and highly developed in the homeotherms (Flajnik et al., 2003).

The present invention contemplates to increase the plasticity and alter the growth potential of cells and tissues by increasing cellular dedifferentiation and tissue dissociation, thereby allowing de novo generation of cells, tissues and organs. Alterations of immune-responses by active substances in the extracts are also contemplated.

EXAMPLES

Example 1

Cells and Cell Extracts

NCCIT, Jurkat (clone E6-1) and 293T cells (American Type Culture Collection, Bethesda, Md.) are cultured in RPMI 1640 (Sigma, St. Louis, Mo.) with 10% fetal calf serum (FCS), 2 mM L-glutamine, 1 mM sodium pyruvate and non-essential amino acids (complete RPMI). NIH3T3 Swiss-Albino fibroblasts (American Type Culture Collection) are cultured in Dulbecco's modified Eagle's medium (DMEM; Sigma) with 10% FCS, L-glutamine and 0.1 mM β-mercaptoethanol. Mouse ESCs are isolated from inner cell masses of strain sv129 blastocysts and plated on mouse fibroblast γ-irradiated feeder layers in ESC medium (DMEM, 15% FCS, 0.1 mM β-mercaptoethanol, non-essential amino acids, 1% penicillin/streptomycin) supplemented with 1,000 units/ml (10 ng/ml) of recombinant leukemia inhibitory factor (LIF; Sigma) on gelatin-coated plates. Prior to harvesting for preparing extracts, ESCs are passaged and cultured under feeder-free conditions in RPMI containing 10 ng/ml LIF.

To prepare NCCIT extracts, cells are washed in phosphate buffered saline (PBS) and in cell lysis buffer (100 mM HEPES, pH 8.2, 50 mM NaCl, 5 mM $MgCl_2$, 1 mM dithiothreitol and protease inhibitors), sedimented at 400 g, resuspended in 1 volume of cold cell lysis buffer and incubated for 30-45 min on ice. Cells are sonicated on ice in 200-μl aliquots using a Labsonic-M pulse sonicator fitted with a 3-mm diameter probe (B. Braun Biotech, Melsungen, Germany) until all cells and nuclei are lysed, as judged by microscopy. The lysate is sedimented at 15,000 g for 15 min at 4° C. to pellet the coarse material. The supernatant is aliquoted, frozen in liquid nitrogen and stored. Lysate of 95,583±10,966 NCCIT cells is used to generate extract. ESC extracts (25-30 mg/ml protein) are similarly prepared from LIF-adapted ESC cultures. 293T, Jurkat and NIH3T3 extracts are also prepared as above. If necessary, extracts are diluted with $H_2O$ prior to use to adjust osmolarity to ~300 mOsm.

Example 2

Bulge Hair-follicle Stem Cells

To isolate the vibrissa follicles, the upper lip containing the vibrissa pad of a subject is cut and its inner surface was exposed. In human individuals, hairs from the scalp or other haired body parts may be used instead of vibrissa. The vibrissa or hair follicles are dissected under a binocular microscope. The vibrissa are plucked from the pad by pulling them gently by the neck with fine forceps. The isolated vibrissae were washed in DMEM-F12 (GIBCO/BRL), containing B-27 (GIBCO/BRL) and 1% penicillin/streptomycin (GIBCO/BRL). All surgical procedures were done under a sterile environment. The vibrissa follicular bulge area contained nestin expressing cells. The cells were isolated by exposure to fluorescent anti-nestin antibodies under fluorescence microscopy. The isolated cells were suspended in 1 ml of DMEM-F12 containing B-27 with 1% methylcellulose (Sigma-Aldrich), and 20 ng-ml$^{-1}$ basic FGF (bFGF) (Chemicon). Cells were cultured in 24-well tissue-culture dishes (Corning) at 37° C. in a 5% $CO_2$/95% air tissue-culture incubator. After 4 weeks, the bulge-area cells form colonies.

Example 3

Ex vivo Therapy

Cells to be reprogrammed ex vivo are washed in cold PBS and in cold Ca2+- and Mg2+-free Hank's balanced salt solution (HBSS; Invitrogen, Gaithersburg, Md.). Cells are resuspended in aliquots of 100,000 cells/100 μl HBSS, or multiples thereof, placed in 1.5 ml tubes and centrifuged at 120 g for 5 min at 4° C. in a swing-out rotor. Sedimented cells are suspended in 97.7 ml cold HBSS, tubes placed in a $H_2O$ bath at 37° C. for 2 min and 2.3 ml SLO (Sigma; 100 mg/ml stock diluted 1:10 in cold HBSS) is added to a final SLO concentration of 230 ng/ml. Samples are incubated horizontally in a $H_2O$ bath for 50 min at 37° C. with occasional agitation and set on ice. Samples are diluted with 200 ml cold HBSS and cells are sedimented at 120 g for 5 min at 4° C. Permeabilization is assessed by monitoring uptake of a 70,000 Mr Texas red-conjugated dextran (Molecular Probes, Eugene, Oreg.; 50 μg/ml) in a separate sample 24 h after resealing and replating the cells. Permeabilization efficiency under these conditions is ~80%.

Following permeabilization, cells to be reprogrammed ex vivo are suspended at 1,000 cells/μl in 100 ml extract (or multiples thereof) containing an ATP-regenerating system (1 mM ATP, 10 mM creatine phosphate, 25 mg/ml creatine kinase; Sigma), 100 μM GTP (Sigma) and 1 mM of each nucleotide triphosphate (NTP; Roche Diagnostics, Mannheim, Germany). The tube containing cells is incubated horizontally for 1 h at 37° C. in a $H_2O$ bath with occasional agitation. To reseal plasma membranes, the extract is diluted with complete RPMI containing 2 mM $CaCl_2$ and antibiotics, and cells are seeded at 100,000 cells per well of a 48-well plate. After 2 h, floating cells are removed and plated cells are cultured in complete RPMI. The reprogrammed cells can be transplanted back into patient.

Example 4

Cream Base for Use with Cell Extracts

Water—78%
Proteins—10%
   e.g., Keratin, Filagrin, and/or Growth factors in trace amounts (μM-mM amounts of EGF, IGF, IGFII, Insulin, Substance P, Defensins, NGF)
Lipids -10%
   Squaline 9%, Aliphaic waxes 12%, Sterol esters 33%, Diol esters 7%, Triglycerides 26%, Free sterols 9%, Other lipids 4%.
Cell extract or egg extract or components of extracts -2%

A cream base made from any combination of lipids and/or proteins and/or water containing cell extracts.

Example 5

Preparation of Fish Egg Extracts

Fresh, unfertilized salmon (*Salmo salar*) eggs harvested from females in reproductive phase (late fall) are kept on ice, and the extract preferably made immediately. It is possible to freeze dry eggs in a cryoprotectant (e.g., 1.5 M 1,2-propanediol and 0.2 M sucrose) without disrupting the egg membrane. Freezing should be gradual (−1° C./min) to −80° C. Eggs should be thawed and kept on ice throughout the extract preparation procedure.

Eggs are washed twice in HBSS or seawater with protease inhibitors (10 ug/ml). The washing solution is removed and the eggs are lysed and homogenized in a pre-chilled Dounce glass-glass homogenizer. The lysate is transferred to Beckman Ultra Clear polyallomer centrifuge tubes (5 ml) while avoiding transfer of egg shells, and centrifuged for 15 min at 15.000 g at 4° C. in a Beckman ultracentrifuge using SW55T1 rotor. Three fractions are thereby obtained; lipid top fraction, cytoplasmic middle fraction, and a bottom fraction containing eggshells and nucleic debris. The cytoplasmic middle fraction is the collected extract. This extract is expected to contain most cytosolic organelles including mitochondria, lysosomes and peroxisomes, should be clear and viscous, and have an orange tint. Protease inhibitors (10 ug/ml stock) are added and extracts are kept at −80° C.

Further fractionation of the cytoplasmic extract is possible. Centrifugation at 100,000 g at 4° C. for 60 minutes yields 2-3 fractions, where the top/middle cytoplasmic fraction contains the cytosol with endoplasmic reticulum, SV and microsomes. The extract pH is measured by litmus paper, protein concentration measured by Bradford assay, and osmolarity measured by osmometer.

Mid-blastula Zebra fish embryos are collected, liquid removed and frozen to −20° C. To prepare the extract, embryos are thawed on ice, lysed and homogenized by Dounce glass-glass homogenizer in a small amount of either HBSS or seawater (preferably less than 50% liquid v/v). The lysate is filtered through a sterile linen cloth and centrifugated at 5,000 g at 4° C. for 20 minutes in a SX4250 rotor using a Beckman X-22R centrifuge. The cytoplasmic extract (supernatant) is collected and protease inhibitors (10 ug/ml) are added. The extract may be Millipore filtered (0.22 um MilliQ sterile filter). The extracts are kept at −80° C. The extract pH is measured by litmus paper, protein concentration measured by Bradford assay, and osmolarity measured by osmometer.

This general procedure is useful for the preparation of extracts from sea urchin, shrimp, fish eggs/roe or frog eggs. Briefly, roe collected from gravid female fish soon after they liberated their eggs in a spawning program (hCG hormone injected (1 ml/kg) at 6 to 8 hours before egg liberation, usually at dawn (2-4 am), or from gravid frogs. Roe/eggs are freeze dried or frozen at −20° C. or used fresh. Roe is collected from different kinds of fish. For sea-urchin, 0.5 M KCl is injected around the mouth to evoke shedding of eggs. The extract is prepared from eggs/roe by crushing (cell cracker or dounce-homogenization) or centrifugation at different speeds to separate cytoplasm with all content, with/without egg-shells (zona pellucida), with/without nucleus/cytosol, with/without organelles, with/without lipids. Further fractionation can be conducted to isolate one or more of mRNA, proteins, small peptides, carbohydrates and lipids. Major components of fatty acids in the roe are oleic acid, linoleic acid, and omega-3 fatty acids.

Upon application of the above protocol for salmon egg extracts, the salmon egg extracts had a surprisingly high protein concentration varying from 100-380 mg/ml, pH between 6.4-6.8, and an osmolarity of approximately 350 mOsm. The extracts were clear and viscous and non-filterable (by 0.45 um MilliQ filter). The protein in the extract precipitated easily upon addition of water or hydrous solutions with low buffering capacity due to the high protein content and low pH. Extracts could be neutralized to pH 7.0 by addition of alkaline (1-3 ul 1M NaOH/ml extract), whereupon dilution in water and hydrous solutions was possible. Zebra-fish extracts had a protein concentration varying from 23-26 mg/ml, pH between 6.4-6.8, and an osmolarity between 80-150 mOsm. The extracts were clear and non-viscous, filterable and diluted readily in water at all dilutions.

Example 6

Toxicity Testing of Extracts

Extracts with low pH and that contain certain substances may be toxic to cells. Toxicity of each batch should be tested on each cell type that is to be reprogrammed. Cells are harvested and washed twice in HBSS. Approximately 100,000 cells are pelleted and resuspended in 100 ul extract and incubated in a waterbath at 37° C. for 1 hour. Dilutions of the extracts may be tested to assess cell survival in extracts of varying protein concentration, pH and osmolarity. Optimally, protein concentration should be more than 25 mg/ml, pH should be close to 7.2, and osmolarity close to 280 mOsm. Cells and extract are incubated in wells with normal media (as suited to cell type chosen) for 24 hours, and the morphology of the cells inspected by microscopy. Cells are harvested, stained, and viable cells counted. If more than 50% of cells are non-viable after culture, the extract is considered toxic.

Upon application of the above protocol, 293T cells were viable for at least 3 weeks after incubation with extracts of salmon eggs and zebra fish embryo with protein concentrations varying from 24-380 mg/ml, at osmolarities between 140-350 and pH 6.9-7.7. At osmolarity below 140 mOsm, the cells died.

Cellular morphology of cells reprogrammed with salmon egg extracts or extracts of zebrafish embryos changed after approx. 3 days. 293T cells become rounder, and some populations of cells start to grow in blastoma like spheres. These changes are persistent, and can be observed until 21 days (experiment terminated), although in certain conditions the changes seem to reverse towards normal 293T morphology after 2 weeks. Upon culture of normal 293T cells with extract added to normal media (RPMI-1640 with 10% FCS and 0.2% extract), similar changes in morphology can be observed as seen for reprogrammed cells cultured in normal media. Additionally, cells cultured with salmon egg extracts in particular have an increased growth rate compared to normal cells. When starving cells (RPMI-1640 with 0.5% FCS), growth rate decreases significantly for non-extract treated cells, and morphology of cells changes slightly. For starved cells grown with extracts (0.2% extract in starvation media), the changes are more pronounced. In this case, most cell populations grow in blastomer like spheres, and the spheres detach from the culture vessel and float in the media, where they keep growing. Interestingly, the deceleration in growth rate is reversed in cells cultured with extract added to the starvation medium.

Example 7

Gene Expression Assays of Extracts

To verify extract expression of genes to be studied in reprogrammed cells, RT-PCR may be conducted on RNA isolated from extracts. RNA may be isolated from extracts by the method of choice, for example by using a Qiagen RNeasy Plus Kit (Qiagen). The RNA is quantified by spectrophotometer, and stored at −80° C. lug RNA is used for cDNA synthesis. cDNA synthesis may be conducted for example, by using the iScript cDNA Synthesis Kit (Bio-Rad), followed by PCR conducted with primers of choice. Positive controls are included for each primer set tested. PCR products are run on a 1% agarose gel with ethidium bromide and bands visualized by UV lamp.

Upon application of the above protocol, PCR products of extracts obtained by specific primers for human genes of interest as seen on agarose gels were compared to bands obtained from positive control human cell lines previously shown to express genes herein investigated (e.g., OCT4, NANOG, SOX2, UFT1, GAPDH, REX1 (a.k.a. ZFP42), LMN-A, LMN-B1, OXT2, AC133, APL and STELLA). Positive control NCCIT cells showed a single band at the expected size for each gene tested, while PCR products from neither salmon egg extracts nor zebra fish embryo extracts give bands on the gel. These results indicate that the extracts do not express the human gene variants detected with the primers used.

Example 8

Reprogramming of Cells with Fish Egg or Embryo Extracts

The cell type of choice (e.g., human 293T cells and adipose stem cells (ASC tested)) is harvested, kept on ice, and washed twice in ice cold HBSS. Approximately 100,000 to 500,000 cells are pelleted by centrifugation (300 g, 4° C. for 10 minutes). Cells may be permeabilized with streptolysin-O (SLO) by incubation for 50 minutes in a 37° C. waterbath prior to reprogramming, however this is not necessary for reprogramming effects of fish egg or embryo extracts. After SLO incubation, cells are washed in ice cold HBSS, centrifugated and excess liquid removed from pellet. Cells are resuspended in 100 ul extract per 100,000 cells and incubated for 1 hour at 37° C. in a waterbath. Approximately 100,000 cells are seeded in wells with complete media of choice. If SLO permeablization has been conducted, cells are cultured in media with 2 mM $CaCl_2$ for 2 hours after reprogramming to reseal the cell membranes. The media should be changed 2-12 hours after reprogramming. To assess extent of permeabilization by SLO, use epifluorescent microscopy for cells incubated for 50 min in 0 or 100 ng/ml SLO with 50 ug/ml Alexia red-conjugated dextran (10,000 $M_r$ or 70,000 $M_r$ dextran) to verify cell permeabilization and resealing.

Cells are cultured in wells until proliferation allows splitting to larger vessels. Split cells as appropriate for the cell type, but do not allow them to become confluent. Pellets for gene-analysis should be collected weekly and morphology assessed by phase-contrast microscopy at each passage. Cells can be cultured as long as desired, but to assess lasting reprogramming effects, 40 days is a suggested minimum.

Additionally, cells may be reprogrammed by incubation in media inhance with fish egg or embryo extracts. Cells are reprogrammed by adding 0.4% extract to normal complete medium (10% FCS) or starvation media (0.5% FCS). Cells of choice are grown to 50% confluency, and normal medium replaced with complete medium or starvation medium containing 0.4% extract. Split cells as appropriate with media containing extract. Fresh medium with extracts should be added to cells at least two times per week if splitting less than twice weekly. Pellets for gene-analysis should be collected weekly and morphology assessed by phase-contrast microscopy at each passage. Cells can be cultured as long as desired, but to assess lasting reprogramming effects, 40 days is a suggested minimum.

Upon following the protocols listed above, cells reprogrammed with fish-egg extracts or zebra-fish embryo extracts, or grown in media with extracts added, were harvested and RNA isolated. Reprogrammed or normal 293T cells were incubated in either complete media (RPMI-1640 with 10% FCS) with/without extracts (0.2%), or in starvation media (RPMI-1640 with 0.5% FCS) with/without extracts. Real-Time RT-PCR was run to study up- and down-regulation of differentiation marker genes. After 7 days, a pronounced up-regulation in the OCT 4 gene is seen in extract treated cells, and the changes are still seen after 17 days. Gene expression was calculated with the housekeeping gene GAPDH as reference of gene expression and can be seen in Tables 1 and 2. Values represent increase in gene expression in treated cells over untreated cells grown in normal media. Values given are for cells treated for 17 days, 17 days after reprogramming.

although not as marked (up to 4 times up-regulated). In these experiments, salmon egg extracts seem to give the largest rescue and up-regulation of the dedifferentiation-associated genes.

Replications of these reprogramming experiments in triplicate yielded results confirming that salmon egg extracts upregulate dedifferentiation associated genes, indicating increased "sternness" of the 293T cells.

Reprogramming was conducted by three different methods:
1. Reprogramming as described in methods, followed by normal cell culture;
2. Reprogramming as described followed by culture in media supplemented with 0.4% salmon egg extract (same as used for reprogramming); and
3. Normal cells not reprogrammed, cultured in media supplemented with 0.4% salmon egg extract (same as used for reprogramming).

All three methods yield changes in morphology and gene expression in cells, but at different levels and occuring at different times. Gene expression changes are seen at the same time as morphological changes are observed, varying from day 5 after reprogramming to day 28 after reprogramming. This seems to be dependent on the method used: reprogramming (methods 1 and 2) may yield more rapid changes than not-reprogramming and culturing in supplemented media (method 3).

TABLE 1

| Normal media 10% FCS | w/0.2% salmon egg extract | w/0.2% zebra fish embryo extract | Reprogrammed w/salmon egg extract | Reprogrammed w/zebra fish embryo extract | Reprogrammed w/salmon egg extract, grown with 0.2% extract | Reprogrammed w/zebra fish embryo extract, grown with 0.2% extract |
| --- | --- | --- | --- | --- | --- | --- |
| OCT4 | 59.78 | 100.58 | 34.98 | 18.20 | 82.26 | 90.12 |
| NANOG | 3.83 | 4.66 | 1.30 | 0.70 | 3.82 | 1.58 |
| SOX2 | 5.58 | 6.16 | 4.24 | 8.36 | 3.67 | 2.41 |

TABLE 2

| Starvation media 0.5% FCS | 293T cells, untreated | w/0.2% salmon egg extract | w/0.2% zebra fish embryo extract | Reprogrammed w/salmon egg extract | Reprogrammed w/zebra fish embryo extract | Reprogrammed w/salmon egg extract, grown with 0.2% extract | Reprogrammed w/zebrafish embryo extract, grown with 0.2% extract |
| --- | --- | --- | --- | --- | --- | --- | --- |
| OCT4 | 0.20 | 11.69 | 6.45 | 5.17 | 12.95 | 9.32 | 2.78 |
| NANOG | 0.14 | 0.51 | 0.41 | 0.37 | 1.10 | 0.32 | 0.14 |
| SOX2 | 0.63 | 4.34 | 1.67 | 2.66 | 2.47 | 4.49 | 1.12 |

Results show an up-regulation (18 to 100 times) of the OCT-4 gene in all cells treated with extracts compared to untreated cells. The changes in NANOG gene expression are more modest, with an up-regulation varying from none to 5 times. For SOX2 gene expression, the up-regulation seen varied from 2 to 8 times over basal.

In starved cells cultured without extracts, all OCT4, NANOG and SOX2 genes are down-regulated (0.2-0.6 times of normal 293T cells grown in normal medium). Adding 0.2% extract to the starvation media rescues the gene expression profile, and up-regulates OCT4 gene expression from 5 to 13 times over normal 293T cell expression—and up-regulation of approx. 100 times from untreated, starved 293T cells. The same is not seen for NANOG gene expression, where the down regulating effect of starvation is not rescued. For SOX2 gene expression, a rescue similar to that of OCT4 is observed, Reprogrammed cells with morphological changes and gene expression changes as shown below, were additionally labeled with OCT4 and NANOG antibodies and visualized with fluorescent secondary antibodies in a confocal microscope to verify increased expression of these genes.

Example results shown in tables 3 and 4 below, where numbers represent fold up- or downregulation of the dedifferentiation associated genes OCT4, NANOG and SOX2 as compared to normal 293T cells. Numbers below one indicate downregulation, and numbers over one indicate upregulation. ASC indicates adipose stem cells, only minor changes in gene expression can be detected. This is in agreement with experiments conducted with different extracts (unpublished observations, Taranger et al., 2006).

TABLE 3

| ASC REPROGRAMMING | DAY | OCT4 | NANOG | SOX2 |
|---|---|---|---|---|
| Reprogramming A1, normal media | 5 | 0.257 | 0.071 | |
| | 11 | 0.74 | 0.47 | 3.2 |
| | 19 | 0.78 | 1.17 | NA |
| | 40 | 1.27 | 0.22 | NA |
| Reprogramming A2, media with 0.4% extract | 5 | 0.88 | 0.17 | 2.81 |
| Reprogramming B1, normal media | 5 | 0.78 | 0.79 | NA |
| | 11 | 0.37 | 0.07 | 1.11 |
| | 18 | 2.25 | 1.91 | NA |
| | 35 | 1.27 | 0.12 | NA |

TABLE 4

| | DAY | OCT4 | NANOG | SOX2 |
|---|---|---|---|---|
| 293T CELL REPROGRAMMINGS | | | | |
| Reprogramming A1, normal media | 11 | 24.99 | 382.08 | 2.73 |
| | 25 | 2.77 | 19.54 | 7.01 |
| | 34 | 20.5 | 228.13 | 1.44 |
| | 42 | 1.31 | 0.82 | 3.27 |
| 293T | | | | |
| Reprogramming A2, media with 0.4% extract | 11 | 0.92 | 5.92 | 0.93 |
| | 25 | 0.9 | 0.76 | 0.99 |
| | 34 | 1.34 | 123.61 | 1.84 |
| | 42 | 8.14 | 2.69 | 6.55 |
| Reprogramming B1, normal media | 27 | 2.22 | 2.74 | 1.69 |
| Reprogramming B2, media with 0.4% extract | 27 | 2.51 | 3.28 | 1.80 |
| Reprogramming C1, normal media | 5 | 0.41 | 0.53 | 1.84 |
| | 11 | 0.61 | 0.56 | 1.73 |
| | 20 | 8.65 | 14.83 | 1.89 |
| | 28 | 125.70 | 18.03 | 84.69 |
| Reprogramming C2, media with 0.4% extract | 5 | 0.92 | 0.60 | 1.61 |
| | 11 | 0.65 | 1.10 | 1.17 |
| | 20 | 10.12 | 45.30 | 1.84 |
| | 28 | 2.25 | 0.79 | 5.61 |

The studies presented herein, give proper protocols for preparing fish egg extracts, characterization and toxicity tests of such extracts, protocols for cell reprogramming with the extracts, as well as results of changes induced by the extracts upon cells. The results include morphological changes presented as microscopic images, as well as changes in gene expression in the treated cells presented as real-time PCR data. Reprogramming of 293T cells has been conducted 17 individual times, with changes in morphology observed in 12 of the 17 reprogrammings. Alterations in gene expression has been observed in 8 of 12 studied (gene expression analysis for the reprogrammings is still under work). Alterations in morphology are correlated with changes in gene expression, i.e. changes in morphology occur at the same time as gene expression changes in the cells, and this is verified by immunofluorescent labeling of dedifferentiating genes in the reprogrammed cells. Reprogramming of adipose stem cells has been conducted 6 times, and morphological changes has only been observed in 1 of these. Only minor changes in gene expression changes in these reprogrammed cells can be detected.

Example 9

Morphological Changes in Cells Treated with Extracts

Morphology of cells reprogrammed with salmon egg extracts or extracts of zebra-fish embryos change after approx. 3 days. 293T cells become rounder, and some populations of cells start to grow in blastoma like spheres. These changes are persistent, and can be observed until 21 days (experiment terminated), although in certain conditions the changes seem to reverse towards normal 293T morphology after 2 weeks. Upon culture of normal 293T cells with extract added to normal media (RPMI-1640 with 10% FCS and 0.2% extract), similar changes in morphology can be observed as seen for reprogrammed cells cultured in normal media. Additionally, cells cultured with salmon egg extracts in particular have an increased growth rate compared to normal cells. When starving cells (RPMI-1640 with 0.5% FCS), growth rate decreases significantly (not shown) for non-extract treated cells, and morphology of cells changes slightly. For starved cells grown with extracts (0.2% extract in starvation media), the changes are more pronounced. Here, most cell populations grow in blastomer like spheres, and the spheres detach from the culture vessel and float in the media, where they keep growing.

Interestingly, the deceleration in growth rate is reversed in cells cultured with extract added to the starvation medium. Successful reprogrammings commonly grow in large clumps (>2 mm diameter) visible in the cell vessels with the naked eye.

Example 10

Alterations in Growth Patterns in Cells Incubated with Extracts 500,000 293T cells were seeded in medium sized round culture dishes, and incubated in normal media or media with addition of extract or starvation media. Cells were harvested after 24, 41, and 68 hours, counted and the growth rates were calculated. The results are presented tables 5 and 6.

TABLE 5

Calculate nr of cell divisions:
Number of cells (Ne) = Initial number of cells (No)/2^number of divisions (g)
g = (log Ne − log No)/0.301

| g = 24 H | 60314-24 log Ne | 060313 - 0 log No | |
|---|---|---|---|
| 2.3704 | 517000 | 100000 | 293norm |
| 2.018123 | 405000 | 100000 | 293Tnorm + LE |
| 1.613692 | 306000 | 100000 | 293Tnorm + ZE |
| 2.208113 | 462000 | 100000 | 293Tstarv |
| 2.170141 | 450000 | 100000 | 293Tstarv + LE |
| 2.3704 | 517000 | 100000 | 293Tstarv + ZE |

| g = 41 H | 60315-41 log Ne | 060373 - 0 log No | |
|---|---|---|---|
| 3.201953 | 920000 | 100000 | 293norm |
| 2.983975 | 791000 | 100000 | 293Tnorm + LE |
| 2.98215 | 790000 | 100000 | 293Tnorm + ZE |
| 2.29301 | 490000 | 100000 | 293Tstarv |
| 2.485675 | 560000 | 100000 | 293Tstarv + LE |
| 1.96367 | 390000 | 100000 | 293Tstarv + ZE |

| g = 68 H | 60314-68 log Ne | 060373 - 0 log No | |
|---|---|---|---|
| 5.883229 | 5900000 | 100000 | 293norm |
| 4.423347 | 2145000 | 100000 | 293Tnorm + LE |
| 5.919453 | 6050000 | 100000 | 293Tnorm + ZE |
| 2.406232 | 530000 | 100000 | 293Tstarv |
| 6.09864 | 6850000 | 100000 | 293Tstarv + LE |
| 3.322259 | 1000000 | 100000 | 293Tstarv + ZE |

TABLE 5-continued

Calculate nr of cell divisions:
Number of cells (Ne) = Initial number of cells
(No)/2 number of divisions (g)
g = (log Ne − log No)/0.301

| 24 h | 41 h | 68 h |
|---|---|---|
| min/generation = (T(hours) × 60)/g |  |  |
| Min/gen = |  |  |
| 607.4923 | 768.2811 | 693.4967 |
| 713.5343 | 824.4037 | 922.3786 |
| 892.3634 | 824.9083 | 689.2529 |
| 652.1406 | 1072.826 | 1695.597 |
| 663.5513 | 989.671 | 669.0016 |
| 607.4923 | 1252.756 | 1228.08 |

Generation time:
T: Time elapsed between No (near beginning of exponential growth) and Ne (near end of exponential growth)
Growthcurve: Log#cells

TABLE 6

| Condition | 0 H | 24 H | 41 H | 68 H |
|---|---|---|---|---|
| 293norm | 5 | 2.783541 | 2.88552 | 2.841044 |
| 293Tn + LE | 5 | 2.853415 | 2.91614 | 2.964909 |
| 293Tn + ZE | 5 | 2.950542 | 2.916406 | 2.838379 |
| 293Tstarv | 5 | 2.814341 | 3.030529 | 3.229323 |
| 293Ts + LE | 5 | 2.821874 | 2.995491 | 2.825427 |
| 293TS + ZE | 5 | 2.783541 | 3.097867 | 3.089227 |

Figure 2:
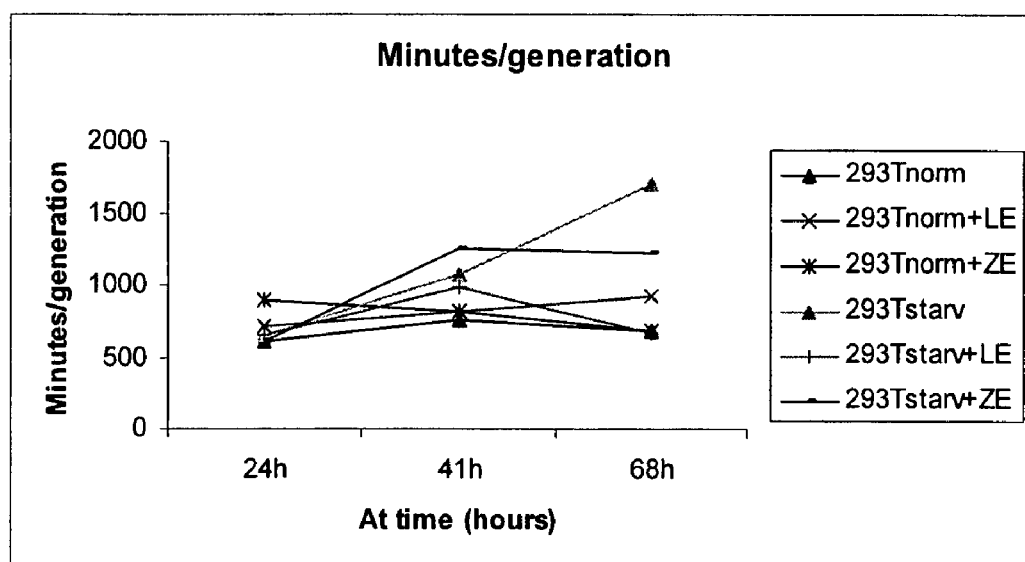
FIG. 2 is a graph of minutes/generation v. time.
Figure 3:
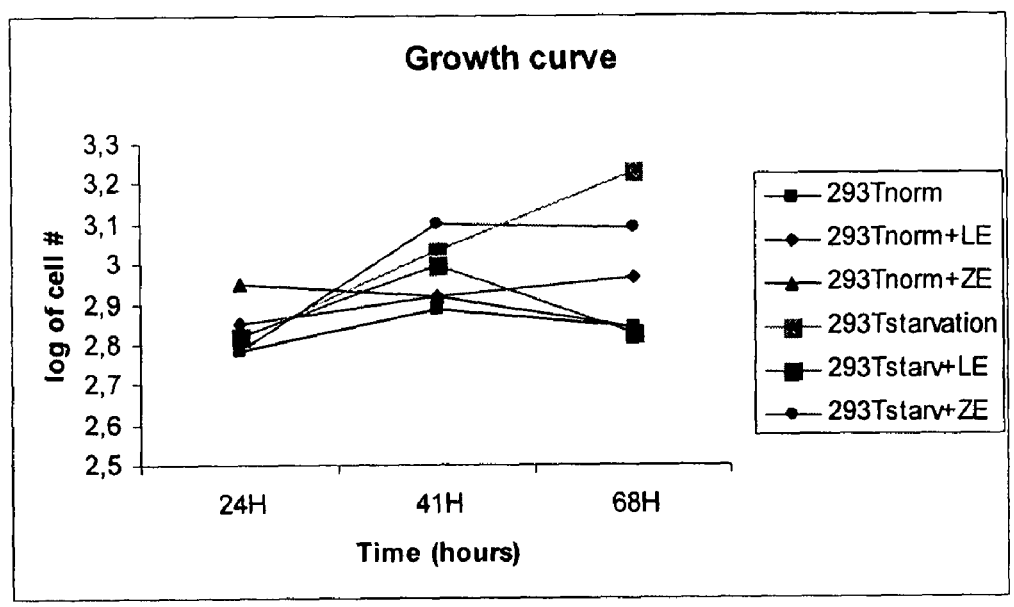
FIG. 3 is a growth curve graph.

Growth rate changes are seen, where starved cells grow much slower than cells in normal media throughout the study. This effect is rescued by addition of salmon egg media after 48 hours of culture. The cells grown in normal media with zebra-fish embryo extract and salmon-egg extract grow fastest of all the cells during the first 24 hours. See FIGS. 1-3.

Example 11

Enhanced Wound Healing with Salmon Egg Extracts

Aim of study: Investigate the effects of salmon egg extract developed on wound healing in the skin of mice.

Methods:

Summary: Two types of wounds were induced in the dorsal skin of mice. An excision wound of 1 cm diameter was induced on the left side of the back of each mouse (n=12 repeated 3×), and an incision wound of 2 cm length was induced on the right side of the back parallel to the spine. Half the mice (picked randomly) were treated with 30 ul salmon egg extract after wound induction and every 3 days for 12 days. The control group received no treatment. Wounds on all mice (treated and controls) were sprayed with liquid Band-Aid on day 1 in one of the 3 repetitions, but this did not affect the differences seen between the control and treated mice as observed in all 3 experiments (with/without spray bandage).

In each experiment, mice were divided in 3 cages, each with 2 controls and 2 treated animals. The wound healing process was monitored over 12 days, with measures taken including wound areas, days until complete healing (reepithelialization and loss of scab), and size of resulting scar. Biopsies were taken on day 1 and day 12 for further analysis, and wounds were photographed regularly to document healing progress.

Materials:
Mice: A/J or NMRI albino males.
Ethanol for sterilization of skin prior to wound induction.
Small surgical scissors and micro scissors, surgical blades and tweezers.
Salmon egg-extract, batch LE4, prepared as described above.
Isofluran gas: FORENE Isofluran Vnr 506949, lot 22397VA, exp 2009-10 (Abbott, Solna, Sweden)
Vaporizer: Datex-Ohmeda Isotec 5
Liquid nitrogen for biopsy samples.
4% PFA (in PBS) for biopsy samples.
Digital camera to take pictures of wounds and skin during healing.
1 cm diameter round mold for inking on wound size in animals.

Study Design:

Animals. Healthy inbred male NMRI or A/J mice (separate studies), weighing between 25 g and 35 g were obtained from the animal house of the Institute of National Public Health, Oslo, Norway. The mice were acclimatized for one week prior to the experiments, and housed in polypropylene cages on normal food and water ad libitum, and were ear-labeled (1-4 in each cage) one week prior to start of the experiments. Animals were periodically weighed before and after experiments. The mice were anaesthetized prior to infliction of the experimental wounds. The surgical interventions were carried out under sterile conditions using isofluran gas (oxygen+ isofluran mixed in vaporizer). Animals were closely observed for any infection; those which showed signs of infection were separated and excluded from the study. An acute toxicity study was conducted for the extracts as described elsewhere in this patent. The study was approved by the Ethics Committee of Norway.

Wound healing activity. Excision and incision wound models were used to evaluate the wound-healing activity of salmon egg extracts. Each animal received an excision wound on the right side of the back, and an incision wound on the left side on the back. The wounds were induced on day 1 and the study terminated on day 12.

Excision and incision wounds. Each mouse was inflicted with one excision wound (Morton J J P, Malone M H. Evaluation of vulnerary activity by an open wound procedure in rats. Arch Int Pharmacodyn. 1972; 196:117-126) and one incision wound (Ehrlich H P, Hunt T K. Effect of cortisone and vitamin A on wound healing. Ann Surg. 1968; 167:324-328.). The mice were anaesthetized prior to creation of the wounds, with isofluran gas (by mask, system details below). The dorsal fur of the animal was shaved with electric clipper and the area of the excision wound to be created was outlined on the left side of the back of the animals with waterproof, permanent marker. An excision wound of 1 cm in width (circular area=0.785 cm2) of full skin thickness (app. 1 mm) was created along the markings using toothed forceps, a surgical blade and pointed scissors, the entire wound left open. On the right side of the spine, a longitudinal paravertebral incision of 2 cm long was made through the skin and cutaneous tissue on the back. The groups of experimental animals were treated with aqueous salmon egg extracts (30 ul), topically applied to the wound every third day. The control group wounds were left untreated.

The parameters studied were wound closure, wound size, scar size, epithelialisation time, and histology (morphological parameters of the skin). The measurements of the wound areas of the excision wound model were taken on 1st, 5th, 9th and 12th day following the initial wound using transparent paper and a permanent marker. The wounds on each mouse were photographed daily with a digital camera (see details below). The period of epithelialisation was calculated as the number of days required for the wounds to become scab free.

Biopsies. On day 1, the skin excised in the creation of the excision wound was kept as a normal skin biopsy, allowing each animal to be its own control in later biopsy analysis. One half of the biopsy was fixed in 4% PFA, the other snap-frozen in liquid nitrogen. In the excision and incision wound model, granulation tissue formed on the wound was excised on the 12th postoperative day, after the termination of the animals by cervical dislocation or CO2 gas. Excision and incision wounds were surgically removed along the initial wound induction markings. One half of the biopsy was fixed in 4% PFA, the other half snap-frozen in liquid nitrogen for later analysis.

Histopathological analysis of biopsies. Half of the healing tissues obtained on the 12th day from all animals in the excision and incision wound model was fixed in paraformaldehyde (4% in sodium-phosphate buffer) for 2 hours at room temperature and stored at 4 degrees centigrade, sectioned on a cryostat antiparallel to the skin surface. Sections were stained with H&E and parameters of the scar, including the thickness of the granulation tissue, were measured in the microscope.

Standard procedure for H&E staining was conducted. Briefly, 10 um cryostat sections of mouse skin biopsies (on SuperFrost Plus slides) were rehydrated (from absolute through 96% and 70% ethanol) before coloring with hematoxylin (7 min) (Sigma 51275 HEMATOXYLIN SOLUTION ACC. TO MAYER), washed in running water (5 min), colored with eosin (1 min) (Sigma HT110116 EOSIN Y SOLUTION ALCOHOLIC), rinsed shortly in water and dehydrated (from 70% through 96% to absolute ethanol followed by 2×5 min in xylol). Sections were mounted directly from xylol with Eukitt (Sigma 03989-100 ML EUKITT® QUICK-HARDENING MOUNTING ME-DI).

H&E stained sections of mouse skin biopsies taken at day 1 (at time of wound induction) and day 12 (post healing) from representative treated and control animals were studied in the light microscope, digital pictures taken with the 4×, 10×, 20× and 40× objectives and measures of skin thickness and scar parameters were taken from the digital images.

Immunolabeling of cryostat sections of mouse skin biopsies. Sections of excision wound biopsies taken at day 1 and day 12 of representative extract treated and untreated controls were doubly immunolabeled as previously described (Boulland et al. Expression of the vesicular glutamate transporters during development indicates the widespread corelease of multiple neurotransmitters. J Comp Neurol. 2004 Dec. 13; 480(3):264-80) with antibodies against either NANOG (rabbit polyclonal, Abcam) and calbindin (mouse, Abcam) or OCT3/4 (rabbit polyclonal, Santa Cruz) and calretinin (goat, Chemicon) to look for increased expression of stem cells (as indicated by presence of NANOG and OCT3/4) in the healed wounds.

Results

Healing rates of wound treated with salmon egg extract compared to untreated controls.

Figure 4:
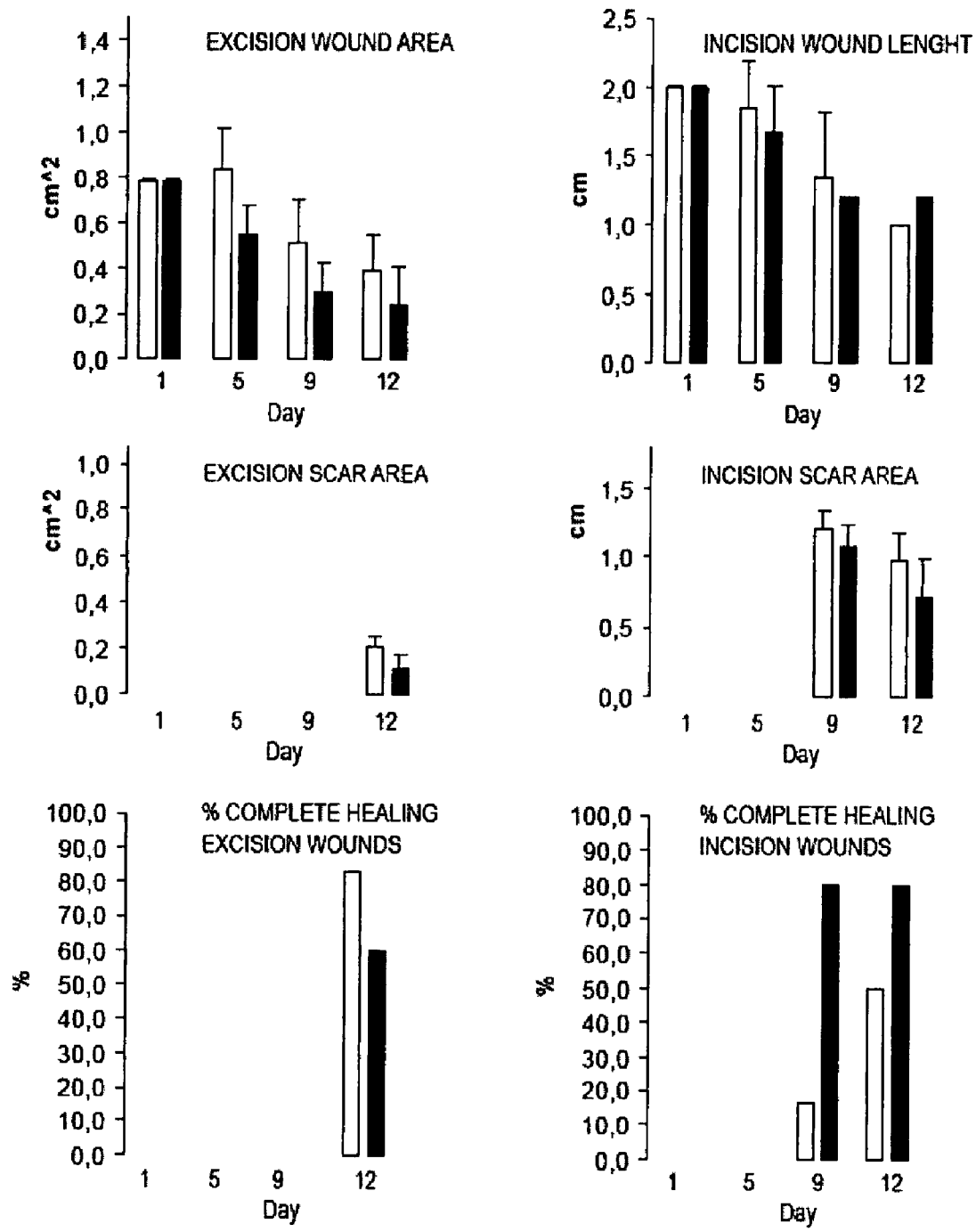
FIG. 4 provides graphs of mice skin wound and scar measurements measurements and wound healing rates. These data show that the wound healing extract has an effect on healing of two types of wounds (excision wounds left panels, incision wounds rights panels) in mouse skin. Measures taken by ruler and wound/scar area traced on transparent film at day 1, 5, 9 and 12. Areas of excision and length of incision wounds (top panels) show a gradual reduction in wound area from day 1 to 12. The healing starts earlier and the wound reduction is more rapid in extract treated animals, significant at day 5 and 9 for excision wounds. Scars formed were measured from day of reeptheilization (middle panels). A tendency to smaller wound sizes is seen for both excision and incision wounds. Day of complete healing taken as day scab falls wound is revealed. The percent of animals with completely healed wounds (bottom panels) show more rapid healing in the treated animals for the incision wounds.

Visual appearance of treated and untreated skin wounds. Results indicate a speedier wound healing in the extract treated animals (images not shown), with significant differences at day 9 and 12. Furthermore, wound sizes reduced more rapidly reduced in the extract treated animals, with significant differences at day 5 and 9. See FIG. 4.

Hematoxylin-Eosin staining of skin biopsies for histological examination (paraffin embedded or cryostat sections). Biopsies taken from the skin removed to form the excision wound at day one and comparable biopsies of the same area taken at day 12 from 6 animals were cryostat sectioned, stained with H&E and microscopy images were taken and analyzed. Morphologically, sections of biopsies of normal skin from day 1 of the control and treated animal groups were similar, with equal measures of skin parameters. At day 12, the scar tissue, particularly the collagen organization, appeared more disorganized in the control animals compared to the extract treated animals.

TABLE 7

| | Total skin thickness (um) | Epidermal thickness (um) | Dermal thickness (um) | Wound/scar diameter (um) | Distance between hair sacs (um) |
|---|---|---|---|---|---|
| Controls | | | | | |
| Day 1 | 391 | 15 | 340 | 10000 | 254 |
| Day 12 | 1154 | 63 | 838 | 1913 | 144 |
| Treated | | | | | |
| Day 1 | 389 | 17 | 326 | 10000 | 218 |
| Day 12 | 989 | 46 | 780 | 2113 | 157 |

Measurements (average of 3 independent measurements per section) were taken as follows: Epidermal thickness was measured from the stratum germinatum (basal keratinocytes) to the stratum corneum. Dermal thickness was measured from below the stratum germinatum to the subcutis (adipose tissue below dermis). Total skin thickness was measured as combined thickness of epidermis and dermis. The scar diameter at day 12 was measured between the wound healing tongues on either side of the scar tissue, and compared to the day 1 excision wound diameter (1 cm). Distance between hair sacks was measured between the centres of the hair papillae of adjacent hairs (proximal to the scar at day 12).

The measurements show that there is less variance in scar thickness, diameter, epidermal and dermal thickness in treated animals compared to the untreated controls. The extract treated animals displayed a more normal epidermal thickness (closer to epidermal thickness as measured in the same animals at day 1), and the distance between the newly formed hair sacs proximal to the scar were more evenly distributed (more similar to hair sack distribution in normal skin at day 1), while the hair sacs of the healed skin in control animals was more disorganized and distributed with a smaller distance between hair sacs compared to normal skin.

In summary, the data show that extract treated animals have 41% thinner scar (total skin thickness at centre of scar) compared to untreated controls, and the newly formed epithelium in the healed skin is 148% thinner, and the new dermis 7% thinner in treated animals compared to untreated controls. Additionally, the diameter between new hair sacs is 16% closer to pre-operative distance in treated animals compared to untreated controls.

Immunolabeling of cryostat sections of mouse skin biopsies. Sections of excision wound biopsies taken at day 1 and day 12 of representative extract treated and untreated controls were doubly immunolabeled as previously described (Boulland et al.) with antibodies against either NANOG (rabbit polyclonal, Abcam) and calbindin (mouse, Abcam) or OCT3/4 (rabbit polyclonal, Santa Cruz) and calretinin (goat, Chemicon) to look for increased expression of stem cells (as indicated by presence of NANOG and OCT3/4) in the healed wounds.

OCT3/4 is a marker of embryonic and other stem cells, found predominately in the nucleus. OCT4 (green) staining was detected in the basal layer of epidermis (proliferating keratinocytes) (novel finding). Interfollicular keratinocytes in culture have previously been transfected with OCT-4 which resulted in increased expression of Sox-2, Nanog, Uft1 and Rex-1.

NANOG expression often follows the expression of OCT4 in stem cells. NANOG labeling was detected at the base of hair sacks (hair stem cells) as well as in migrating cells along the wound healing tongue at day 12 (novel found).

CALRETININ is a calcium-binding protein shown to be present in the companion cell layer of the human hair follicle. Calretinin staining was seen along the hair shafts as expected.

CALBINDIN is found in the nucleus and cytoplasm of epidermal keratinocytes (higher in nucleus than in cytoplasm). Upon wounding, the levels of calbindin in the nucleus drop for approx. 10 days post wounding. Calbindin labeling was seen in keratinocytes (epidermis and layer around hair shafts).

Further analysis using Z-stacks and Fourier transformation with confocal microscope will be necessary to look for differences between the treated wounds and the untreated controls.

Example 12

Reprogramming of Human Skin Fibroblasts and HEK Cells

Subculture of hsF Cells (Human Skin Fibroblasts).
  Complete media for hsF
    500 ml DMEM F-12 (+Glutamax)
    50 ml (10%) FCS (Fetal Calf Serum—heat inactivated)
    5 ml (1%) PenStrep
  Starvation media for hsF
    500 ml DMEM F-12 (+Glutamax)
    5 ml (1%) PenStrep
  Culture the cells in large flasks (162 cm2)—ca 1 mill cells per large flasks at confluence, or on coverslips in wells for reprogramming. (hsF cells used were from ACCT).
Subculture hsF Cells:
  1. Rinse the cell layer twice with 10-15 ml PBS to remove all traces of serum.
  2. Add 2 ml Trypsin-EDTA solution until cell layer is dispersed (5-7 minutes).
  3. Add min 4 ml media and aspirate cells by gently pipetting.
  4. Subculture ratio 1:2-1:4; Add 2-3 ml of the cell suspension to the flask and fresh media to total 25 ml. Subculture the cells 1:2 to 1:4 every 2 to 3 days—e.g. 1:4 twice a week.
Freeze Cell-pellet:
  1. Make fresh freeze-media:
    a. Normal media with 20% FCS and 10% DMSO
  2. Follow the protocol above (subculture) to point 3; thereafter
  3. Transfer cells to a 50 ml Nunc-tube and spin at 300 g (1500 rpm), 10 min 4 C.
  4. Resuspend cells to 1 million per 1 ml freeze media and aliquot 1 ml to Nunc cryo tubes.
  5. Freeze the cells in Mr. Frosty-box with isopropanol at −80° C. over night (−1° C./min).
  6. Transfer to nitrogen tank.
Make Pellets for RNA-isolation:
  Follow the subculture protocol to point 3; thereafter
  1. Transfer cells to a 50 ml Nunc-tube and spin at 300 g (1500 rpm), 10 min 4 C.
  2. Wash cells in one ml ice cold PBS per million cells and spin at (300 g, 10 min 4° C.).
  3. Resuspend the pellet in the same amount PBS and add 1 ml to eppendorf tube for RNA pellets.
  4. Spin at 300×g 10' at 4° C.
  5. Aspirate PBS.
  6. Keep pellet on ice and snap-freeze in liquid N2.
  7. Transfer to −80° C.-freezer.

Reprogramming hsF on Coverslips, Including SLO

Objective: To reprogram cells with a nuclear-free extract to alter gene expression, morphology and elements of growth and to study changes in state of differentiation.

Materials: hsF cells grown in 24-well plate on coverslips (ca 100.000 cells sown out per well in starvation media ca 5 days earlier and ca 50.000 cells sown out per well in normal media ca 3 days earlier); Extract (salmon egg extract); Incubation in media for control; 1×PBS; $Ca^{2+}$ free Hanks Balanced Salt Solution (HBSS) at 4° C.; TE to loosen hsF cells from flask; SLO stock of 100 µg/ml diluted 1:100 in HBSS; ATP (200 mM stock in water); GTP (10 mM stock in water); Phosphocreatine (2M stock in water); Creatine kinase (5 mg/ml stock in water); Autoclaved MQ water; Waterbath at 37° C.; $CaCl_2$ (2 mM) enriched medium: 1001 mM CaCl2 stock is prepared by mixing 1.67 g CaCl2 with 15 ml distilled water and sterile filtered. 2 mM concentration of $CaCl_2$ is made by e.g. mixing 50 µl of 100 mM CaCl2 with 2450 µl of reprogramming medium.

Procedure:

Wash cells twice in ice cold 1×PBS (1 ml). Wash cells twice in cold HBSS (1 ml). Preheat samples in incubator, 37° C., 2-3 min and remove HBSS. Add 110 µl HBSS and 90 µl SLO (to a final SLO concentration of 450 ng/ml) and mix. Add 200 µl HBSS to control wells without SLO. Incubate in incubator 30 min, tilt the plate every 10 min. Remove the SLO (keep one parallel where SLO remains in the well). Prepare extract for reprogramming: One reprogramming reaction contains 250 ul extract (to 50-100K cells) Prepare ATP generating system, keep on ice: mix ATP, GTP, creatine kinase, phosphocreatine in 1:1:1:1 ratio, keep on ice. Add 12.5 ul ATP generating system per reaction to the extract. Add 250 µl salmon egg extract (with ATP-generating system). Make sure the extract covers the cells on coverslips. Mix by tilting the plate. Incubate in incubator 60 min, tilt the plate every 10 min. Aspirate the extract (200 µl) and add Ca-enriched medium to each well (ca 1500 µl). Incubate for 2 h. Check in microscope if cells have attached to coverslips. If so, remove Ca-containing medium and add complete medium (ca 500 µl). Incubate 37° C., 5% CO2. Assess cells within 24 hours culture. Phase contrast microscopy. Split cells before confluence is reached. Coverslips were moved to new wells one day after reprogramming, and some coverslips were trypsinated to be moved to small bottles. Since cells didn't loosen, the entire coverslip was moved to the bottle.

Results—hsF Reprogramming

Reprogramming experiments RPE (starvation media) and RPF (normal media).

Changes in Gene Expression:

TABLE 8

Fold upregulation of the developmentally regulated OCT4 and NANOG genes, relative to GAPDH, as assessed by qPCR.

|  | OCT4 | NANOG |
|---|---|---|
| RPE 1&2 | 150.71 | 10.14 |

Morphological Changes of Cells

After reprogramming, cell cultures were assessed by phase contrast microscopy and compared with normal cells.

One day after reprogramming, a population of the surviving cells resembled normal hSF cells, while a subpopulation of cells displayed altered morphology. These cells appeared longer/more stretched than normal cells and some (especially those from starvation media) showed circular vesicles/bodies in the cytoplasm. More cells survived from the starvation media than from the normal media.

From day 12 to day 22 after reprogramming (experiment terminated on day 22), cells that were still attached to coverslips showed an unusual morphology, with a larger and more distinct nucleus having thin "offshoots"/"spurs" and cells having a different shape than normal cells. A subpopulation of cells (mainly starved cells) still had circular vesicles/bodies inside the cytoplasm. As complete reprogramming of all cells in each experiment is not expected (Taranger et al., 2005), the subpopulation of cells showing altered morphology probably represent reprogrammed cells which are responsible for the alterations of gene expression detected by qPCR.

Immunofluorescence.

Cells were fixed on coverslips on day 7 after reprogramming. Immunofluorescence labeling was conducted basically as previously described for tissue sections (Boulland et al., 2004). Briefly, cells grown on coverslips were fixed in 4% PFA (30 min RT), washed in PBS, blocked with 1M ethanolamine, washed in 3×PBS, preincubated in block solution (1 hr RT), incubated with primary antibodies against OCT 3/4 (Santa Cruz) (1:200) in incubation solution (3 hrs RT), rinsed in 3×PBS and incubated with fluorescence-coupled secondary antibodies Alexa 488 (1:2000) (Molecular Probes)(1 hr RT) and finally rinsed in 3×PBS. To stain nuclei, DAPI (1:1000) was added to second to last rinse. Coverslips were mounted with ProLong Gold Antifade reagent (Molecular Probes) and images were taken with a fluorescence microscope (Olympus) or confocal microscope (Zeiss).

OCT4 staining was seen in the cytoplasm of most cells, stronger labeling was seen in the reprogrammed cells compared to the normal control, which showed very weak staining. Hoechst staining was observed in the nuclei of normal cells, additionally overlapping with OCT4 staining in the cytoplasm of the reprogrammed cells. The cells were assessed for infection to ensure the cytoplasmic Hoechst stain was not caused by mycoplasma but rather a true expression of reprogramming.

Subculture of HEKa Cells (Human Epidermal Keratinocytes—Adult)

Keratinocyte Culture Systems from Cascade Biologics
EXTENDED-LIFESPAN SYSTEMS
Basal Medium EpiLife® Medium
   Growth Supplement HKGS (S-001-5)
   Subculture Reagent Trypsin/EDTA (R-001-100)
   Subculture Reagent Trypsin Neutralizer (R-002-100)
   Antibiotics (after reprogramming) Gentamicin/Amphotericin B (R-015-10)
   Expected lifespan from HEKa (C-005-5C) 35-45 population doublings Complete media for HEKa
   500 ml EpiLife Medium
   5 ml HKGS (Human Keratinocyte Growth Supplement)
   After reprogramming: 1 ml Gentamicin/Amphotericin (GA)

Culture the cells in 75 cm2 culture flasks—ca 10 mill cells at confluence.

Subculture HEKa Cells
1. Quickly rinse cells with 3 ml of Trypsin/EDTA.
2. Add 1 ml of fresh Trypsin/EDTA and incubate until the cells are dispersed (8-10 min).
3. Add 3 ml of Trypsin Neutralizer solution and transfer the cells to a sterile 15 ml tube. Repeat with additional 3 ml additional Trypsin Neutralizer.
4. Centrifuge at 180×g for 7 minutes.
5. Resuspend the cell pellet and seed new culture vessels with 2.5×103 cells/cm2.
6. Change media on cells after 48 hours
7. Change the medium every other day until the culture is approximately 50% confluent.
8. Change the medium every day until the culture is approximately 80% confluent.

Freeze Cell-pellet:
7. Make fresh freeze-media:
a. Normal media added 10% FCS and 10% DMSO
8. Follow the above protocol (subculture) to point 4.
9. Wash cells with PBS (180×g, 7 min)
10. Resuspend the cell pellet to 1 million per 1 ml freeze media and add 1 ml to cryo tubes.
11. Freeze the cells in Mr. Frosty-box with isopropanol at −80° C. over night (−1° C./min).
12. Transfer to nitrogen tank.

Make Pellets for RNA-isolation:
Follow the subculture protocol to point 4; thereafter
8. Resuspend cells to 1 million per 1 ml PBS and add 1 ml to eppendorf tube for RNA pellets.
9. Spin at 300×g 10' at 4° C.
10. Aspirate PBS, keep pellet on ice and snap-freeze in liquid N2.
11. Transfer to −80° C.-freezer.

Reprogramming of HEKa Cells (without SLO)

Objective: To reprogram cells with a nuclear-free extract to alter gene expression, morphology and elements of growth and to study changes in state of differentiation.

HEKa cells used for the experiment were grown in their normal media (EpiLife with HGKS and alternatively 1% GA [after reprogramming]). "Mock" reprogramming was conducted as control (cells undergo reprogramming procedure in normal media without extract added) and normal HEKa cells were cultured in parallel as negative control.

293T were reprogrammed in the same experiment, also including one mock reprogramming and 1 flask of normal 293T as controls. 293T are grown in their normal media (RPMI with 1% PS).

Materials: 1 flask HEK cells; 1 flask 293T; Extract (salmon egg extract) Incubation in media for control; RPMI medium (293T); EpiLife Medium (HEK); 1×PBS; $Ca^{2+}$ free Hanks Balanced Salt Solution (HBSS) at 4° C.; TE to loosen HEK cells from flask; TN (Trypsin Neutralizing) solution; ATP (200 mM stock in water); GTP (10 mM stock in water); Phosphocreatine (2M stock in water); Creatine kinase (5 mg/ml stock in water); NTP (25 mM stock); Autoclaved mq water; 75 cm2 flasks; 15 ml, 1.5 ml tubes Centrifuge cooled to 4° C.; Swing out bucket rotor for 1.5 ml tubes, and for 15 ml tubes Waterbath at 37° C.

Procedure:
1. Harvest HEK cells—wash with 1 ml TE, aspirate and incubate with 3 ml TE for 5-10 min Transfer cells into 15 ml tubes and spin at 200×g, 10 min 4 C. (Harvest the 293T cells—wash with PBS, add 10 ml RPMI media, loosen cells and transfer to 50 ml tube).
   a. Wash once in 30 ml ice cold PBS and one in 10 ml ice cold HBSS
   b. Resuspend cells to 500.000 per 1 ml HBSS 2. Add 500 000 cells into each reprogramming tube
  a. Spin 1200 rpm, 5 min 4° C. in SW rotor
  b. Remove HBSS
3. Prepare extract for reprogramming
  a. Prepare ATP generating system, keep on ice: mix ATP, GTP, creatine kinase, phosphocreatine in 1:1:1:1 ratio, keep on ice. +0.5 mM NTP per reaction
  b. Add 30 ul ATP generating system per reaction
4. Add extract (with ATP-generating system), 500 ul to 500.000 cells per tube.
  a. Cover tubes with parafilm and incubate for 60 min in waterbath at 37° C. Flick cells twice during incubation.
5. Add one reprogramming tube per flask with medium.
6. Incubate 37° C., 5% $CO_2$ Assess cells within 24 hours culture. Phase contrast microscopy. Split cells before confluence is reached.

Results: HEKa Reprogramming

Reprogramming experiment RPH.

Changes in Gene Expression:

TABLE 9

Fold upregulation of the developmentally regulated OCT4 and NANOG genes, relative to GAPDH, as assessed by qPCR.

|  | OCT4 | NANOG |
|---|---|---|
| RPH mock d13 | 1.29 | 1.26 |
| RPH3 d13 | 4.13 | 13.45 |

Morphological Changes of Cells:

After reprogramming, cell cultures were assessed by phase contrast microscopy and compared with normal cells.

Fewer cells incubated with extract survived the reprogramming procedure than control mock cells. Some reprogrammed cells showed circular vesicles/bodies inside the cytoplasm and possibly larger and less defined nuclei. Some of the cells showed an atypical morphology with small "spikes" resembling podocytes protruding from the plasma membrane and having a different overall shape than normal cells.

Immunofluorescence

Cells were fixed on coverslips on day 9 after reprogramming. Immunofluorescence labeling was conducted as described for hSF cells.

HEK cells were immunolabeled for OCT4 (same procedure and antibody as for hSF cells) and nuclei identified by Hoechst stain in a fluorescent microscope. Normal HEK cells showed very weak OCT4 staining in the nuclei, while nuclei of a subpopulation of HEK cells reprogrammed with salmon egg extract were clearly more strongly stained with OCT4, in agreement with qPCR results showing an upregulation of OCT4 in cells from the same reprogramming. Hoechst staining was overlapping with OCT4 staining in the nuclei of most cells, and OCT4 staining was especially strong in the nucleoli of the reprogrammed cells. Negative controls (primary antibody omitted) showed no OCT4 staining while nuclei were normally stained by Hoechst. Identical settings for microscope and digital image capture were used when observing cells.

The invention claimed is:

1. A composition comprising an isolated water soluble cytoplasmic fraction of salmon eggs comprising protein and messenger ribonucleic acid, wherein the protein content of said cytoplasmic fraction is about 100 to 380 mg/ml and a lipid component from a different source than said salmon eggs.

2. The composition of claim 1, further comprising an epigenetic inhibitor.

3. The composition of claim 1, wherein said composition is provided in a cream, gel, emulsion, ointment, spray, powder or lotion.

4. A composition comprising an isolated water soluble cytoplasmic fraction of salmon eggs comprising protein and messenger ribonucleic acid, wherein the protein content of said cytoplasmic fraction is about 100 to 380 mg/ml, in a cream, gel, spray, emulsion, solid, plastic or matrix, ointment, powder or lotion suitable for topical administration.

5. The composition of claim 4 wherein said composition further comprises purified or synthetic nucleic acid sequences, polypeptides, or natural products or combinations thereof.

6. The composition of claim 4 wherein said composition further comprises an epigenetic inhibitor.

7. The composition of claim 4, wherein said composition further comprises a lipid or protein fraction from a source other than said salmon eggs.

8. The composition of claim 7 wherein the lipid fraction comprises squalene, an aliphatic wax, a sterol ester, a diol ester, a triglyceride, or a sterols or combinations thereof.

9. The composition of claim 4 wherein said composition further comprises keratin or filaggrin.

10. The composition of claim 4 wherein said composition further comprises glutamine, antiinfective agents, anti-inflammatory agents, antioxidants and/or nicotinamide.

11. The composition of claim 10 wherein said antioxidant is vitamin A, C, D, or E or combinations thereof.

12. The composition of claim 4, wherein said gel comprises a compound selected from the group consisting of hyaluronic acid and chitosan.

13. The composition of claim 4 wherein said spray is an aerosol.

14. The composition of claim 4 wherein said spray dries on the skin.

15. The composition of claim 4 wherein said spray composition comprises gel-forming components.

16. A composition for stimulating the growth of cells comprising an effective amount of an isolated water soluble cytoplasmic fraction of salmon eggs comprising protein and messenger ribonucleic acid, wherein the protein content of said cytoplasmic fraction is about 100 to 380 mg/ml and said cytoplasmic fraction causes an increase in expression of OCT4 and SOX2 gene expression when applied to 293T cells.

* * * * *